(12) United States Patent
Daniel et al.

(10) Patent No.: US 11,911,249 B2
(45) Date of Patent: Feb. 27, 2024

(54) FLUID-ABSORBENT ARTICLE

(71) Applicant: BASF SE, Ludwigshafen am Rhein (DE)

(72) Inventors: Thomas Daniel, Ludwigshafen (DE); Christophe Bauduin, Ludwigshafen (DE); Katrin Baumann, Ludwigshafen (DE); Katarzyna Dobrosielska-Oura, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 1054 days.

(21) Appl. No.: 16/483,645

(22) PCT Filed: Jan. 29, 2018

(86) PCT No.: PCT/EP2018/052089
§ 371 (c)(1),
(2) Date: Aug. 5, 2019

(87) PCT Pub. No.: WO2018/141677
PCT Pub. Date: Aug. 9, 2018

(65) Prior Publication Data
US 2020/0121521 A1   Apr. 23, 2020

(30) Foreign Application Priority Data
Feb. 6, 2017 (EP) .................... 17154877

(51) Int. Cl.
*A61F 13/53* (2006.01)
*A61F 13/15* (2006.01)
*A61F 13/537* (2006.01)

(52) U.S. Cl.
CPC ........... *A61F 13/53* (2013.01); *A61F 13/537* (2013.01); *A61F 2013/15406* (2013.01);
(Continued)

(58) Field of Classification Search
CPC ............ A61F 13/53; A61F 2013/15406; A61F 2013/1556; A61F 13/537;
(Continued)

(56) References Cited

U.S. PATENT DOCUMENTS

| | | | |
|---|---|---|---|
| 3,243,321 A | | 3/1966 | Rowand |
| 5,037,409 A | * | 8/1991 | Chen .................... A61F 13/5376 |
| | | | 604/358 |
| 5,269,980 A | | 12/1993 | Levendis |
| 5,599,335 A | * | 2/1997 | Goldman ................ A61L 15/42 |
| | | | 604/378 |
| 5,800,418 A | * | 9/1998 | Ahr .................... A61F 13/15203 |
| | | | 604/374 |

(Continued)

FOREIGN PATENT DOCUMENTS

| | | |
|---|---|---|
| DE | 3314019 A1 | 1/1984 |
| DE | 3523617 A1 | 1/1986 |

(Continued)

OTHER PUBLICATIONS

International Search Report and Written Opinion issued in International Application No. PCT/EP2018/052089, dated Apr. 11, 2018, 11 pages.

(Continued)

*Primary Examiner* — Michele Kidwell
(74) *Attorney, Agent, or Firm* — Armstrong Teasdale LLP

(57) ABSTRACT

Provided herein are fluid-absorbent articles, fluid absorbent cores, and fluid-absorbent mixtures with improved properties, especially rewet performance and liquid acquisition. The fluid-absorbent article includes (A) an upper liquid-pervious sheet, (B) a lower liquid-impervious sheet, (C) a fluid-absorbent core including from 60 to 20% by weight fibrous material and from 40 to 80% by weight of at least a first type of water-absorbent polymer particles, (G) and at least a second type of water-absorbent polymer particles (H) based on the sum of water-absorbent polymer particles and fibrous material, (D) an optional acquisition-distribution layer (D) between (A) and (C), (F) other optional components, wherein the first type of water absorbent polymer (Continued)

Figure 1:
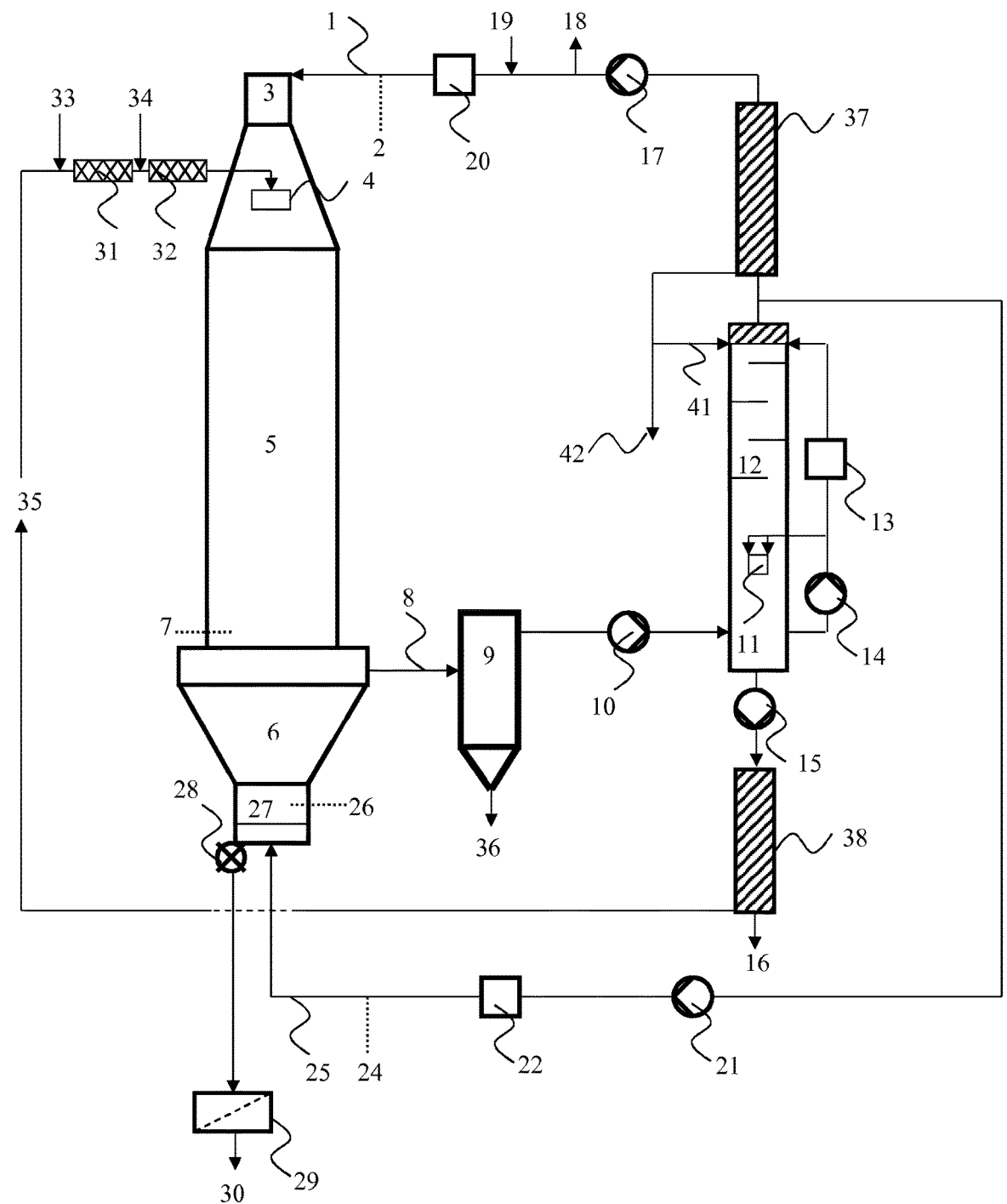

particles (G) of the fluid-absorbent core (C) have a SFC of at least $20\times10^{-7}$ cm$^3\cdot$s/g, and wherein the at least second type of water-absorbent polymer particles (H) of the fluid-absorbent core have a sphericity of at least 0.80.

18 Claims, 11 Drawing Sheets

(52) U.S. Cl.
CPC ............... *A61F 2013/1556* (2013.01); *A61F 2013/15959* (2013.01); *A61F 2013/15967* (2013.01); *A61F 2013/15983* (2013.01); *A61F 2013/530591* (2013.01); *A61F 2013/530613* (2013.01); *A61F 2013/5307* (2013.01); *A61F 2013/530788* (2013.01)

(58) Field of Classification Search
CPC .. A61F 2013/15959; A61F 2013/15967; A61F 2013/15983; A61F 2013/530481; A61F 2013/530591; A61F 2013/530613; A61F 2013/5307; A61F 2013/530708; A61F 2013/530788; A61L 15/60
See application file for complete search history.

(56) References Cited

U.S. PATENT DOCUMENTS

| | | | |
|---|---|---|---|
| 6,239,230 B1 | 5/2001 | Eckert | |
| 6,241,928 B1 | 6/2001 | Hatsuda | |
| 6,323,387 B1* | 11/2001 | Soga | A61F 13/53 604/385.01 |
| 6,972,011 B2 | 12/2005 | Maeda | |
| 8,669,410 B2* | 3/2014 | Weismantel | A61F 13/537 604/374 |
| 8,796,174 B2* | 8/2014 | Weismantel | A61F 13/15658 502/402 |
| 8,895,800 B2* | 11/2014 | Weismantel | A61F 13/53 604/372 |
| 9,480,968 B2* | 11/2016 | Weismantel | A61F 13/53 |
| 10,881,555 B2* | 1/2021 | Panayotova | B32B 7/14 |
| 2003/0097113 A1* | 5/2003 | Molee | A61F 13/5376 604/383 |
| 2011/0059329 A1* | 3/2011 | Dobrawa | A61L 15/60 428/522 |
| 2011/0162989 A1 | 7/2011 | Ducker | |
| 2011/0238026 A1 | 9/2011 | Zhang et al. | |
| 2011/0270204 A1 | 11/2011 | Fukudome | |
| 2011/0276019 A1* | 11/2011 | Kakimoto | A61F 13/531 604/372 |
| 2015/0011388 A1 | 1/2015 | Matsumoto et al. | |
| 2016/0206772 A1* | 7/2016 | Schröder | A61L 15/60 |
| 2017/0266336 A1 | 9/2017 | Gande et al. | |
| 2017/0281422 A1 | 10/2017 | Herfert et al. | |
| 2017/0281425 A1 | 10/2017 | Herfert et al. | |
| 2017/0312148 A1* | 11/2017 | Dobrosielska-Oura | A61F 13/539 |
| 2018/0043052 A1 | 2/2018 | Bauer et al. | |
| 2018/0044486 A1 | 2/2018 | Bauer et al. | |
| 2018/0126032 A1 | 5/2018 | Mark et al. | |
| 2018/0141677 A1 | 5/2018 | Lapujade | |
| 2020/0060897 A1* | 2/2020 | Daniel | A61F 13/53 |

FOREIGN PATENT DOCUMENTS

| | | |
|---|---|---|
| DE | 3713601 A1 | 11/1988 |
| DE | 3825366 A1 | 2/1989 |
| DE | 4020780 C1 | 8/1991 |
| DE | 19543368 A1 | 5/1997 |
| DE | 19646484 A1 | 5/1997 |
| DE | 19807992 C1 | 7/1999 |
| DE | 019807502 A1 | 9/1999 |
| DE | 19854573 A1 | 5/2000 |
| DE | 10204937 A1 | 8/2003 |
| DE | 10204938 A1 | 8/2003 |
| DE | 10331450 A1 | 1/2005 |
| DE | 10331456 A1 | 2/2005 |
| DE | 10334584 A1 | 2/2005 |
| DE | 10355401 A1 | 6/2005 |
| EP | 083022 A2 | 7/1983 |
| EP | 0348180 A2 | 12/1989 |
| EP | 0450922 A2 | 10/1991 |
| EP | 0530438 A1 | 3/1993 |
| EP | 0543303 A1 | 5/1993 |
| EP | 0547847 A1 | 6/1993 |
| EP | 0559476 A1 | 9/1993 |
| EP | 0632068 A1 | 1/1995 |
| EP | 0640330 A1 | 3/1995 |
| EP | 0937736 A2 | 8/1999 |
| EP | 0999238 A1 | 5/2000 |
| EP | 1199327 A2 | 4/2002 |
| EP | 2301499 A1 | 3/2011 |
| EP | 2314264 A1 | 4/2011 |
| EP | 2387981 A1 | 11/2011 |
| EP | 2486901 A1 | 8/2012 |
| EP | 2524679 A1 | 11/2012 |
| EP | 2524680 A1 | 11/2012 |
| EP | 2565031 A1 | 3/2013 |
| WO | 1990015830 A1 | 12/1990 |
| WO | 1993021237 A1 | 10/1993 |
| WO | 1996040427 A1 | 12/1996 |
| WO | 2001038402 A1 | 5/2001 |
| WO | 2002032962 A2 | 4/2002 |
| WO | 2002055469 A1 | 7/2002 |
| WO | 2003031482 A1 | 4/2003 |
| WO | 2003078378 A1 | 9/2003 |
| WO | 2003104299 A1 | 12/2003 |
| WO | 2003104300 A1 | 12/2003 |
| WO | 2003104301 A1 | 12/2003 |
| WO | 2004024816 A1 | 3/2004 |
| WO | 2004035514 A1 | 4/2004 |
| WO | 2007031441 A2 | 3/2007 |
| WO | 2008009580 A1 | 1/2008 |
| WO | 2008040715 A2 | 4/2008 |
| WO | 2008052971 A1 | 5/2008 |
| WO | 2008069639 A1 | 6/2008 |
| WO | 2008086976 A1 | 7/2008 |
| WO | 2010004894 A1 | 1/2010 |
| WO | 2010004895 A1 | 1/2010 |
| WO | 2010076857 A1 | 7/2010 |
| WO | 2010082373 A1 | 7/2010 |
| WO | 2010118409 A1 | 10/2010 |
| WO | 2010133529 A2 | 11/2010 |
| WO | 2010143635 A1 | 12/2010 |
| WO | 2011026876 A1 | 3/2011 |
| WO | 2011084981 A1 | 7/2011 |
| WO | 2011086841 A1 | 7/2011 |
| WO | 2011086842 A1 | 7/2011 |
| WO | 2011086843 A1 | 7/2011 |
| WO | 2011086844 A1 | 7/2011 |
| WO | 2011117215 A1 | 9/2011 |
| WO | 2011117263 A1 | 9/2011 |
| WO | 2011117997 A1 | 9/2011 |
| WO | 2011136087 A1 | 11/2011 |
| WO | 2012045705 A1 | 4/2012 |
| WO | 2012048879 A1 | 4/2012 |
| WO | 2012052172 A1 | 4/2012 |
| WO | 2012052173 A1 | 4/2012 |
| WO | 2013007819 A1 | 1/2013 |
| WO | 2014079694 A1 | 5/2014 |
| WO | 2015028158 A1 | 3/2015 |
| WO | 2015028327 A1 | 3/2015 |
| WO | 2016207444 A1 | 12/2016 |
| WO | 2018029045 A1 | 2/2018 |

OTHER PUBLICATIONS

"Applications of Superabsorbent polymers", Modern Superabsorbent Polymer Technology, ed. Buchholz, et al., 1998, pp. 252-259.

(56) References Cited

OTHER PUBLICATIONS

European Search Report for EP Application No. 17154877.9, dated Jun. 20, 2017, 3 pages.
Graham, et al., "Commercial processes for the manufacture of Superabsorbent poylmers", Modern Superabsorbent Polymer Technology, ed. Buchholz, et al., 1998, pp. 69-117.

* cited by examiner

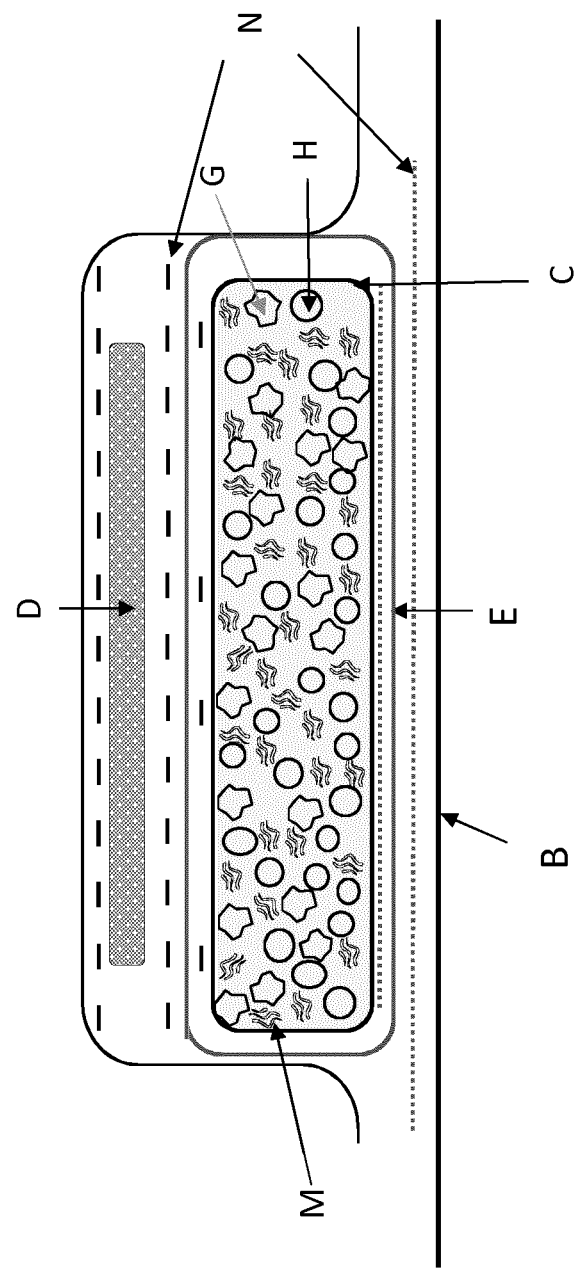

FLUID-ABSORBENT ARTICLE

CROSS-REFERENCE TO RELATED APPLICATIONS

This application is the national stage entry of PCT/EP2018/052089, filed on Jan. 29, 2018, which claims the benefit of priority to European Patent Application No. 17154877.9, filed on Feb. 6, 2017, which are incorporated by reference in their entirety herein.

The present invention relates to fluid-absorbent articles, fluid-absorbent cores and fluid-absorbent mixtures with improved properties, especially rewet performance and liquid acquisition.

According to the invention the fluid-absorbent article, comprising
- (A) an upper liquid-pervious sheet,
- (B) a lower liquid-impervious sheet,
- (C) a fluid-absorbent core comprising from 60 to 20% by weight fibrous material and from 40 to 80% by weight of at least a first type of water-absorbent polymer particles (G) and at least a second type of water-absorbent polymer particles (H) based on the sum of water-absorbent polymer particles (G, H) and fibrous material;
- (D) an optional acquisition-distribution layer (D) between (A) and (C),
- (F) other optional components, wherein the first type of water absorbent polymer particles
- (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

The production of fluid-absorbent articles is described in the monograph "Modern Superabsorbent Polymer Technology", F. L. Buchholz and A. T. Graham, Wiley-VCH, 1998, pages 252 to 258.

The preparation of water-absorbing polymer particles is likewise described in the monograph "Modern Superabsorbent Polymer Technology", F. L. Buchholz and A. T. Graham, Wiley-VCH, 1998, pages 71 to 103. The water-absorbing polymer particles are also referred to as "fluid-absorbing polymer particles", "superabsorbent polymers" or "superabsorbents". The preparation of water-absorbent polymer particles by polymerizing droplets of a monomer solution is described, for example, in EP 0 348 180 A1, WO 96/40427 A1, U.S. Pat. No. 5,269,980, WO 2008/009580 A1, WO 2008/052971 A1, WO2011/026876 A1, WO 2011/117263 A1, WO 2014/079694, WO 2015/028327 and WO 2015/028158.

The currently commercially available disposable diapers consist typically of a liquid-pervious topsheet (A), a liquid-impervious backsheet (B), a water-absorbing storage layer or absorbent core (C) between layers (A) and (B), and an acquisition distribution layer (D) between layers (A) and (C).

Usually the several layers of fluid-absorbent articles fulfill definite functions such as dryness for the upper liquid-pervious layer, vapor permeability without wetting through for the lower liquid-impervious layer, a flexible, vapor permeable and fluid-absorbent core, showing fast absorption rates and being able to retain quantities of body fluids and an acquisition-distribution layer (ADL) between the upper layer and the core, acting as transport and distribution layer of the discharged body fluids.

Generally the acquisition distribution layer (ADL) should ensure that the body liquids pass rapidly inside the structure of the absorbent article and are distributed uniformly throughout the thickness of the underlying storage layer or core instead of being absorbed in a localized manner only in the zones located underneath the points where the liquid arrives, or mainly in these zones. But often as there is a trend to reduce the thickness of fluid-absorbent articles the thickness of the ADL may be reduced as well, which results in reduced liquid distribution throughout the core and therefore also results in reduced liquid acquisition and high rewet for the fluid-absorbent article.

It is therefore an object of the present invention to provide fluid-absorbent articles with improved liquid acquisition to avoid leakage.

It is furthermore an object of the present invention to provide fluid-absorbent articles with improved rewet performance to ensure dryness of the wearer.

It is also an object of the present invention to provide fluid-absorbent mixtures, which ensure improved liquid acquisition and rewet in fluid-absorbent articles.

It is furthermore an object of the present invention to provide fluid-absorbent cores, which ensure improved rewet performance and liquid acquisition in fluid-absorbent articles.

The object is achieved by a fluid absorbent article, comprising
- (A) an upper liquid-pervious sheet,
- (B) a lower liquid-impervious sheet,
- (C) a fluid-absorbent core comprising from 60 to 20% by weight fibrous material and from 40 to 80% by weight of at least a first type of water-absorbent polymer particles (G) and at least a second type of water-absorbent polymer particles (H) based on the sum of water-absorbent polymer particles (G, H) and fibrous material;
- (D) an optional acquisition-distribution layer (D) between (A) and (C),
- (F) other optional components, wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

The object is furthermore achieved by a fluid-absorbent core comprising from 60 to 20% by weight fibrous material and from 40 to 80% by weight of at least a first type of water-absorbent polymer particles (G) and at least a second type of water-absorbent polymer particles (H) based on the sum of water-absorbent polymer particles (G, H) and fibrous material; wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

A fluid-absorbing core (C) according to this embodiment of the invention comprising at least two layers (K, L), wherein one of the layers (K) comprises from 60 to 20% by weight fibrous material and 40 to 80% by weight of the first type of water-absorbent polymer particles (G) based on the sum of water-absorbent polymer particles and fibrous material and the second layer (L) comprises from 60 to 20% by weight fibrous material and 40 to 80% by weight of the at least second type of water-absorbent polymer particles (H) based on the sum of water-absorbent polymer particles and fibrous material.

According to a preferred embodiment of the invention, in the fluid-absorbent core (C) the layer comprising the first type of water-absorbent polymer particles (G) is arranged in z-direction above the layer comprising the at least second type of water-absorbent polymer particles (H).

The object is furthermore achieved by a fluid-absorbent article, comprising (A) an upper liquid-pervious sheet,
(B) a lower liquid-impervious sheet,
(C) a fluid-absorbent core comprising from 60 to 20% by weight fibrous material and from 40 to 80% by weight of a mixture of at least a first type of water-absorbent polymer particles (G) and at least a second type of water-absorbent polymer particles (H) based on the sum of water-absorbent polymer particles (G, H) and fibrous material;
(D) an optional acquisition-distribution layer (D) between (A) and (C),
(F) other optional components, wherein the first type of water absorbent polymer particles
(G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

The object is also achieved by a fluid-absorbent core comprising from 60 to 20% by weight fibrous material and from 40 to 80% by weight of a mixture of at least a first type of water-absorbent polymer particles (G) and at least a second type of water-absorbent polymer particles (H) based on the sum of water-absorbent polymer particles (G, H) and fibrous material; wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

The object is also achieved by a mixture of at least a first type of water-absorbent polymer particles (G) and at least a second type of water-absorbent polymer particles (H) based on the sum of water-absorbent polymer particles (G, H) and fibrous material;
wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

According to another embodiment of the invention the first type of fluid-absorbent polymer particles (G) have a SFC of at least $20 \times 10^{-7}$ cm$^3 \cdot$s/g, preferably of at least $25 \times 10^{-7}$ cm$^3 \cdot$s/g, particularly preferred of at least $30 \times 10^{-7}$ cm$^3 \cdot$s/g, preferentially of at least $40 \times 10^{-7}$ cm$^3 \cdot$s/g, more preferably of at least $60 \times 10^{-7}$ cm$^3 \cdot$s/g, most preferably of at least $80 \times 10^{-7}$ cm$^3 \cdot$s/g, further most preferably of at least $100 \times 10^{-7}$ cm$^3 \cdot$s/g, but not above $200 \times 10^{-7}$ cm$^3 \cdot$s/g.

According to a further embodiment of the invention the second type of water-absorbent polymer particles (H) have an SFC of at maximum of $15 \times 10^{-7}$ cm$^3 \cdot$s/g, preferably of at maximum of $10 \times 10^{-7}$ cm$^3 \cdot$s/g, particularly preferred of at maximum of $5 \times 10^{-7}$ cm$^3 \cdot$s/g, more preferably of $3 \times 10^{-7}$ cm$^3 \cdot$s/g, most preferably of $0 \times 10^{-7}$ cm$^3 \cdot$s/g.

According to another embodiment the second type of water-absorbent polymer particles (H) of the inventive fluid-absorbent article, absorbent core or absorbent mixture respectively have a sphericity of at least 0.80, preferably of at least 0.85, particularly preferred of at least 0.90.

According to a further embodiment of the inventive the second type of water-absorbent polymer particles (H) have a sphericity of at least 0.80 and a SFC of at maximum $5 \times 10^{-7}$ cm$^3 \cdot$s/g.

According to another embodiment of the inventive fluid absorbent article, absorbent core or absorbent mixture respectively the production process of the first type of water absorbent polymer particles (G) of the fluid-absorbent core (C) comprises the steps of polymerization of the monomer solution, forming and comminuting a polymer gel, drying and grinding of the polymer.

According to another embodiment of the invention the production process of the second type of water absorbent polymer particles (H) of the fluid-absorbent core (C) are produced by polymerizing droplets of a monomer solution in a surrounding heated gas phase.

The water absorbent polymer particles (G, H) of the fluid-absorbent article absorbent core, or absorbent mixture respectively according to one embodiment of the invention are surface-postcrosslinked.

According to an embodiment of the invention it is also possible that a fluid-absorbent core or a fluid-absorbent article comprising the inventive mixture provides a lower sum of acquisition times for 4 succeeding insults compared to a core and/or absorbent article containing only the first type (G) or the second type (H) of water-absorbent polymers respectively in the same amount by weight as the mixture.

The mixture has a lower liquid acquisition time for 4 insults (this means absorbs the liquid faster) than both individual components in the same amount. According to this embodiment the mixture provides a synergism in respect to the liquid acquisition time.

Suitable water-absorbent polymers are produced by a process, comprising the steps forming water-absorbent polymer particles by polymerizing a monomer solution, comprising a) at least one ethylenically unsaturated monomer which bears acid groups and may be at least partly neutralized,
b) optionally one or more crosslinker,
c) at least one initiator,
d) optionally one or more ethylenically unsaturated monomers copolymerizable with the monomers mentioned under a),
e) optionally one or more water-soluble polymers, and
f) water,
optionally coating of water-absorbent polymer particles with at least one surface-postcrosslinker and thermal surface-postcrosslinking of the coated water-absorbent polymer particles.

According to one embodiment of the invention the content of residual monomers in the water-absorbent polymer particles prior to the coating with the surface-postcrosslinker is preferably in the range from 0.03 to 15% by weight, and the temperature during the thermal surface-postcrosslinking is in the range from 100 to 180° C.

DETAILED DESCRIPTION OF THE INVENTION

A. Definitions

As used herein, the term "fluid-absorbent article" refers to any three-dimensional solid material being able to acquire and store fluids discharged from the body. Preferred fluid-absorbent articles are disposable fluid-absorbent articles that are designed to be worn in contact with the body of a user such as disposable fluid-absorbent pantyliners, sanitary napkins, catamenials, incontinence inserts/pads, diapers, training pant diapers, breast pads, interlabial inserts/pads or other articles useful for absorbing body fluids.

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core or "absorbent core" refers to a fluid-absorbent composition comprising water-absorbent polymer particles and optionally fibrous material, nonwoven material, tissue material and optionally adhesive. The fluid-absorbent core is primarily responsible for the fluid handling/management of the fluid-absorbent article including acquisition, transport, distribution, storage and retention of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein the term "x-dimension" refers to the length, and the term "y-dimension" refers to the width of the fluid-absorbent composition, layer, core or article. Generally, the term "x-y-dimension" refers to the plane, orthogonal to the height or thickness of the fluid-absorbent composition, layer, core or article.

As used herein the term "z-dimension" refers to the dimension orthogonal to the length and width of the fluid absorbent composition, layer, core or article. Generally, the term "z-dimension" refers to the height of the fluid-absorbent composition, layer, core or article.

As used herein, the term "basis weight" indicates the weight of the fluid-absorbent core per square meter or of the acquisition-distribution layer per square meter respectively. The basis weight is determined at discrete regions of the fluid-absorbent core or acquisition distribution layer respectively.

Further, it should be understood, that the term "upper" refers to fluid-absorbent composition which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the component which is furthermost away from the wearer of the fluid-absorbent article, hereinafter described as "lower liquid-impervious layer".

As used herein, the term "liquid-pervious" refers to a substrate, layer or a laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

As used herein, the term "chassis" refers to fluid-absorbent material comprising the upper liquid-pervious layer and the lower liquid-impervious layer, elastication and closure systems for the absorbent article.

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "body fluids" refers to any fluid produced and discharged by human or animal body, such as urine, menstrual fluids, faeces, vaginal secretions and the like.

As used herein, the term "breathable" refers to a substrate, layer, film or a laminate that allows vapour to escape from the fluid-absorbent article, while still preventing fluids from leakage.

Breathable substrates, layers, films or laminates may be porous polymeric films, nonwoven laminates from spunbond and melt-blown layers, laminates from porous polymeric films and nonwovens.

As used herein, the term "longitudinal" refers to a direction running perpendicular from a waist edge to an opposing waist edge of the fluid-absorbent article.

B. Water-Absorbent Polymer Particles

The water-absorbent polymer particles are prepared by a process, comprising the steps forming water-absorbent polymer particles by polymerizing a monomer solution, comprising
g) at least one ethylenically unsaturated monomer which bears acid groups and may be at least partly neutralized,
h) optionally one or more crosslinker,
i) at least one initiator,
j) optionally one or more ethylenically unsaturated monomers copolymerizable with the monomers mentioned under a),
k) optionally one or more water-soluble polymers, and
l) water, and
optionally coating of water-absorbent polymer particles with at least one surface-postcrosslinker and thermal surface-postcrosslinking of the coated water-absorbent polymer particles.

Preferably the content of residual monomers in the water-absorbent polymer particles prior to coating with a surface-postcrosslinker is in the range from 0.03 to 15% by weight, a preferred surface-postcrosslinker is an alkylene carbonate, and the temperature during the thermal surface-postcrosslinking is in the range from 100 to 180° C.

The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized in the range of 0 to 100 mol %, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogencarbonates and hydroxides of magnesium, calcium, strontium, zinc or aluminum as powders, slurries or solutions and mixtures of any of the above neutralization agents. Example for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tartrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), Trilon® M (methylglycinediacetic acid) and Cublen®.

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, poly-ethyleneglycole diallylethers (based on polyethylene glycole having a molecular weight between 400 and 20000 g/mol), N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 18-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.0001 to 0.6% by weight, more preferably from 0.001 to 0.2% by weight, most preferably from 0.01 to 0.06% by weight, based in each case on monomer a). On increasing the amount of crosslinker b) the centrifuge retention capacity (CRC) decreases and the absorption under a pressure of 21.0 g/cm$^2$ (AUL) passes through a maximum.

The surface-postcrosslinked polymer particles of the present invention surprisingly require very little or even no cross-linker during the polymerization step. So, in one particularly preferred embodiment of the present invention no crosslinker b) is used.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane] dihydrochloride and 2,2'-azobis[2-(5-methyl-2-imidazolin-2-yl)propane] dihydrochloride, 2,2'-azobis(2-amidinopropane) dihydrochloride, 4,4'-azobis(4-cyanopentanoic acid), 4,4'-azobis(4-cyanopentanoic acid) sodium salt, 2,2'-azobis[2-methyl-N-(2-hydroxyethyl)propionamide], and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggolite Chemicals; Heilbronn; Germany). Of course it is also possible within the scope of the present invention to use the purified salts or acids of 2-hydroxy-2-sulfinatoacetic acid and 2-hydroxy-2-sulfonatoacetic acid—the latter being available as sodium salt under the trade name Blancolene® (Brüggolite Chemicals; Heilbronn; Germany).

The initiators are used in customary amounts, for example in amounts of from 0.001 to 5% by weight, preferably from 0.01 to 2% by weight, most preferably from 0.05 to 0.5% by weight, based on the monomers a).

Examples of ethylenically unsaturated monomers d) which are copolymerizable with the monomers a) are acrylamide, methacrylamide, hydroxyethyl acrylate, hydroxyethyl methacrylate, dimethylaminoethyl acrylate, dimethylaminoethyl methacrylate, dimethylaminopropyl acrylate and diethylaminopropyl methacrylate.

Useful water-soluble polymers e) include polyvinyl alcohol, modified polyvinyl alcohol comprising acidic side groups for example Poval® K (Kuraray Europe GmbH; Frankfurt; Germany), polyvinylpyrrolidone, starch, starch derivatives, modified cellulose such as methylcellulose, carboxymethylcellulose or hydroxyethylcellulose, gelatin, polyglycols or polyacrylic acids, polyesters and polyamides, polylactic acid, polyglycolic acid, co-polylactic-polyglycolic acid, polyvinylamine, polyallylamine, water soluble copolymers of acrylic acid and maleic acid available as Sokalan® (BASF SE; Ludwigshafen; Germany), preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pa·s, more preferably from 0.004 to 0.015 Pa·s, most preferably from 0.005 to 0.01 Pa·s. The mean droplet diameter in the droplet generation rises with rising dynamic viscosity.

The monomer solution has, at 20° C., a density of preferably from 1 to 1.3 g/cm$^3$, more preferably from 1.05 to 1.25 g/cm$^3$, most preferably from 1.1 to 1.2 g/cm$^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension.

Polymerization

The monomer solution is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To produce water-absorbent polymer particles, especially with a roundness of at least 0.80, polymerizing droplets of the monomer in a surrounding heated gas phase, for example using a system described in WO 2008/040715 A2, WO 2008/052971 A1, WO 2008/069639 A1 and WO 2008/086976 A1, WO 2014/079694, WO 2015/028327, WO 2015/028158 is performed.

It is preferred that the fluid-absorbent mixture and the fluid-absorbent article according to the invention respectively comprises water-absorbent polymer particles produced by polymerizing droplets of the monomer in a surrounding heated gas phase.

The droplets are preferably generated by means of a droplet plate. A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

Within the scope of the present invention it is also possible to use two or more droplet plates with different bore diameters so that a range of desired particle sizes can be produced. It is preferable that each droplet plate carries only one bore diameter, however mixed bore diameters in one plate are also possible.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. In a preferred embodiment of the present invention the pressure drop is from 4 to 5 bar. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water. The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water. Useful coatings include for example fluorous polymers, such as perfluoroalkoxyethylene, polytetrafluoroethylene, ethylene-chlorotrifluoroethylene copolymers, ethylene-tetrafluoroethylene copolymers and fluorinated polyethylene.

The coatings can be applied to the substrate as a dispersion, in which case the solvent is subsequently evaporated off and the coating is heat treated. For polytetrafluoroethylene this is described for example in U.S. Pat. No. 3,243,321.

Further coating processes are to be found under the headword "Thin Films" in the electronic version of "Ullmann's Encyclopedia of Industrial Chemistry" (Updated Sixth Edition, 2000 Electronic Release).

The coatings can further be incorporated in a nickel layer in the course of a chemical nickelization. It is the poor wettability of the droplet plate that leads to the production of monodisperse droplets of narrow droplet size distribution.

The droplet plate has preferably at least 5, more preferably at least 25, most preferably at least 50 and preferably up to 2000, more preferably up to 1500 bores, most preferably up to 1000. The number of bores is determined mainly by geometrical and manufacturing constraints and can be adjusted to practical use conditions even outside the above given range.

The diameter of the bores is adjusted to the desired droplet size.

The spacing of the bores is usually from 2 to 50 mm, preferably from 3 to 40 mm, more preferably from 4 to 30 mm, most preferably from 5 to 25 mm. Smaller spacings of the bores may cause agglomeration of the polymerizing droplets.

The diameter of the bores size area is 1900 to 22300 $\mu m^2$, more preferably from 7800 to 20100 $\mu m^2$, most preferably from 11300 to 17700 $\mu m^2$. Circular bores are preferred with a bore size from 50 to 170 m, more preferably from 100 to 160 m, most preferably from 120 to 150 m.

For optimizing the average particle diameter, droplet plates with different bore diameters can be used. The variation can be done by different bores on one plate or by using different plates, where each plate has a different bore diameter. The average particle size distribution can be monomodal, bimodal or multimodal. Most preferably it is monomodal or bimodal.

The temperature of the monomer solution as it passes through the bore is preferably from 5 to 80° C., more preferably from 10 to 70° C., most preferably from 30 to 60° C.

A carrier gas flows through the reaction zone. The carrier gas may be conducted through the reaction zone in cocurrent to the free-falling droplets of the monomer solution, i.e. from the top downward. After one pass, the gas is preferably recycled at least partly, preferably to an extent of at least 50%, more preferably to an extent of at least 75%, into the reaction zone as cycle gas. Typically, a portion of the carrier gas is discharged after each pass, preferably up to 10%, more preferably up to 3% and most preferably up to 1%.

The oxygen content of the carrier gas is preferably from 0.1 to 25% by volume, more preferably from 1 to 10% by volume, most preferably from 2 to 7% by weight. In the scope of the present invention it is also possible to use a carrier gas which is free of oxygen. As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbon dioxide, argon, xenon, krypton, neon, helium, sulfurhexafluoride. Any mixture of carrier gases may be used. It is also possible to use air as carrier gas. The carrier gas may also become loaded with water and/or acrylic acid vapors.

The gas velocity is preferably adjusted such that the flow in the reaction zone (5) is directed, for example no convection currents opposed to the general flow direction are present, and is preferably from 0.1 to 2.5 m/s, more preferably from 0.3 to 1.5 m/s, even more preferably from 0.5 to 1.2 m/s, most preferably from 0.7 to 0.9 m/s.

The gas entrance temperature, i.e. the temperature with which the gas enters the reaction zone, is preferably from 160 to 200° C., more preferably from 165 to 195° C., even more preferably from 170 to 190° C., most preferably from 175 to 185° C.

The steam content of the gas that enters the reaction zone is preferably from 0.01 to 0.15 kg per kg dry gas, more preferably from 0.02 to 0.12 kg per kg dry gas, most preferably from 0.03 to 0.10 kg per kg dry gas.

The gas entrance temperature is controlled in such a way that the gas exit temperature, i.e. the temperature with which the gas leaves the reaction zone, is less than 150° C., preferably from 90 to 140° C., more preferably from 100 to 130° C., even more preferably from 105 to 125° C., most preferably from 110 to 120° C.

The water-absorbent polymer particles can be divided into three categories: water-absorbent polymer particles of Type 1 are particles with one cavity, water-absorbent polymer particles of Type 2 are particles with more than one cavity, and water-absorbent polymer particles of Type 3 are solid particles with no visible cavity.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having more than one cavity (Type 2) show an improved mechanical stability.

The reaction can be carried out under elevated pressure or under reduced pressure, preferably from 1 to 100 mbar below ambient pressure, more preferably from 1.5 to 50 mbar below ambient pressure, most preferably from 2 to 10 mbar below ambient pressure.

The reaction off-gas, i.e. the gas leaving the reaction zone, may be cooled in a heat exchanger. This condenses water and unconverted monomer a). The reaction off-gas can then be reheated at least partly and recycled into the reaction zone as cycle gas. A portion of the reaction off-gas can be discharged and replaced by fresh gas, in which case water and unconverted monomers a) present in the reaction off-gas can be removed and recycled.

Particular preference is given to a thermally integrated system, i.e. a portion of the waste heat in the cooling of the off-gas is used to heat the cycle gas.

The reactors can be trace-heated. In this case, the trace heating is adjusted such that the wall temperature is at least 5° C. above the internal surface temperature and condensation on the surfaces is reliably prevented.

Thermal Posttreatment

The water-absorbent polymer particles obtained by dropletization may be thermal posttreated for adjusting the content of residual monomers to the desired value.

Generally the level of residual monomers can be influenced by process parameter settings, for example; the temperature of posttreatment of the water-absorbent particles. The residual monomers can be removed better at relatively high temperatures and relatively long residence times. What is important here is that the water-absorbent polymer particles are not too dry. In the case of excessively dry particles, the residual monomers decrease only insignificantly. Too high a water content increases the caking tendency of the water-absorbent polymer particles.

The thermal posttreatment can be done in a fluidized bed. In a preferred embodiment of the present invention an internal fluidized bed is used. An internal fluidized bed means that the product of the dropletization polymerization is accumulated in a fluidized bed below the reaction zone.

The residual monomers can be removed during the thermal posttreatment. What is important here is that the water-absorbent polymer particles are not too dry. In the case of excessively dry particles, the residual monomers decrease only insignificantly. A too high water content increases the caking tendency of the water-absorbent polymer particles.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.3 to 2.5 m/s, more preferably from 0.4 to 2.0 m/s, most preferably from 0.5 to 1.5 m/s.

The pressure drop over the bottom of the internal fluidized bed is preferably from 1 to 100 mbar, more preferably from 3 to 50 mbar, most preferably from 5 to 25 mbar.

The moisture content of the water-absorbent polymer particles at the end of the thermal posttreatment is preferably from 1 to 20% by weight, more preferably from 2 to 15% by weight, even more preferably from 3 to 12% by weight, most preferably 5 to 8% by weight.

The temperature of the water-absorbent polymer particles during the thermal posttreatment is from 20 to 140° C., preferably from 40 to 110° C., more preferably from 50 to 105° C., most preferably from 60 to 100° C.

The average residence time in the internal fluidized bed is from 10 to 300 minutes, preferably from 60 to 270 minutes, more preferably from 40 to 250 minutes, most preferably from 120 to 240 minutes.

The condition of the fluidized bed can be adjusted for reducing the amount of residual monomers of the water-absorbent polymers leaving the fluidized bed. The amount of residual monomers can be reduced to levels below 0.1% by weight by a thermal posttreatment using additional steam.

The steam content of the gas is preferably from 0.005 to 0.25 kg per kg of dry gas, more preferably from 0.01 to 0.2 kg per kg of dry gas, most preferably from 0.02 to 0.15 kg per kg of dry gas.

By using additional steam the condition of the fluidized bed can be adjusted that the amount of residual monomers of the water-absorbent polymers leaving the fluidized bed is from 0.03 to 15% by weight, preferably from 0.05 to 12% by weight, more preferably from 0.1 to 10% by weight, even more preferably from 0.15 to 7.5% by weight most preferably from 0.2 to 5% by weight, even most preferably from 0.25 to 2.5% by weight.

The level of residual monomers in the water-absorbent polymer has in important impact on the properties of the later formed surface-postcrosslinked water-absorbent polymer particles. That means that very low levels of residual monomers must be avoided.

It is preferred that the thermal posttreatment is completely or at least partially done in an external fluidized bed. The operating conditions of the external fluidized bed are within the scope for the internal fluidized bed as described above.

It is alternatively preferred that the thermal posttreatment is done in an external mixer with moving mixing tools as e.g. described in WO 2011/117215 A1, preferably horizontal mixers, such as screw mixers, disk mixers, screw belt mixers and paddle mixers. Suitable mixers are, for example, Becker shovel mixers (Gebr. Lödige Maschinenbau GmbH; Paderborn; Germany), Nara paddle mixers (NARA Machinery Europe; Frechen; Germany), Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (GebrOder Ruberg GmbH & Co KG, Nieheim, Germany). Ruberg continuous flow mixers, Becker shovel mixers and Pflugschar® plowshare mixers are preferred.

The thermal posttreatment can be done in a discontinuous external mixer or a continuous external mixer.

The amount of gas to be used in the discontinuous external mixer is preferably from 0.01 to 5 $Nm^3/h$, more preferably from 0.05 to 2 $Nm^3/h$, most preferably from 0.1 to 0.5 $Nm^3/h$, based in each case on kg water-absorbent polymer particles.

The amount of gas to be used in the continuous external mixer is preferably from 0.01 to 5 $Nm^3/h$, more preferably from 0.05 to 2 $Nm^3/h$, most preferably from 0.1 to 0.5 $Nm^3/h$, based in each case on kg/h throughput of water-absorbent polymer particles.

The other constituents of the gas are preferably nitrogen, carbon dioxide, argon, xenon, krypton, neon, helium, air or air/nitrogen mixtures, more preferably nitrogen or air/nitrogen mixtures comprising less than 10% by volume of oxygen. Oxygen may cause discoloration.

The morphology of the water-absorbent polymer particles can also be controlled by the reaction conditions during thermal posttreatment. Water-absorbent polymer particles having a high amount of particles with one cavity (Type 1) can be prepared by using high product temperatures and short residence times. Water-absorbent polymer particles having a high amount of particles with more than one cavity (Type 2) can be prepared by using low product temperatures and long residence times.

Surface-Postcrosslinking

The polymer particles can be surface-postcrosslinked for further improvement of the properties.

Surface-postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230. Also ethyleneoxide, aziridine, glycidol, oxetane and its derivatives may be used.

Polyvinylamine, polyamidoamines and polyvinylalcohole are examples of multifunctional polymeric surface-postcrosslinkers.

In addition, DE 40 20 780 C1 describes alkylene carbonates, DE 198 07 502 A1 describes 1,3-oxazolidin-2-one and its derivatives such as 2-hydroxyethyl-1,3-oxazolidin-2-one, DE 198 07 992 C1 describes bis- and poly-1,3-oxazolidin-2-ones, EP 0 999 238 A1 describes bis- and poly-1,3-oxazolidines, DE 198 54 573 A1 describes 2-oxotetrahydro-1,3-oxazine and its derivatives, DE 198 54 574 A1 describes N-acyl-1,3-oxazolidin-2-ones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable surface-postcrosslinkers.

In addition, it is also possible to use surface-postcrosslinkers which comprise additional polymerizable ethylenically unsaturated groups, as described in DE 37 13 601 A1.

The at least one surface-postcrosslinker is selected from alkylene carbonates, 1,3-oxazolidin-2-ones, bis- and poly-1,3-oxazolidin-2-ones, bis- and poly-1,3-oxazolidines, 2-oxotetrahydro-1,3-oxazines, N-acyl-1,3-oxazolidin-2-ones, cyclic ureas, bicyclic amide acetals, oxetanes, and morpholine-2,3-diones. Suitable surface-postcrosslinkers are ethylene carbonate, 3-methyl-1,3-oxazolidin-2-one, 3-methyl-3-oxethanmethanol, 1,3-oxazolidin-2-one, 3-(2-hydroxyethyl)-1,3-oxazolidin-2-one, 1,3-dioxan-2-one or a mixture thereof.

It is also possible to use any suitable mixture of surface-postcrosslinkers. It is particularly favorable to use mixtures of 1,3-dioxolan-2-on (ethylene carbonate) and 1,3-oxazolidin-2-ones. Such mixtures are obtainable by mixing and partly reacting of 1,3-dioxolan-2-on (ethylene carbonate) with the corresponding 2-amino-alcohol (e.g. 2-aminoethanol) and may comprise ethylene glycol from the reaction.

It is preferred that at least one alkylene carbonate is used as surface-postcrosslinker. Suitable alkylene carbonates are 1,3-dioxolan-2-on (ethylene carbonate), 4-methyl-1,3-dioxolan-2-on (propylene carbonate), 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on (glycerine carbonate), 1,3-dioxane-2-on (trimethylene carbonate), 4-methyl-1,3-dioxane-2-on, 4,6-dimethyl-1,3-dioxane-2-on and 1,3-dioxepan-2-on, preferably 1,3-dioxolan-2-on (ethylene carbonate) and 1,3-dioxane-2-on (trimethylene carbonate), most preferably 1,3-dioxolan-2-on (ethylene carbonate).

The amount of surface-postcrosslinker is preferably from 0.1 to 10% by weight, more preferably from 0.5 to 7.5% by weight, most preferably from 1 to 5% by weight, based in each case on the polymer.

The content of residual monomers in the water-absorbent polymer particles prior to the coating with the surface-postcrosslinker is in the range from 0.03 to 15% by weight, preferably from 0.05 to 12% by weight, more preferably from 0.1 to 10% by weight, even more preferably from 0.15 to 7.5% by weight, most preferably from 0.2 to 5% by weight, even most preferably from 0.25 to 2.5% by weight.

The moisture content of the water-absorbent polymer particles prior to the thermal surface-postcrosslinking is preferably from 1 to 20% by weight, more preferably from 2 to 15% by weight, most preferably from 3 to 10% by weight.

Polyvalent cations can be applied to the particle surface in addition to the surface-postcrosslinkers before, during or after the thermal surface-postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium, and mixtures thereof. Possible counterions are chloride, bromide, sulfate, hydrogensulfate, methanesulfate, carbonate, hydrogencarbonate, nitrate, hydroxide, phosphate, hydrogenphosphate, dihydrogenphosphate, glycophosphate and carboxylate, such as acetate, glycolate, tartrate, formiate, propionate, 3-hydroxypropionate, lactamide and lactate, and mixtures thereof. Aluminum sulfate, aluminum acetate, and aluminum lactate are preferred. Aluminum lactate is more preferred. Using the inventive process in combination with the use of aluminum lactate, water-absorbent polymer particles having an extremely high total liquid uptake at lower centrifuge retention capacities (CRC) can be prepared.

Apart from metal salts, it is also possible to use polyamines and/or polymeric amines as polyvalent cations. A single metal salt can be used as well as any mixture of the metal salts and/or the polyamines above.

Preferred polyvalent cations and corresponding anions are disclosed in WO 2012/045705 A1 and are expressly incorporated herein by reference. Preferred polyvinylamines are disclosed in WO 2004/024816 A1 and are expressly incorporated herein by reference.

The amount of polyvalent cation used is, for example, from 0.001 to 1.5% by weight, preferably from 0.005 to 1% by weight, more preferably from 0.02 to 0.8% by weight, based in each case on the polymer.

The addition of the polyvalent metal cation can take place prior, after, or cocurrently with the surface-postcrosslinking. Depending on the formulation and operating conditions employed it is possible to obtain a homogeneous surface coating and distribution of the polyvalent cation or an inhomogeneous typically spotty coating. Both types of coatings and any mixes between them are useful within the scope of the present invention.

The surface-postcrosslinking is typically performed in such a way that a solution of the surface-postcrosslinker is sprayed onto the hydrogel or the dry polymer particles. After the spraying, the polymer particles coated with the surface-postcrosslinker are dried thermally and cooled.

The spraying of a solution of the surface-postcrosslinker is preferably performed in mixers with moving mixing tools, such as screw mixers, disk mixers and paddle mixers. Suitable mixers are, for example, vertical Schugi Flexomix® mixers (Hosokawa Micron BV; Doetinchem; the Netherlands), Turbolizers® mixers (Hosokawa Micron BV; Doetinchem; the Netherlands), horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (GebrÖder Ruberg GmbH & Co KG, Nieheim, Germany). Ruberg continuous flow mixers and horizontal Pflugschar® plowshare mixers are preferred. The surface-postcrosslinker solution can also be sprayed into a fluidized bed.

The solution of the surface-postcrosslinker can also be sprayed on the water-absorbent polymer particles during the thermal posttreatment. In such case the surface-postcrosslinker can be added as one portion or in several portions along the axis of thermal posttreatment mixer.

In one embodiment it is preferred to add the surface-postcrosslinker at the end of the thermal posttreatment step. As a particular advantage of adding the solution of the surface-postcrosslinker during the thermal posttreatment step it may be possible to eliminate or reduce the technical effort for a separate surface-postcrosslinker addition mixer.

The surface-postcrosslinkers are typically used as an aqueous solution. The addition of nonaqueous solvent can be used to improve surface wetting and to adjust the penetration depth of the surface-postcrosslinker into the polymer particles.

The thermal surface-postcrosslinking is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Moreover, it is also possible to use fluidized bed dryers. In the latter case the reaction times may be shorter compared to other embodiments.

When a horizontal dryer is used then it is often advantageous to set the dryer up with an inclined angle of a few degrees vs. the earth surface in order to impart proper product flow through the dryer. The angle can be fixed or may be adjustable and is typically between 0 to 10 degrees, preferably 1 to 6 degrees, most preferably 2 to 4 degrees.

A contact dryer can be used that has two different heating zones in one apparatus. For example Nara paddle driers are available with just one heated zone or alternatively with two heated zones. The advantage of using a two or more heated zone dryer is that different phases of the thermal post-treatment and/or of the post-surface-crosslinking can be combined.

It is possible to use a contact dryer with a hot first heating zone which is followed by a temperature holding zone in the same dryer. This set up allows a quick rise of the product temperature and evaporation of surplus liquid in the first heating zone, whereas the rest of the dryer is just holding the product temperature stable to complete the reaction.

It is also possible to use a contact dryer with a warm first heating zone which is then followed by a hot heating zone. In the first warm zone the thermal post-treatment is affected or completed whereas the surface-postcrosslinking takes place in the subsequential hot zone.

Typically a paddle heater with just one temperature zone is employed.

A person skilled in the art will depending on the desired finished product properties and the available base polymer qualities from the polymerization step choose any one of these set ups.

The thermal surface-postcrosslinking can be effected in the mixer itself, by heating the jacket, blowing in warm air or steam. Equally suitable is a downstream dryer, for example a shelf dryer, a rotary tube oven or a heatable screw. It is particularly advantageous to mix and dry in a fluidized bed dryer.

Preferred thermal surface-postcrosslinking temperatures are usually in the range of 100-195° C., mostly in the range of 100 to 180° C., preferably from 120 to 170° C., more preferably from 130 to 165° C., most preferably from 140 to 160° C. The preferred residence time at this temperature in the reaction mixer or dryer is preferably at least 5 minutes, more preferably at least 20 minutes, most preferably at least 40 minutes, and typically at most 120 minutes.

It is preferable to cool the polymer particles after thermal surface-postcrosslinking. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures in the range from 20 to 150° C., preferably from 40 to 120° C., more preferably from 60 to 100° C., most preferably from 70 to 90° C. Cooling using warm water is preferred, especially when contact coolers are used.

Coating

To improve the properties, the water-absorbent polymer particles can be coated and/or optionally moistened. The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the surface-postcrosslinked water-absorbent polymer particles. Suitable coatings for controlling the acquisition behavior and improving the permeability (SFC or GBP) are, for example, inorganic inert substances, such as water-insoluble metal salts, organic polymers, cationic polymers, anionic polymers and polyvalent metal cations. Suitable coatings for improving the color stability are, for example reducing agents, chelating agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20 and Plantacare® 818 UP. Preferred coatings are aluminium dihydroxy monoacetate, aluminium sulfate, aluminium lactate, aluminium 3-hydroxypropionate, zirconium acetate, citric acid or its water soluble salts, di- and monophosphoric acid or their water soluble salts, Blancolen®, Brüggolite® FF7, Cublen®, Span® 20 and Plantacare® 818 UP.

If salts of the above acids are used instead of the free acids then the preferred salts are alkali-metal, earth alkali metal, aluminum, zirconium, titanium, zinc and ammonium salts.

Under the trade name Cublen® (Zschimmer & Schwarz Mohsdorf GmbH & Co KG; Burgstadt; Germany) the following acids and/or their alkali metal salts (preferably Na and K-salts) are available and may be used within the scope of the present invention for example to impart color-stability to the finished product:

1-Hydroxyethane-1,1-diphosphonic acid, Amino-tris (methylene phosphonic acid), Ethylenediamine-tetra(methylene phosphonic acid), Diethylenetriamine-penta(methylene phosphonic acid), Hexamethylene diamine-tetra (methylenephosphonic acid), Hydroxyethyl-amino-di (methylene phosphonic acid), 2-Phosphonobutane-1,2,4-tricarboxylic acid, Bis(hexamethylenetriamine penta (methylene phosphonic acid).

Most preferably 1-Hydroxyethane-1,1-diphosphonic acid or its salts with sodium, potassium, or ammonium are employed. Any mixture of the above Cublenes® can be used.

Alternatively, any of the chelating agents described before for use in the polymerization can be coated onto the finished product.

Suitable inorganic inert substances are silicates such as montmorillonite, kaolinite and talc, zeolites, activated carbons, polysilicic acids, magnesium carbonate, calcium carbonate, calcium phosphate, aluminum phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the water-absorbent polymer particles are coated with inorganic inert substances, the amount of inorganic inert substances used, based on the water-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoroethylene. Other examples are styrene-isoprene-styrene block-copolymers or styrenebutadiene-styrene block-copolymers. Another example are silanole-group bearing polyvinylalcoholes available under the trade name Poval® R (Kuraray Europe GmbH; Frankfurt; Germany).

Suitable cationic polymers are polyalkylenepolyamines, cationic derivatives of polyacrylamides, polyethyleneimines and polyquaternary amines.

Polyquaternary amines are, for example, condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or polyfunctional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent, as dispersion in an aqueous or water-miscible dispersant or in substance.

When the water-absorbent polymer particles are coated with a cationic polymer, the use amount of cationic polymer based on the water-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable anionic polymers are polyacrylates (in acidic form or partially neutralized as salt), copolymers of acrylic acid and maleic acid available under the trade name Sokalan® (BASF SE; Ludwigshafen; Germany), and polyvinylalcohols with built in ionic charges available under the trade name Poval® K (Kuraray Europe GmbH; Frankfurt; Germany).

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^{+}$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, acetate, formiate, propionate, nitrate, sulfate and methanesulfate. The metal salts are preferably used as a solution or as a stable aqueous colloidal dispersion. The solvents used for the metal salts may be water, alcohols, ethylenecarbonate, propylenecarbonate, dimethylformamide, dimethyl sulfoxide and mixtures thereof. Particular preference is given to water and water/alcohol mixtures, such as water/methanol, water/isopropanol, water/1,3-propanediole, water/1,2-propandiole/1,4-butanediole or water/propylene glycol.

When the water-absorbent polymer particles are coated with a polyvalent metal cation, the amount of polyvalent metal cation used, based on the water-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophosphite, salts of sulfinic acids, for example the disodium salt of 2-hydroxy-2-sulfinatoacetic acid, and addition products of aldehydes, for example the disodium salt of 2-hydroxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggolite Chemicals; Heilbronn; Germany). Also useful is the purified 2-hydroxy-2-sulfonatoacetic acid and its sodium salts, available under the trade name Blancolen® from the same company.

The reducing agents are typically used in the form of a solution in a suitable solvent, preferably water. The reducing agent may be used as a pure substance or any mixture of the above reducing agents may be used.

When the water-absorbent polymer particles are coated with a reducing agent, the amount of reducing agent used, based on the water-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol, mannitol, inositol, pentaerythritol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the water-absorbent polymer particles only insignificantly. The polyols are preferably used as a solution in aqueous or water-miscible solvents.

The polyol can be added before, during, or after surface-crosslinking. Preferably it is added after surface-cross linking. Any mixture of the above listed poyols may be used.

When the water-absorbent polymer particles are coated with a polyol, the use amount of polyol, based on the water-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (GebrOder Ruberg GmbH & Co KG, Nieheim, Germany). Moreover, it is also possible to use a fluidized bed for mixing.

Agglomeration

The water-absorbent polymer particles can further selectively be agglomerated. The agglomeration can take place after the polymerization, the thermal postreatment, the thermal surface-postcrosslinking or the coating.

Useful agglomeration assistants include water and water-miscible organic solvents, such as alcohols, tetrahydrofuran and acetone; water-soluble polymers can be used in addition.

For agglomeration a solution comprising the agglomeration assistant is sprayed onto the water-absorbing polymeric particles. The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

Combination of Thermal Posttreatment, Surface-Postcrosslinking and Optionally Coating It is preferred that the steps of thermal posttreatment and thermal surface-postcrosslinking are combined in one process step. Such combination allows the use of low cost equipment and moreover the process can be run at low temperatures, that is cost-efficient and avoids discoloration and loss of performance properties of the finished product by thermal degradation.

The mixer may be selected from any of the equipment options cited in the thermal posttreatment section. Ruberg continuous flow mixers, Becker shovel mixers and Pflugschar® plowshare mixers are preferred.

It is particular preferred that the surface-postcrosslinking solution is sprayed onto the water-absorbent polymer particles under agitation.

Following the thermal posttreatment/surface-postcrosslinking the water-absorbent polymer particles are dried to the desired moisture level and for this step any dryer cited in the surface-postcrosslinking section may be selected. However, as only drying needs to be accomplished in this particular preferred embodiment it is possible to use simple and low cost heated contact dryers like a heated screw dryer, for example a Holo-Flite® dryer (Metso Minerals Industries Inc.; Danville; U.S.A.). Alternatively a fluidized bed may be used. In cases where the product needs to be dried with a predetermined and narrow residence time it is possible to use torus disc dryers or paddle dryers, for example a Nara paddle dryer (NARA Machinery Europe; Frechen; Germany).

In a preferred embodiment of the present invention, polyvalent cations cited in the surface-postcrosslinking section are applied to the particle surface before, during or after addition of the surface-postcrosslinker by using different addition points along the axis of a horizontal mixer.

It is very particular preferred that the steps of thermal post-treatment, surface-postcrosslinking, and coating are combined in one process step. Suitable coatings are cationic polymers, surfactants, and inorganic inert substances that are cited in the coating section. The coating agent can be applied to the particle surface before, during or after addition of the surface-postcrosslinker also by using different addition points along the axis of a horizontal mixer.

The polyvalent cations and/or the cationic polymers can act as additional scavengers for residual surface-postcrosslinkers. It is preferred that the surface-postcrosslinkers are added prior to the polyvalent cations and/or the cationic polymers to allow the surface-postcrosslinker to react first.

The surfactants and/or the inorganic inert substances can be used to avoid sticking or caking during this process step under humid atmospheric conditions. Preferred surfactants are nonionic and amphoteric surfactants. Preferred inorganic inert substances are precipitated silicas and fumed silicas in form of powder or dispersion.

The amount of total liquid used for preparing the solutions/dispersions is typically from 0.01% to 25% by weight, preferably from 0.5% to 12% by weight, more preferably from 2% to 7% by weight, most preferably from 3% to 6% by weight, in respect to the weight amount of water-absorbent polymer particles to be processed.

Preferred embodiments are depicted in FIGS. 1 to 16.

FIG. 1: Process scheme

Figure 2:
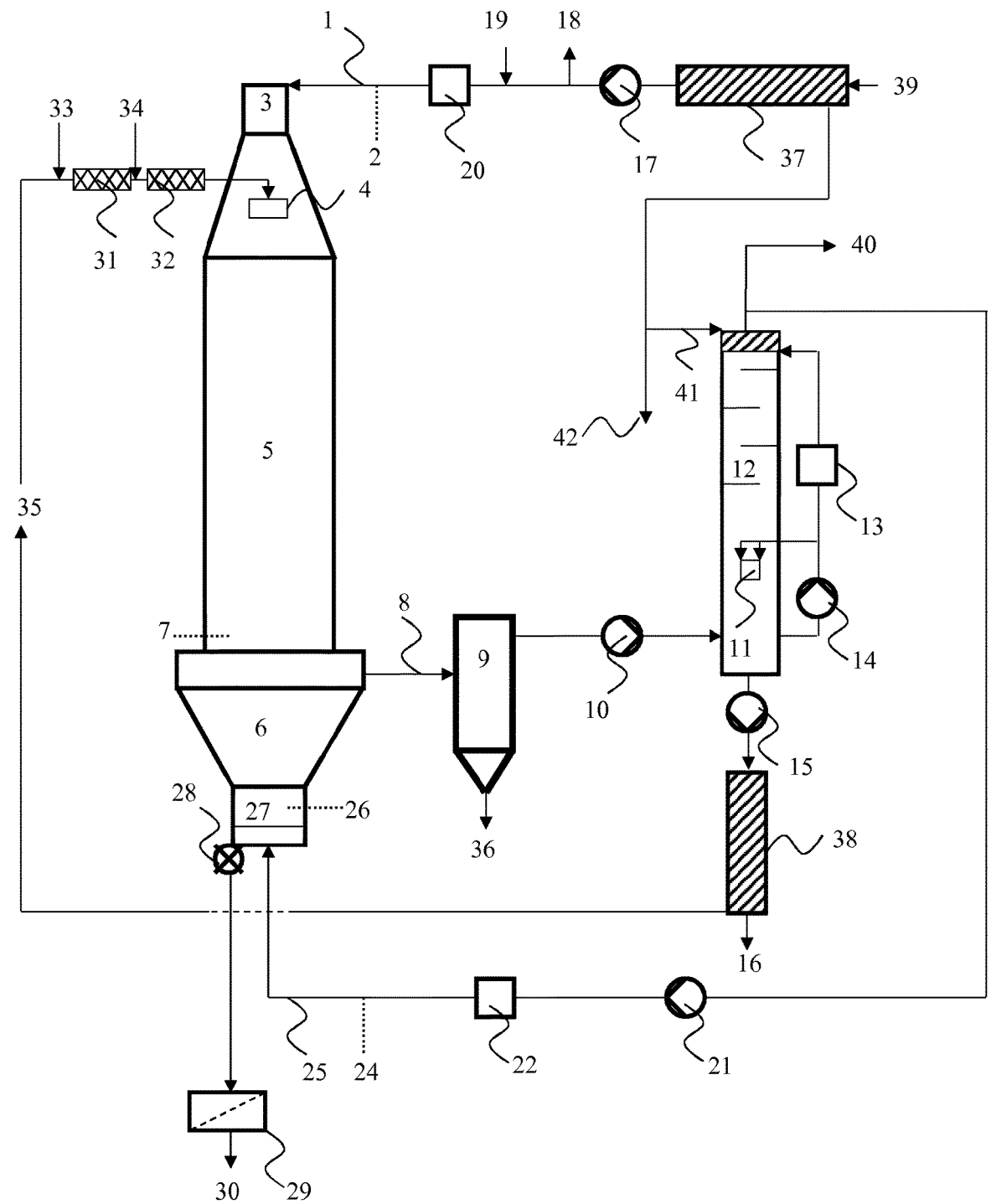

FIG. 2: Process scheme using dry air

Figure 3:
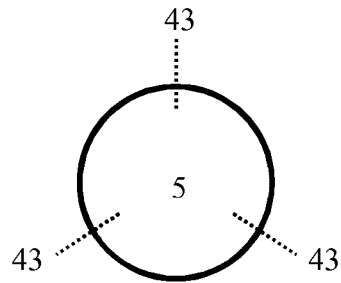

FIG. 3: Arrangement of the T_outlet measurement

Figure 4:
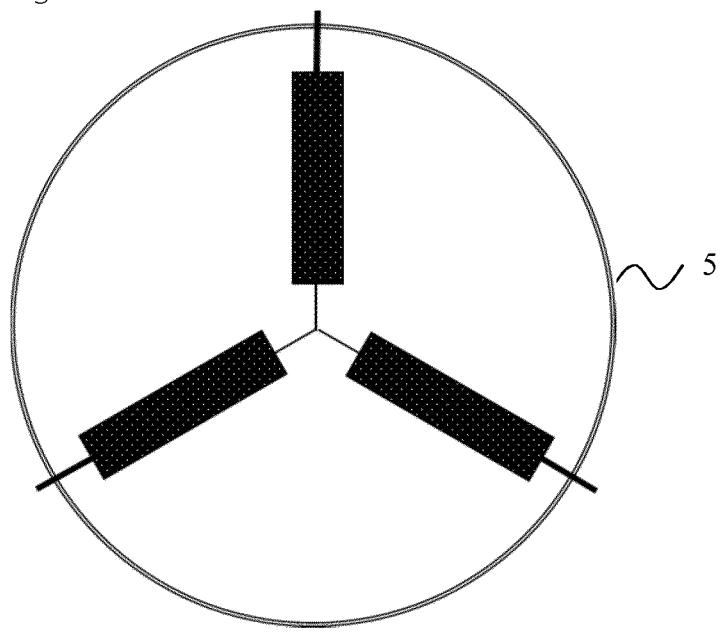

FIG. 4: Arrangement of the dropletizer units with 3 droplet plates

Figure 5:
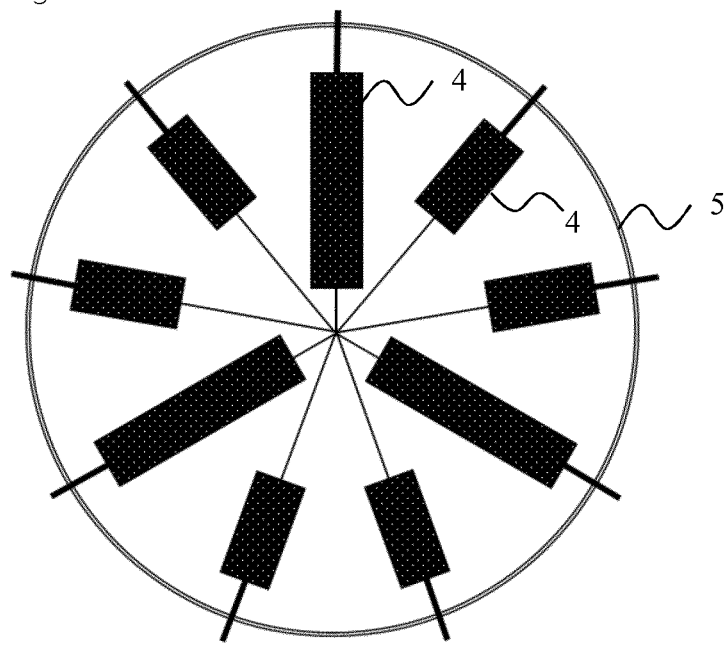

FIG. 5: Arrangement of the dropletizer units with 9 droplet plates

Figure 6:
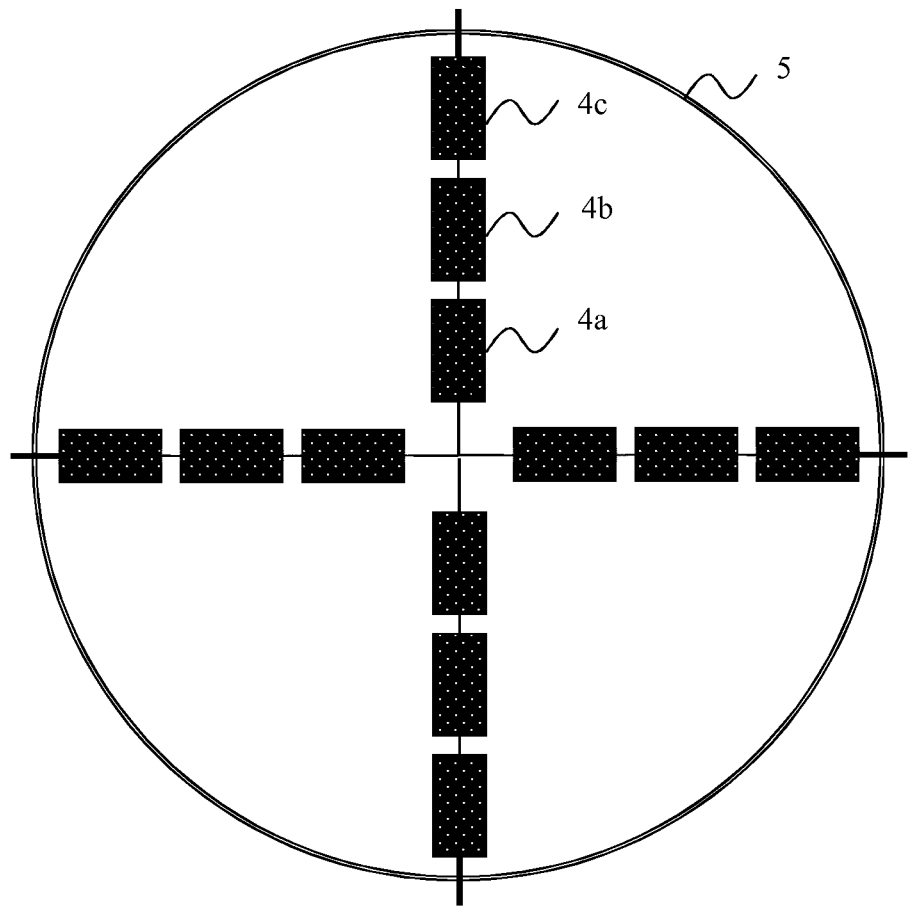

FIG. 6: Arrangement of the dropletizer units with 9 droplet plates

Figure 7:
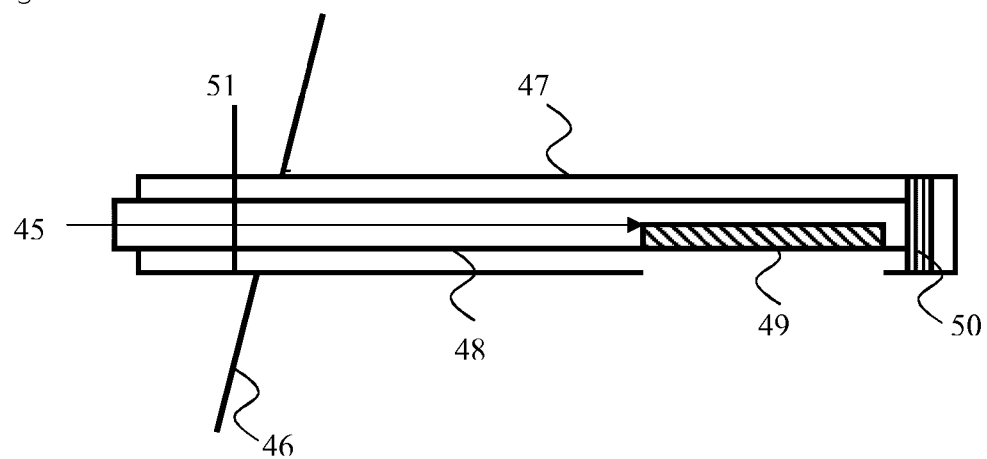

FIG. 7: Dropletizer unit (longitudinal cut)

Figure 8:
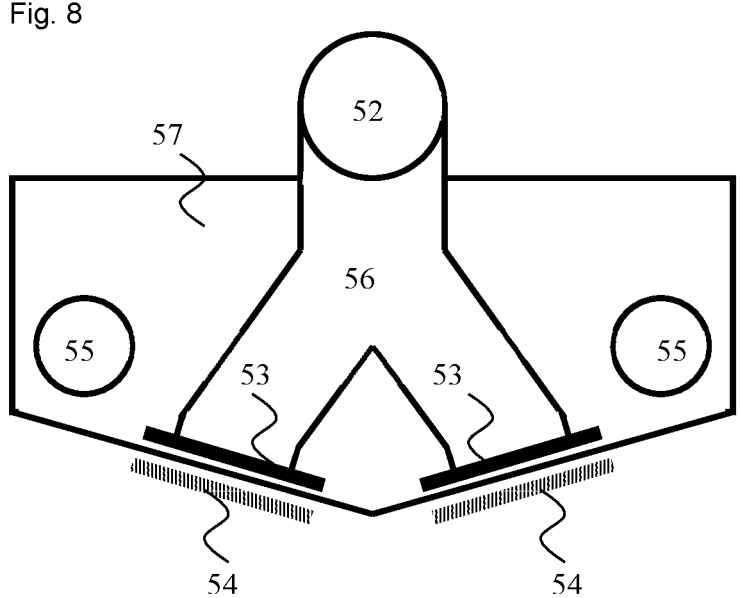

FIG. 8: Dropletizer unit (cross sectional view)

Figure 9:
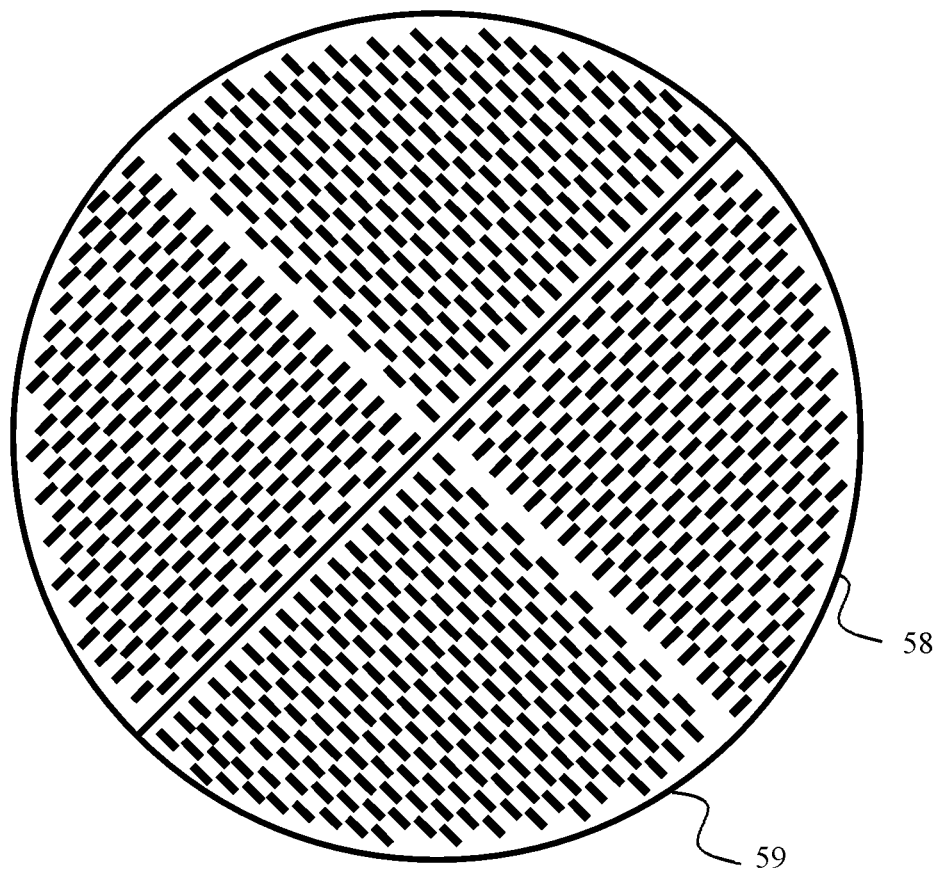

FIG. 9: Bottom of the internal fluidized bed (top view)

Figure 10:
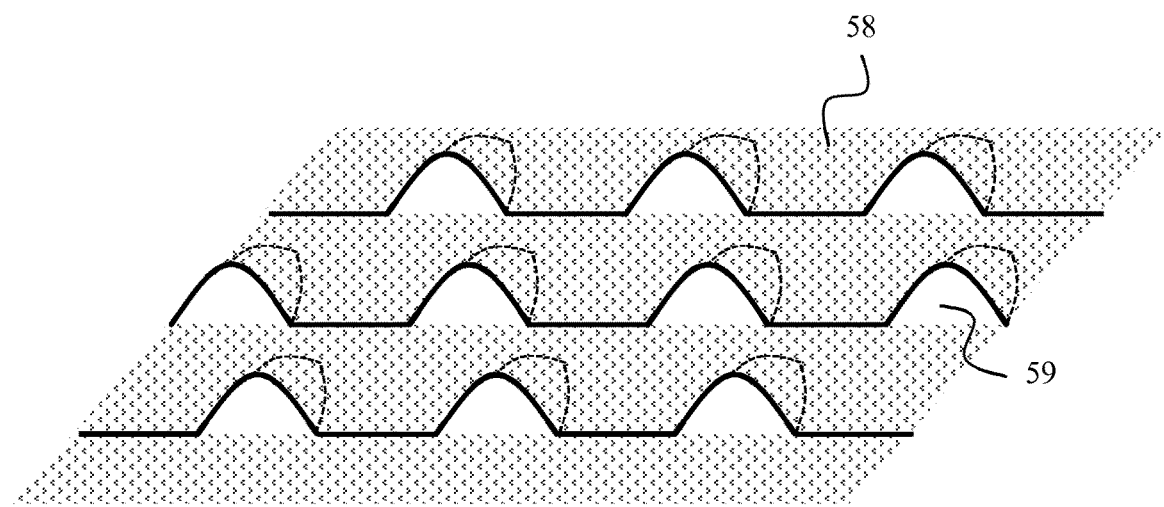

FIG. 10: openings in the bottom of the internal fluidized bed

Figure 11:
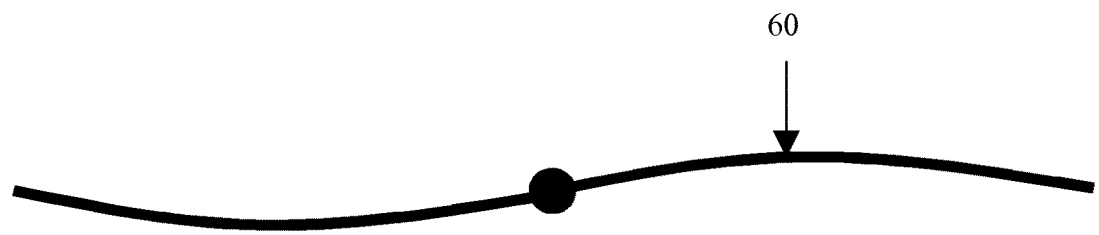

FIG. 11: Rake stirrer for the intern fluidized bed (top view)

Figure 12:
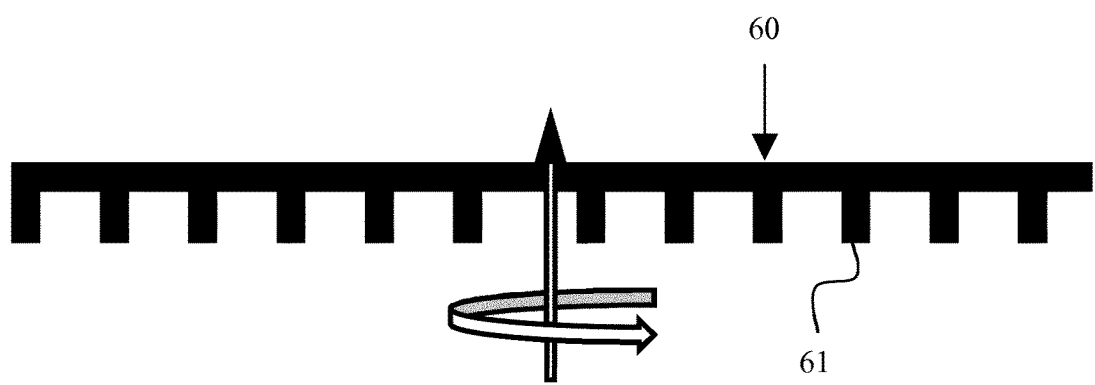

FIG. 12: Rake stirrer for the intern fluidized bed (cross sectional view)

Figure 13:
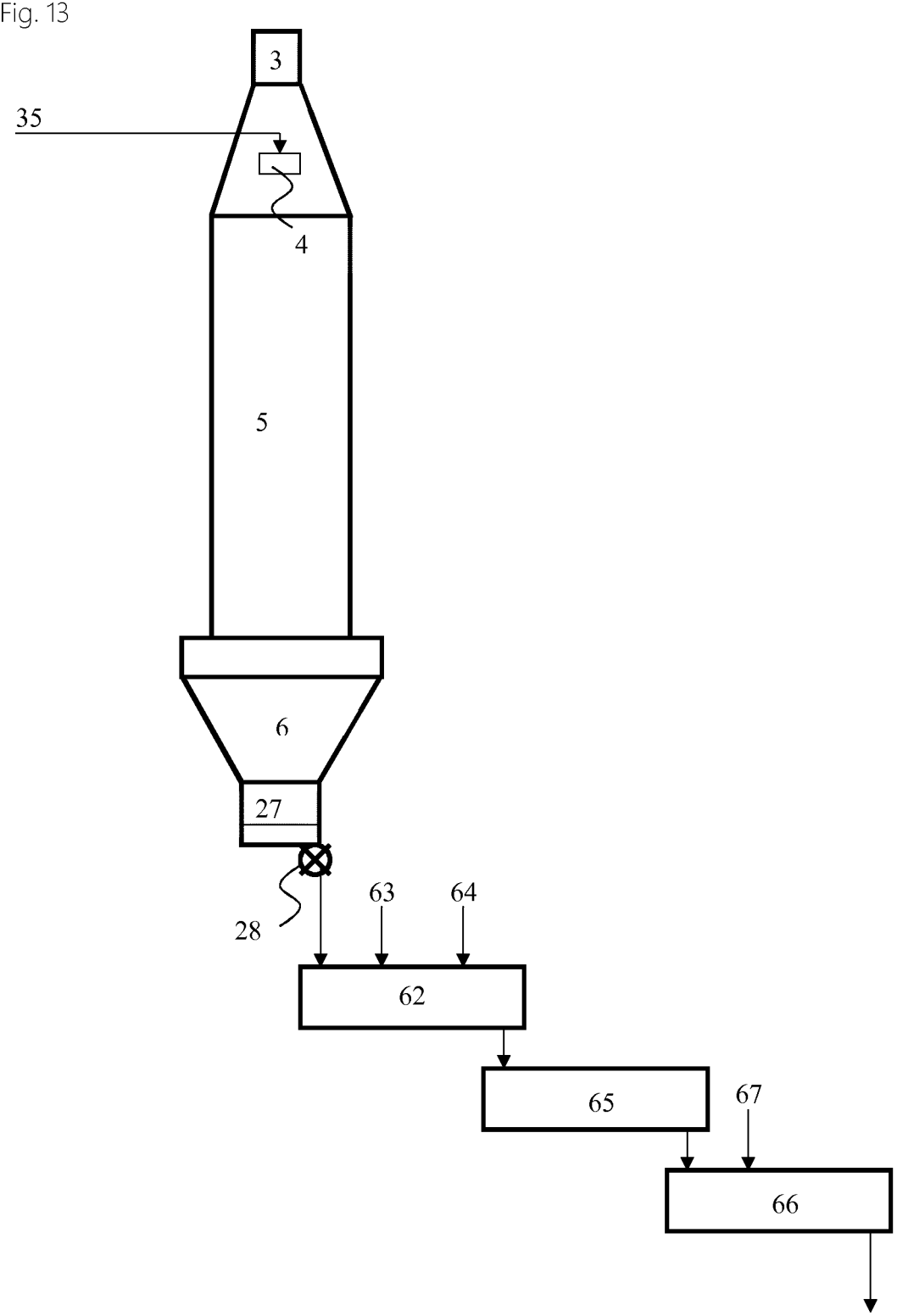

FIG. 13: Process scheme (surface-postcrosslinking)

Figure 14:
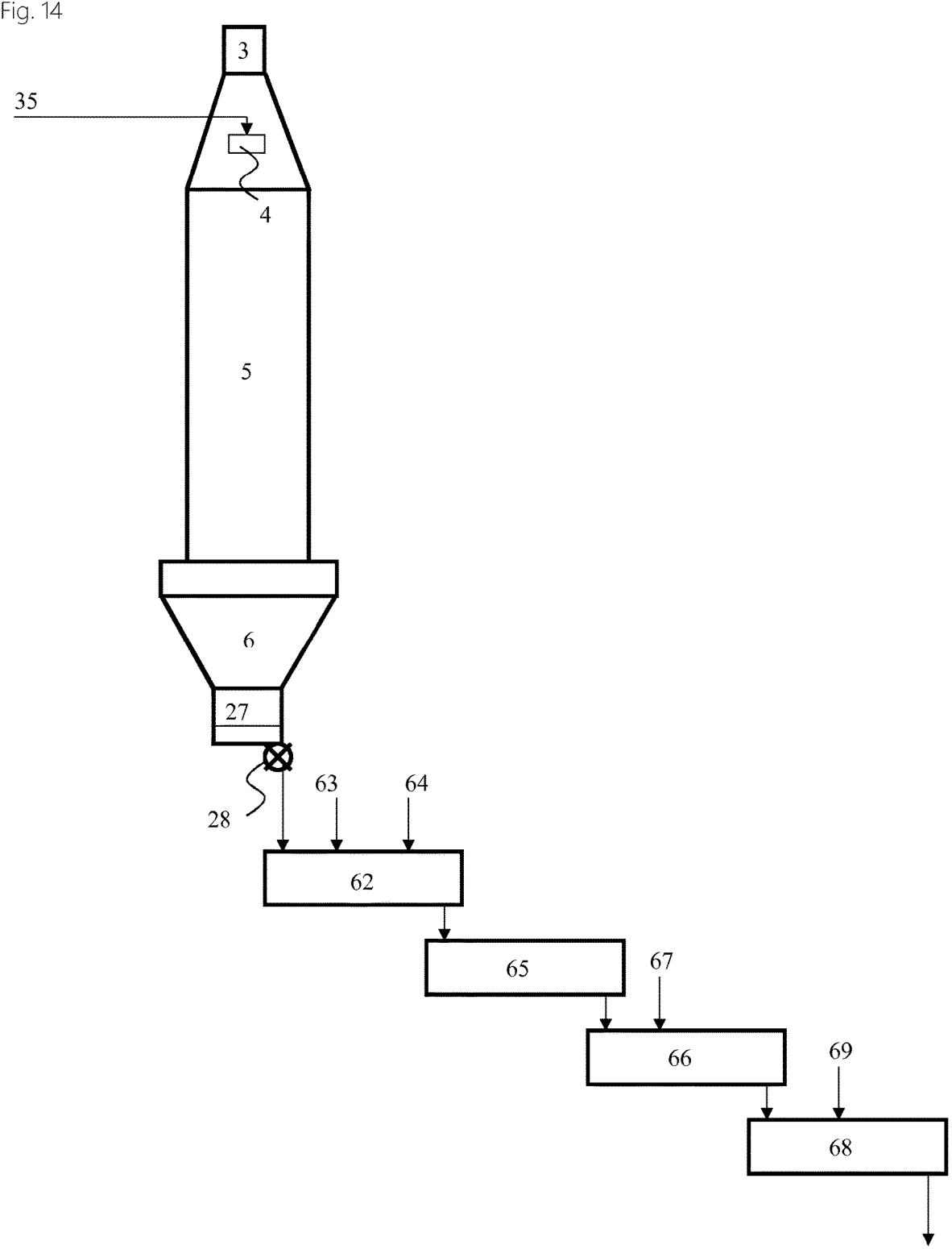

FIG. 14: Process scheme (surface-postcrosslinking and coating)

Figure 15:
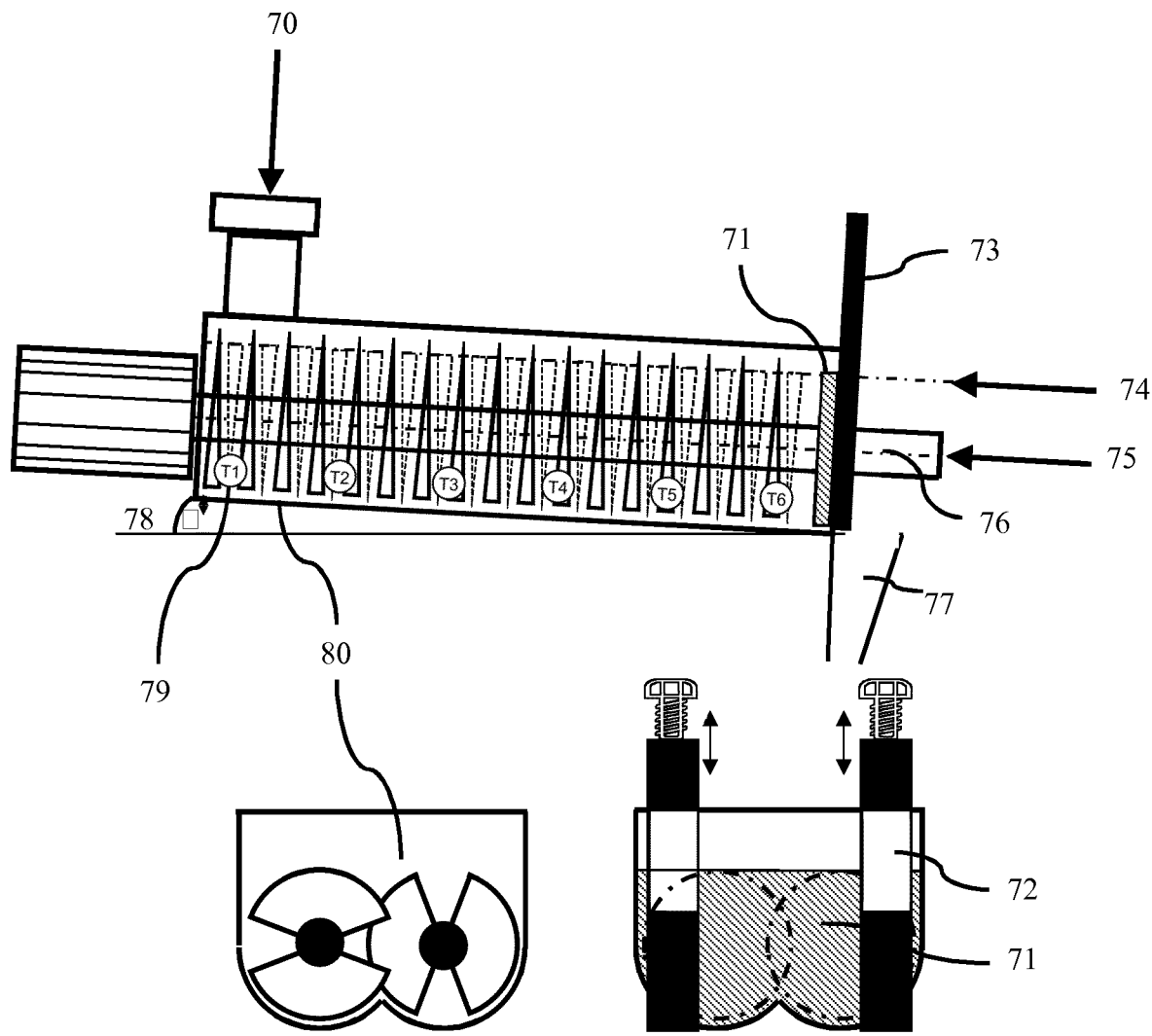

FIG. 15: Contact dryer for surface-postcrosslinking

Figure 16:
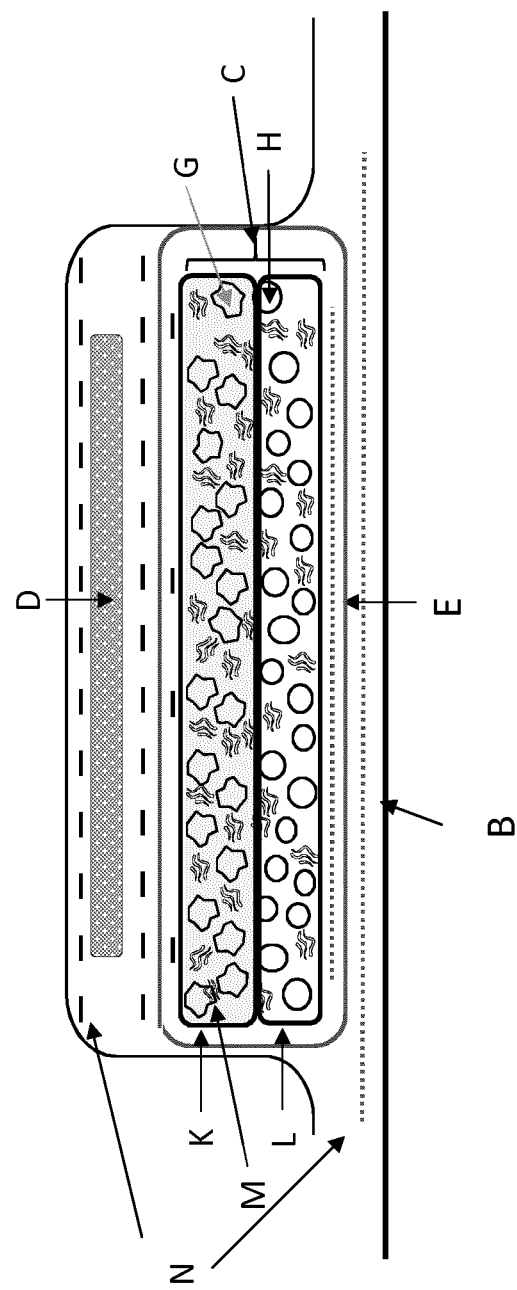

FIG. 16: Schematic view of a fluid absorbent article

The reference numerals have the following meanings:

1 Drying gas inlet pipe
2 Drying gas amount measurement
3 Gas distributor
4 Dropletizer unit(s)
4a Dropletizer unit
4b Dropletizer unit
4c Dropletizer unit
5 Reaction zone (cylindrical part of the spray dryer)
6 Cone
7 T_outlet measurement
8 Tower offgas pipe
9 Dust separation unit
10 Ventilator
11 Quench nozzles
12 Condenser column, counter current cooling
13 Heat exchanger
14 Pump
15 Pump
16 Water outlet
17 Ventilator
18 Offgas outlet
19 Nitrogen inlet
20 Heat exchanger
21 Ventilator
22 Heat exchanger
24 Water loading measurement
25 Conditioned internal fluidized bed gas
26 Internal fluidized bed product temperature measurement
27 Internal fluidized bed
28 Rotary valve
29 Sieve
30 End product
31 Static mixer
32 Static mixer
33 Initiator feed
34 Initiator feed
35 Monomer feed
36 Fine particle fraction outlet to rework
37 Gas drying unit
38 Monomer separator unit
39 Gas inlet pipe
40 Gas outlet pipe
41 Water outlet from the gas drying unit to condenser column
42 Waste water outlet
43 T_outlet measurement (average temperature out of 3 measurements around tower circumference)
45 Monomer premixed with initiator feed
46 Spray dryer tower wall
47 Dropletizer unit outer pipe
48 Dropletizer unit inner pipe
49 Dropletizer cassette
50 Teflon block
51 Valve
52 Monomer premixed with initiator feed inlet pipe connector
53 Droplet plate
54 Counter plate
55 Flow channels for temperature control water
56 Dead volume free flow channel for monomer solution
57 Dropletizer cassette stainless steel block
58 Bottom of the internal fluidized bed with four segments
59 Split openings of the segments
60 Rake stirrer
61 Prongs of the rake stirrer
62 Mixer
63 Optional coating feed
64 Postcrosslinker feed
65 Thermal dryer (surface-postcrosslinking)
66 Cooler
67 Optional coating/water feed
68 Coater
69 Coating/water feed
70 Base polymer feed
71 Discharge zone
72 Weir opening
73 Weir plate
74 Weir height 100%
75 Weir height 50%
76 Shaft
77 Discharge cone
78 Inclination angle α
79 Temperature sensors ($T_1$ to $T_6$)
80 Paddle (shaft offset 90°)

The drying gas is fed via a gas distributor (3) at the top of the spray dryer as shown in FIG. 1.

The drying gas is partly recycled (drying gas loop) via a baghouse filter or cyclone unit (9) and a condenser column (12). The pressure inside the spray dryer is below ambient pressure.

The spray dryer outlet temperature is preferably measured at three points around the circumference at the end of the cylindrical part as shown in FIG. 3. The single measurements (43) are used to calculate the average cylindrical spray dryer outlet temperature.

In one preferred embodiment a monomer separator unit (38) is used for recycling of the monomers from the condenser column (12) into the monomer feed (35). This monomer separator unit is for example especially a combination of micro-, ultra-, nanofiltration and osmose membrane units, to separate the monomer from water and polymer particles. Suitable membrane separator systems are described, for example, in the monograph "Membranen: Grundlagen, Verfahren und Industrielle Anwendungen", K. Ohlrogge and K. Ebert, Wiley-VCH, 2012 (ISBN: 978-3-527-66033-9).

The product accumulated in the internal fluidized bed (27). Conditioned internal fluidized bed gas is fed to the internal fluidized bed (27) via line (25). The relative humidity of the internal fluidized bed gas is preferably controlled by the temperature in the condensor column (12) and using the Mollier diagram.

The spray dryer offgas is filtered in a dust separation unit (9) and sent to a condenser column (12) for quenching/cooling. After dust separation (9) a recuperation heat exchanger system for preheating the gas after the condenser column (12) can be used. The dust separation unit (9) may be heat-traced on a temperature of preferably from 80 to 180° C., more preferably from 90 to 150° C., most preferably from 100 to 140° C.

Example for the dust separation unit are baghouse filter, membranes, cyclones, dust compactors and for examples described, for example, in the monographs "Staubabscheiden", F. Löffler, Georg Thieme Verlag, Stuttgart, 1988 (ISBN 978-3137122012) and "Staubabscheidung mit Schlauchfiltern und Taschenfiltern", F. Löffler, H. Dietrich and W. Flatt, Vieweg, Braunschweig, 1991 (ISBN 978-3540670629).

Most preferable are cyclones, for example, cyclones/centrifugal separators of the types ZSA/ZSB/ZSC from LTG Aktiengesellschaft and cyclone separators from Ventilatorenfabrik Oelde GmbH, Camfil Farr International and MikroPul GmbH.

Excess water is pumped out of the condenser column (12) by controlling the (constant) filling level in the condenser column (12). The water in the condenser column (12) is pumped counter-current to the gas via quench nozzles (11) and cooled by a heat exchanger (13) so that the temperature in the condenser column (12) is preferably from 40 to 71° C., more preferably from 46 to 69° C., most preferably from 49 to 65° C. and more even preferably from 51 to 60° C. The water in the condenser column (12) is set to an alkaline pH by dosing a neutralizing agent to wash out vapors of monomer a). Aqueous solution from the condenser column (12) can be sent back for preparation of the monomer solution.

The condenser column offgas may be split to the gas drying unit (37) and the conditioned internal fluidized bed gas (27).

The principle of a gas drying unit is described in the monograph "Leitfaden for Lüftungsund Klimaanlagen—Grundlagen der Thermodynamik Komponenten einer Vollklimaanlage Normen und Vorschriften", L. Keller, Oldenbourg Industrieverlag, 2009 (ISBN 978-3835631656).

As gas drying unit can be used, for example, an air gas cooling system in combination with a gas mist eliminators or droplet separator (demister), for examples, droplet vane type separator for horizontal flow (e.g. type DH 5000 from Munters AB, Sweden) or vertical flow (e.g. type DV 270 from Munters AB, Sweden). Vane type demisters remove liquid droplets from continuous gas flows by inertial impaction. As the gas carrying entrained liquid droplets moves through the sinusoidal path of a vane, the higher density liquid droplets cannot follow and as a result, at every turn of the vane blades, these liquid droplets impinge on the vane surface.

Most of the droplets adhere to the vane wall. When a droplet impinges on the vane blade at the same location, coalescence occurs. The coalesced droplets then drain down due to gravity.

As air gas cooling system, any gas/gas or gas/liquid heat exchanger can be used. Preferred are sealed plate heat exchangers.

In one embodiment dry air can be used as feed for the gas distributor (3). If air used as gas, then air can be transported via air inlet pipe (39) and can be dried in the gas drying unit (37), as described before. After the condenser column (12), the air, which not used for the internal fluidized bed is transported via the outlet pipe outside (40) of the plant as shown in FIG. 2.

The water, which is condensed in the gas drying unit (37) can be partially used as wash water for the condenser column (12) or disposed.

The gas temperatures are controlled via heat exchangers (20) and (22). The hot drying gas is fed to the cocurrent spray dryer via gas distributor (3). The gas distributor (3) consists preferably of a set of plates providing a pressure drop of preferably 1 to 100 mbar, more preferably 2 to 30 mbar, most preferably 4 to 20 mbar, depending on the drying gas amount. Turbulences and/or a centrifugal velocity can also be introduced into the drying gas if desired by using gas nozzles or baffle plates.

Conditioned internal fluidized bed gas is fed to the internal fluidized bed (27) via line (25). The steam content of the fluidized bed gas can be controlled by the temperature in the condenser column (12). The product holdup in the internal fluidized bed (27) can be controlled via rotational speed of the rotary valve (28).

The amount of gas in the internal fluidized bed (27) is selected so that the particles move free and turbulent in the internal fluidized bed (27). The product height in the internal fluidized bed (27) is with gas preferably at least 10%, more preferably at least 20%, more preferably at least 30%, even more preferably at least 40% higher than without gas.

The product is discharged from the internal fluidized bed (27) via rotary valve (28). The product holdup in the internal fluidized bed (27) can be controlled via rotational speed of the rotary valve (28). The sieve (29) is used for sieving off overs/lumps.

The monomer solution is preferably prepared by mixing first monomer a) with a neutralization agent and secondly with crosslinker b). The temperature during neutralization is controlled to preferably from 5 to 60° C., more preferably from 8 to 40° C., most preferably from 10 to 30° C., by using a heat exchanger and pumping in a loop. A filter unit is preferably used in the loop after the pump. The initiators are metered into the monomer solution upstream of the dropletizer by means of static mixers (31) and (32) via lines (33) and (34) as shown in FIG. 1 and FIG. 2. Preferably a peroxide solution having a temperature of preferably from 5 to 60° C., more preferably from 10 to 50° C., most preferably from 15 to 40° C., is added via line (33) and preferably an azo initiator solution having a temperature of preferably from 2 to 30° C., more preferably from 3 to 15° C., most preferably from 4 to 8° C., is added via line (34). Each initiator is preferably pumped in a loop and dosed via control valves to each dropletizer unit. A second filter unit is preferably used after the static mixer (32). The mean residence time of the monomer solution admixed with the full initiator package in the piping before dropletization is preferably less than 60 s, more preferably less than 30 s, most preferably less than 10 s.

For dosing the monomer solution into the top of the spray dryer preferably three dropletizer units are used as shown in FIG. 4. However, any number of dropletizers can be used that is required to optimize the throughput of the process and the quality of the product. Hence, in the present invention at least one dropletizer is employed, and as many dropletizers as geometrically allowed may be used.

A dropletizer unit consists of an outer pipe (47) having an opening for the dropletizer cassette (49) as shown in FIG. 7. The dropletizer cassette (49) is connected with an inner pipe (48). The inner pipe (48) having a PTFE block (50) at the end as sealing can be pushed in and out of the outer pipe (51) during operation of the process for maintenance purposes.

The temperature of the dropletizer cassette (57) is controlled to preferably 5 to 80° C., more preferably 10 to 70° C., most preferably 30 to 60° C., by water in flow channels (55) as shown in FIG. 8.

The dropletizer cassette has preferably from 10 to 2000 bores, more preferably from 50 to 1500 bores, most preferably from 100 to 1000 bores. The diameter of the bores size area is 1900 to 22300 $\mu m^2$, more preferably from 7800 to 20100 $\mu m^2$, most preferably from 11300 to 17700 $\mu m^2$. The bores can be of circular, rectangular, triangular or any other shape. Circular bores are preferred with a bore size from 50 to 170 µm, more preferably from 100 to 160 µm, most preferably from 120 to 150 µm. The ratio of bore length to bore diameter is preferably from 0.5 to 10, more preferably from 0.8 to 5, most preferably from 1 to 3. The droplet plate (53) can have a greater thickness than the bore length when using an inlet bore channel. The droplet plate (53) is preferably long and narrow as disclosed in WO 2008/

086976 A1. Multiple rows of bores per droplet plate can be used, preferably from 1 to 20 rows, more preferably from 2 to 5 rows.

The dropletizer cassette (57) consists of a flow channel (56) having essential no stagnant volume for homogeneous distribution of the premixed monomer and initiator solutions and two droplet plates (53). The droplet plates (53) have an angled configuration with an angle of preferably from 1 to 90°, more preferably from 3 to 45°, most preferably from 5 to 20°. Each droplet plate (53) is preferably made of a heat and/or chemically resistant material, such as stainless steel, polyether ether ketone, polycarbonate, polyarylsulfone, such as polysulfone, or polyphenylsulfone, or fluorous polymers, such as perfluoroalkoxyethylene, polytetrafluoroethylene, polyvinylidenfluorid, ethylene-chlorotrifluoroethylene copolymers, ethylene-tetrafluoroethylene copolymers and fluorinated polyethylene. Coated droplet plates as disclosed in WO 2007/031441 A1 can also be used. The choice of material for the droplet plate is not limited except that droplet formation must work and it is preferable to use materials which do not catalyze the start of polymerization on its surface.

The arrangement of dropletizer cassettes is preferably rotationally symmetric or evenly distributed in the spray dryer (for example see FIG. 3 to 5).

In a preferred embodiment the angle configuration of the droplet plate (53) is in the middle lower then outside, for example: 4a=3°, 4b=5° and 4c=8° (FIG. 5).

The throughput of monomer including initiator solutions per dropletizer unit is preferably from 10 to 4000 kg/h, more preferably from 100 to 1000 kg/h, most preferably from 200 to 600 kg/h. The throughput per bore is preferably from 0.1 to 10 kg/h, more preferably from 0.5 to 5 kg/h, most preferably from 0.7 to 2 kg/h.

The start-up of the cocurrent spray dryer (5) can be done in the following sequence:
  starting the condenser column (12),
  starting the ventilators (10) and (17),
  starting the heat exchanger (20),
  heating up the drying gas loop up to 95° C.,
  starting the nitrogen feed via the nitrogen inlet (19),
  waiting until the residual oxygen is below 4% by weight,
  heating up the drying gas loop,
  at a temperature of 105° C. starting the water feed (not shown) and
  at target temperature stopping the water feed and starting the monomer feed via dropletizer unit (4)

The shut-down of the cocurrent spray dryer (5) can be done in the following sequence:
  stopping the monomer feed and starting the water feed (not shown),
  shut-down of the heat exchanger (20),
  cooling the drying gas loop via heat exchanger (13),
  at a temperature of 105° C. stopping the water feed,
  at a temperature of 60° C. stopping the nitrogen feed via the nitrogen inlet (19) and
  feeding air into the drying gas loop (not shown)

To prevent damages the cocurrent spray dryer (5) must be heated up and cooled down very carefully. Any quick temperature change must be avoided.

The openings in the bottom of the internal fluidized bed may be arranged in a way that the water-absorbent polymer particles flow in a cycle as shown in FIG. 9. The bottom shown in FIG. 9 comprises of four segments (58). The openings (59) in the segments (58) are in the shape of slits that guides the passing gas stream into the direction of the next segment (58). FIG. 10 shows an enlarged view of the openings (59).

The opening may have the shape of holes or slits. The diameter of the holes is preferred from 0.1 to 10 mm, more preferred from 0.2 to 5 mm, most preferred from 0.5 to 2 mm. The slits have a length of preferred from 1 to 100 mm, more preferred from 2 to 20 mm, most preferred from 5 to 10 mm, and a width of preferred from 0.5 to 20 mm, more preferred from 1 to 10 mm, most preferred from 2 to 5 mm.

FIG. 11 and FIG. 12 show a rake stirrer (60) that may be used in the internal fluidized bed. The prongs (61) of the rake have a staggered arrangement. The speed of rake stirrer is preferably from 0.5 to 20 rpm, more preferably from 1 to 10 rpm most preferably from 2 to 5 rpm.

For start-up the internal fluidized bed may be filled with a layer of water-absorbent polymer particles, preferably 5 to 50 cm, more preferably from 10 to 40 cm, most preferably from 15 to 30 cm.

The surface-postcrosslinked water-absorbent polymer particles obtained by droplet polymerization preferably having a mean sphericity or roundness from 0.80 to 0.95, preferably from 0.82 to 0.93, more preferably from 0.84 to 0.91, most preferably from 0.85 to 0.90. The sphericity (SPHT) is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technolgy GmbH; Haan; Germany): For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. To record the particles, the so-called CCD-zoom camera (CAM-Z) is used. To control the metering channel, a surface coverage fraction in the detection window of the camera (transmission) of 0.5% is predefined.

In the context of this invention "sphericity" means "mean sphericity" or in particular "mean volume-weighted sphericity" Fluid-absorbent particles suitable for the first type (G) of fluid-absorbent particles useful for present invention preferably have a centrifuge retention capacity of at least 25 g/g, preferably at least 30 g/g and a SFC of at least $20\times10^{-7}$ cm$^3$·s/g, preferably at least $30\times10^{-7}$-cm$^3$·s/g.

As the centrifuge retention capacity (CRC) is the maximum liquid retention capacity of the surface-postcrosslinked water-absorbent polymer particles it is of interest to maximize this parameter. However the absorption under high load (AUHL) is important to allow the fiber-matrix in a hygiene article to open up pores during swelling to allow further liquid to pass easily through the article structure to enable rapid uptake of this liquid.

The SFC is a measure of the permeability. Increased permeability usually results in a loss of absorption capacity of the fluid-absorbent polymers.

Fluid-absorbent particles suitable for the second type (H) of fluid-absorbent particles useful for present invention preferably have a centrifuge retention capacity of at least 30 g/g, preferably 35 g/g, more preferably 40 g/g.

Fluid-absorbent particles also suitable for the second type (H) of water-absorbent polymer particles (H) having a sphericity of at least 0.80, preferably of at least 0.85, particularly preferred of at least 0.90.

The SFC of the first type of water-absorbent polymer particles (G) is at least $20 \times 10^{-7}$ cm$^3$·s/g, more preferably at least $25 \times 10^{-7}$ cm$^3$·s/g, particularly preferred at least $30 \times 10^{-7}$ cm$^3$·s/g, preferentially at least $40 \times 10^{-7}$ cm$^3$·s/g, more preferably at least $60 \times 10^{-7}$ cm$^3$·s/g, most preferably at least $80 \times 10^{-7}$ cm$^3$·s/g, further most preferably of at least $100 \times 10^{-7}$ cm$^3$·s/g, but not above $200 \times 10^{-7}$ cm$^3$·s/g The SFC of the second type of fluid-absorbent polymer particles (H) is at maximum of $15 \times 10^{-7}$ cm$^3$·s/g, preferably of at maximum of $10 \times 10^{-7}$ cm$^3$·s/g, particularly preferred of at maximum of $5 \times 10^{-7}$ cm$^3$·s/g, more preferably of $3 \times 10^{-7}$ cm$^3$·s/g, most preferably of $0 \times 10^{-7}$ cm$^3$·s/g.

The bulk density of the fluid-absorbent polymer particles is preferably from 0.6 to 0.75 g/cm$^3$ for the first type (G) of fluid-absorbent polymer particles, preferably from 0.62 to 0.68 g/cm$^3$, Preferably 0.62 to 1 g/cm$^3$, more preferably from 0.7 to 0.9 g/cm$^3$ for the second type (H) of fluid absorbent polymer particles.

Generally the suited water-absorbent polymer particles have an absorbency under high load (AUHL) of at least 10 g/g, preferably of at least 15 g/g.

For the second type of water-absorbent polymer particles (H) it is preferred having an AUHL of at least 15 g/g.

Furthermore the water-absorbent polymer particles have a level of extractable constituents of less than 10% by weight, preferably less than 9% by weight, more preferably less than 8% by weight, most preferably less than 6% by weight.

The average particle diameter of the water-absorbent particles useful for the present invention is preferably from 200 to 550 μm, more preferably from 250 to 500 μm, most preferably from 350 to 450 μm.

According to one embodiment of the invention at least two types of water-absorbent polymer particles are mixed.

According to the invention the mixture of water-absorbent polymer particles comprises at least a first type of water-absorbent polymer particles (G) and at least a second type of water-absorbent polymer particles (H);
wherein the first type of water absorbent polymer particles (G) of the fluid-absorbent core (C) have a SFC of at least $20 \times 10^{-7}$ cm$^3$·s/g and wherein the at least second type of water-absorbent polymer particles (H) of the fluid-absorbent core have a sphericity of at least 0.80.

An embodiment of the inventive mixture, wherein the at least first type of water-absorbent polymer particles (G) is present of at least 30% by weight, preferably of at least 33% by weight within the fluid-absorbent core (C) based on the sum of water-absorbent polymer particles (G, H).

Another embodiment of the inventive mixture, wherein the at least first type of water-absorbent polymer particles (G) is present of at least 50% by weight within the fluid-absorbent core (C) based on the sum of water-absorbent polymer particles (G, H).

An embodiment of the inventive mixture, wherein the at least first type of water-absorbent polymer particles (G) is present of at maximum 66% by weight, preferably of at maximum 70% by weight within the fluid-absorbent core (C) based on the sum of water-absorbent polymer particles (G, H) According to the invention the mixture of at least a first type of water-absorbent polymer particles (G) and at least a second type of water-absorbent polymer particles (H) comprises at least 30% by weight, preferably least 33% by weight of the first type of water-absorbent polymer particles (G) and at maximum 66% by weight, preferably at maximum 70% by weight of the second type of water-absorbent polymer particles (H) based on the sum of water-absorbent polymer particles (G, H).

According to the invention the mixture of at least a first type of water-absorbent polymer particles (G) and at least a second type of water-absorbent polymer particles (H) comprises at least 50% by weight of the first type of water-absorbent polymer particles (G) and at maximum 50% by weight of the second type of water-absorbent polymer particles (H) based on the sum of water-absorbent polymer particles (G, H).

According to the invention the mixture of at least a first type of water-absorbent polymer particles (G) and at least a second type of water-absorbent polymer particles (H) comprises at maximum 66% by weight, preferably at maximum 70% by weight of the first type of water-absorbent polymer particles (G) and at least 30% by weight, preferably at least 33% by weight of the second type of water-absorbent polymer particles (H) based on the sum of water-absorbent polymer particles (G, H).

The mixture according to the invention, wherein the first type of water-absorbent polymer particles (G) preferably have an SFC of at least $20 \times 10^{-7}$ cm$^3$·s/g, preferably of at least $25 \times 10^{-7}$ cm$^3$·s/g, more preferably of at least $30 \times 10^{-7}$ cm$^3$·s/g, preferentially of at least $40 \times 10^{-7}$ cm$^3$·s/g, more preferably of at least $60 \times 10^{-7}$ cm$^3$·s/g, most preferably of at least $80 \times 10^{-7}$ cm$^3$·s/g, further most preferably of at least $100 \times 10^{-7}$ cm$^3$·s/g, but not above $200 \times 10^{-7}$ cm$^3$·s/g According to the invention the second type of water-absorbent polymer particles (H) having a sphericity of at least 0.80, preferably of at least 0.85, particularly preferred of at least 0.90.

The second type of water-absorbent polymer particles (H) furthermore preferably have an SFC of at maximum of $15 \times 10^{-7}$ cm$^3$·s/g, preferably of at maximum of $10 \times 10^{-7}$ cm$^3$·s/g, particularly preferred of at maximum of $5 \times 10^{-7}$ cm$^3$·s/g, more preferably of $3 \times 10^{-7}$ cm$^3$·s/g, most preferably of $0 \times 10^{-7}$ cm$^3$·s/g.

Preferably the first type of water-absorbent polymer particles (G) of the inventive mixture having a SFC of at least $20 \times 10^{-7}$ cm$^3$·s/g, and the second type of water-absorbent polymer particles (H) having a sphericity of at least 0.80 and an SFC of at maximum $5 \times 10^{-7}$ cm$^3$·s/g.

The production process of the first type of water-absorbent polymer particles (G) of the inventive fluid-absorbent mixture comprise the steps of polymerization of the monomer solution, forming and comminuting a polymer gel, drying and grinding of the polymer.

According to one embodiment the inventive mixture of water absorbent polymer particles comprising at least a first type of water-absorbent polymer particles (G) having a SFC of at least $20 \times 10^{-7}$ cm$^3$·s/g, and at least a second type of water-absorbent polymer particles (H) having a sphericity of at least 0.80 and an SFC of maximum $15 \times 10^{-7}$ cm$^3$·s/g, whereas the mixture of equal amounts of the at least a first type of water-absorbent polymer particles (G) and the at least second type of water-absorbent polymer particles (H) has an SFC of at maximum $25 \times 10^{-7}$ cm$^3$·s/g, preferably an SFC of at maximum $23 \times 10^{-7}$ cm$^3 \cdot$s/g, more preferably an SFC of at maximum $20 \times 10^{-7}$ cm$^3 \cdot$s/g.

The inventive mixture of at least a first type of water-absorbent polymer particles (G) having a SFC of at least $20 \times 10^{-7}$ cm$^3 \cdot$s/g, and at least a second type of water-absorbent polymer (H) having a sphericity of at least 0.80 and an SFC of at maximum $15 \times 10^{-7}$ cm$^3 \cdot$s/g present in the absorbent core of an absorbent article ensures compared to the same amount of at least one of the first type (G) and/or the second type (H) of water-absorbent polymer particles an improved performance of the core and/or the absorbent-article especially in respect to rewet under load and/or liquid acquisition time.

C. Fluid-Absorbent Articles

A fluid absorbent article, comprising
(A) an upper liquid-pervious sheet,
(B) a lower liquid-impervious sheet,
(C) a fluid-absorbent core comprising from 60 to 20% by weight fibrous material and from 40 to 80% by weight of water-absorbent polymer particles (G, H) based on the sum of water-absorbent polymer particles and fibrous material; preferably 50 to 30% by weight of fibrous material and from 50 to 70% by weight of water-absorbent polymer particles (G, H),
   more preferably 40 to 35% by weight of fibrous material and from 60 to 65% by weight of water-absorbent polymer particles (G, H),
(D) an optional acquisition-distribution layer (D) between (A) and (C),
(F) other optional components.
According to one embodiment of the invention the fluid-absorbent article, furthermore comprising
(A) an upper liquid-pervious sheet,
(B) a lower liquid-impervious sheet,
(C) a fluid-absorbent core comprising from 60 to 20% by weight fibrous material and from 40 to 80% by weight of at least a first type of water-absorbent polymer particles (G) and at least a second type of water-absorbent polymer particles (H) based on the sum of water-absorbent polymer particles and fibrous material;
(D) an optional acquisition-distribution layer (D) between (A) and (C),
(F) other optional components, wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.
According to another embodiment of the invention the fluid-absorbent article, furthermore comprising
(A) an upper liquid-pervious sheet,
(B) a lower liquid-impervious sheet,
(C) a fluid-absorbent core comprising from 60 to 20% by weight fibrous material and from 40 to 80% by weight of a mixture of at least a first type of water-absorbent polymer particles (G) and at least a second type of water-absorbent polymer particles (H) based on the sum of water-absorbent polymer particles and fibrous material;
(D) an optional acquisition-distribution layer (D) between (A) and (C),
(F) other optional components,
wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

The inventive fluid-absorbent article shows improved rewet and fluid acquisition properties. Fluid-absorbent articles are understood to mean, for example, incontinence pads and incontinence briefs for adults or diapers and training pants for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer (A), vapor permeability without wetting through for the lower liquid-impervious layer (B), a flexible, vapor permeable and thin fluid-absorbent core (C), showing fast absorption rates and being able to retain highest quantities of body fluids, and an optional acquisition-distribution layer (D) between the upper layer (A) and the core (C), acting as transport and distribution layer of the discharged body fluids. These individual elements are combined such that the resultant fluid-absorbent article meets overall criteria such as flexibility, water vapour breathability, dryness, wearing comfort and protection on the user facing side, and concerning liquid retention, rewet and prevention of wet through on the garment side. The specific combination of these layers provides a fluid-absorbent article delivering both high protection levels as well as high comfort to the consumer.

For fluid-absorbent articles it is advantageous especially in respect to fluid distribution to have acquisition-distribution layers. The acquisition-distribution layer (D) acts as transport and distribution layer of the discharged body fluids and is typically optimized to affect efficient liquid distribution with the underlying fluid-absorbent core. Hence, for quick temporary liquid retention it provides the necessary void space while its area coverage of the underlying fluid-absorbent core must affect the necessary liquid distribution and is adopted to the ability of the fluid-absorbent core to quickly dewater the acquisition-distribution layer.

Methods to make fluid absorbent articles are for example described in the following publications and literature cited therein and are expressly incorporated into the present invention: EP 2 301 499 A1, EP 2 314 264 A1, EP 2 387 981 A1, EP 2 486 901 A1, EP 2 524 679 A1, EP 2 524 679 A1, EP 2 524 680 A1, EP 2 565 031 A1, U.S. Pat. No. 6,972,011, US 2011/0162989, US 2011/0270204, WO 2010/004894 A1, WO 2010/004895 A1, WO 2010/076857 A1, WO 2010/082373 A1, WO 2010/118409 A1, WO 2010/133529 A2, WO 2010/143635 A1, WO 2011/084981 A1, WO 2011/086841 A1, WO 2011/086842 A1, WO 2011/086843 A1, WO 2011/086844 A1, WO 2011/117997 A1, WO 2011/136087 A1, WO 2012/048879 A1, WO 2012/052173 A1 und WO 2012/052172 A1.

Typically fluid-absorbent articles according to the invention comprising,
(A) an upper liquid-pervious sheet,
(B) a lower liquid-impervious sheet,
(C) a fluid-absorbent core comprising from 60 to 20% by weight fibrous material and from 40 to 80% by weight of at least a first type of water-absorbent polymer particles
(G) and at least a second type of water-absorbent polymer particles (H) based on the sum of water-absorbent polymer particles and fibrous material;

(D) an optional acquisition-distribution layer (D) between (A) and (C), (F) other optional components, wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

According to the invention the second type of water-absorbent polymer particles has a SFC at maximum of $15 \times 10^{-7}$ cm$^3 \cdot$s/g.

According to another embodiment of the invention the SFC of the second type of water-absorbent polymer particles is more preferably at maximum of $5 \times 10^{-7}$ cm$^3 \cdot$s/g.

According to the invention the production process of the first type of water absorbent polymer particles (G) of the fluid-absorbent core (C) comprises the steps of polymerization of the monomer solution, forming and comminuting a polymer gel, drying and grinding of the polymer.

The fluid-absorbing core (C) according to the inventive fluid-absorbent article may comprise at least two layers (K, L), wherein one of the layers (K) comprises from 60 to 20% by weight fibrous material and 40 to 80% by weight of the first type of water-absorbent polymer particles (G) based on the sum of water-absorbent polymer particles and fibrous material and the second layer (L) comprises from 60 to 20% by weight fibrous material and 40 to 80% by weight of the at least second type of water-absorbent polymer particles (H) based on the sum of water-absorbent polymer particles and fibrous material.

According to a preferred embodiment, in the fluid-absorbent core (C) of the fluid-absorbent article the layer comprising the first type of water-absorbent polymer particles (G) is arranged in z-direction above the layer comprising the at least second type of water-absorbent polymer particles (H).

Whereas it is preferred that the at least first type of water-absorbent polymer particles (G) and the at least second type of water-absorbent polymer particles (H) are present within the fluid-absorbent core (C) in equal amounts by weight.

It is furthermore preferred that the at least first type of water-absorbent polymer particles (G) is present of at least 30% by weight, preferably of at least 33% by weight and the second type of water-absorbent polymer particles (H) are present at maximum of 66% by weight, preferably of at maximum 70% by weight within the fluid-absorbent core (C) based on the sum of water-absorbent polymer particles (G, H).

According to another embodiment of the invention, in the fluid absorbent article the at least first type of water-absorbent polymer particles (G) is present in an amount of at least 50% by weight and the second type of water-absorbent polymer particles (H) are present of at maximum 50% by weight within the fluid-absorbent core (C) based on the sum of water-absorbent polymer particles (G, H).

It could be preferred that the at least first type of water-absorbent polymer particles (G) is present of at maximum 66% by weight, preferably of at maximum 70% by weight and the second type of water-absorbent polymer particles (H) are present of at least 30% by weight, preferably of at least 33% by weight within the fluid-absorbent core (C) based on the sum of water-absorbent polymer particles (G, H).

According to another embodiment of the invention in the fluid-absorbent core (C) the layer comprising the first type of water-absorbent polymer particles (G) is arranged in z-direction above the layer comprising the at least second type of water-absorbent polymer particles (H). According to the invention for this embodiment the rewet under load (RUL) for the 4th insult and/or the sum of rewet under load for 4 succeeding insults is reduced by at least 20%, preferably at least 50% compared to a fluid-absorbent article wherein the total amount of water-absorbent polymer particles (G and H) in the fluid-absorbent core (C) are replaced by the same amount by weight of the first type (G) of water-absorbent polymer particles. Furthermore for this embodiment it is preferred that the acquisition time for the 4th insult and/or the sum of acquisition times for 4 succeeding insults is reduced by at least 5%, preferably at least 10%, at maximum up to 20% compared to a fluid-absorbent article wherein the total amount of water-absorbent polymer particles (G and H) in the fluid-absorbent core (C) are replaced by the same amount by weight of the second type (H) of water-absorbent polymer particles.

For an embodiment providing equal amounts of the respective water-absorbent polymer particles (G, H) in each layer (K, L) of the fluid-absorbent core and wherein in the fluid-absorbent core (C) the layer comprising the first type of water-absorbent polymer particles (G) is arranged in z-direction above the layer comprising the at least second type of water-absorbent polymer particles (H), it is preferred that its rewet under load (RUL) for the 4th insult and/or the sum of rewet under load for 4 succeeding insults is reduced by at least 20%, preferably at least 50%, at maximum up to 80% compared to a fluid-absorbent article wherein the total amount of water-absorbent polymer particles (G and H) in the fluid-absorbent core (C) are replaced by the same amount by weight of the first type (G) of water-absorbent polymer particles.

For this embodiment providing equal amounts of the respective water-absorbent polymer particles (G, H) in each layer (K, L) of the fluid-absorbent core and wherein in the fluid-absorbent core (C) the layer comprising the first type of water-absorbent polymer particles (G) is arranged in z-direction above the layer comprising the at least second type of water-absorbent polymer particles (H), it could be preferred that the acquisition time for the 4th insult and/or the sum of acquisition times for 4 succeeding insults is reduced by at least 5%, preferably at least 10%, at maximum up to 20% compared to a fluid-absorbent article wherein the total amount of water-absorbent polymer particles (G and H) in the fluid-absorbent core (C) are replaced by the same amount by weight of the second type (H) of water-absorbent polymer particles.

An absorbent article according to the invention preferably comprise as shown in FIG. 16 an upper liquid-pervious layer (A), a lower liquid-impervious layer (B) at least one fluid absorbent core (C) comprising one (FIG. 16 A) or two layers (K, L) (FIG. 16 B) of water-absorbent polymer particles (G, H), which are mixed with fibrous material (M), between (A) and (B); and an acquisition-distribution layer (D) between (A) and (C), an optional tissue layer disposed immediately above and/or below (C) or wrapped fully or partially around (C). The layers may optionally be connected to each other by binder (N) e. g. by adhesive, ultrasonic bonding or any other suitable method.

According to the invention the two layers of water-absorbent polymer particles (K, L), are positioned adjacent to one another in direct connection or connected by a binder (N). According to the invention each layer (K, L) of water-absorbent polymer particles (G, H) could be wrapped with an optional tissue layer. An airthrough bonded layer is not present between layers (K, L).

According to another embodiment the fluid-absorbent articles according to the invention comprising,
(A) an upper liquid-pervious sheet,
(B) a lower liquid-impervious sheet,
(C) a fluid-absorbent core comprising from 60 to 20% by weight fibrous material and from 40 to 80% by weight of a mixture of at least a first type of water-absorbent polymer particles (G) and at least a second type of water-absorbent polymer particles (H) based on the sum of water-absorbent polymer particles and fibrous material;
(D) an optional acquisition-distribution layer (D) between (A) and (C),
(F) other optional components,
wherein the first type of water absorbent polymer particles (G) of the fluid-absorbent core (C) have a SFC of at least $20 \times 10^{-7}$ cm$^3$·s/g and wherein the at least second type of water-absorbent polymer particles (H) of the fluid-absorbent core have a sphericity of at least 0.80.

According to the invention the second type of water-absorbent polymer particles has a SFC at maximum of $15 \times 10^{-7}$ cm$^3$·s/g.

According to another embodiment of the invention the SFC of the second type of water-absorbent polymer particles is more preferably at maximum of $5 \times 10^{-7}$ cm$^3$·s/g.

According to the invention, the production process of the first type of water absorbent polymer particles (G) of the fluid-absorbent core (C) comprises the steps of polymerization of the monomer solution, forming and comminuting a polymer gel, drying and grinding of the polymer.

According to the inventive fluid-absorbent article the mixture comprises at least a first type of water-absorbent polymer particles (G) and at least a second type of water-absorbent polymer particles (H) based on the sum of water-absorbent polymer particles (G, H) and fibrous material;
wherein the first type of water absorbent polymer particles (G) of the fluid-absorbent core (C) have a SFC of at least $20 \times 10^{-7}$ cm$^3$·s/g and wherein the at least second type of water-absorbent polymer particles (H) of the fluid-absorbent core have a sphericity of at least 0.80.

According to an embodiment of the inventive fluid-absorbent article, the at least first type of water-absorbent polymer particles (G) is present of at least 30% by weight, preferably of at least 33% by weight within the fluid-absorbent core (C) based on the sum of water-absorbent polymer particles (G, H).

According to an embodiment of the inventive fluid-absorbent article the at least first type of water-absorbent polymer particles (G) is present of at least 50% by weight within the fluid-absorbent core (C) based on the sum of water-absorbent polymer particles (G, H).

According to another embodiment of the inventive fluid-absorbent article the at least first type of water-absorbent polymer particles (G) is present of at maximum 66% by weight, preferably of at maximum 70% by weight within the fluid-absorbent core (C) based on the sum of water-absorbent polymer particles (G, H).

According to further embodiment of the inventive fluid-absorbent article the mixture of at least a first type of water-absorbent polymer particles (G) and at least a second type of water-absorbent polymer particles (H) within the absorbent core comprises at least 30% by weight, preferably least 33% by weight of the first type of water-absorbent polymer particles (G) and at maximum 66% by weight, preferably at maximum 70% by weight of the second type of water-absorbent polymer particles (H) based on the sum of water-absorbent polymer particles (G, H).

According to the invention the mixture of at least a first type of water-absorbent polymer particles (G) and at least a second type of water-absorbent polymer particles (H) within the absorbent core comprises at least 50% by weight of the first type of water-absorbent polymer particles (G) and at maximum 50% by weight of the second type of water-absorbent polymer particles (H) based on the sum of water-absorbent polymer particles (G, H).

According to the invention the mixture of at least a first type of water-absorbent polymer particles (G) and at least a second type of water-absorbent polymer particles (H) within the absorbent core comprises at maximum 66% by weight, preferably at maximum 70% by weight of the first type of water-absorbent polymer particles (G) and at least 30% by weight, preferably at least 33% by weight of the second type of water-absorbent polymer particles (H) based on the sum of water-absorbent polymer particles (G, H).

For an embodiment of the inventive fluid-absorbent article the rewet under load (RUL) for the 4th insult and/or the sum of rewet under load for 4 succeeding insults is reduced by at least 20%, preferably at least 50% compared to a fluid-absorbent article wherein the total amount of water-absorbent polymer particles (G and H) in the fluid-absorbent core (C) are replaced by the same amount by weight of the first type (G) of water-absorbent polymer particles.

Furthermore it is preferred that the acquisition time for the 4th insult and/or the sum of acquisition times for 4 succeeding insults for the inventive absorbent article is reduced by at least 5%, preferably at least 10%, at maximum up to 20% compared to a fluid-absorbent article wherein the total amount of water-absorbent polymer particles (G and H) in the fluid-absorbent core (C) are replaced by the same amount by weight of the second type (H) of water-absorbent polymer particles.

Preferably for an embodiment of the inventive fluid-absorbent article providing equal amounts of the first type of water-absorbent polymer particles (G) and at least a second type of water-absorbent polymer particles (H) in the fluid-absorbent core (C) it is preferred that for the fluid-absorbent core (C) rewet under load (RUL) for the 4$^{th}$ insult and/or the sum of rewet under load for 4 succeeding insults is reduced by at least 20%, preferably at least 50%, at maximum up to 80% compared to a fluid-absorbent article wherein the total amount of water-absorbent polymer particles (G and H) in the fluid-absorbent core (C) are replaced by the same amount by weight of the first type (G) of water-absorbent polymer particles.

For this embodiment providing equal amounts by weight of the first type of water-absorbent polymer particles (G) and at least a second type of water-absorbent polymer particles (H) in the fluid-absorbent core (C), it is preferred that for the fluid-absorbent core (C) the acquisition time for the 4th insult and/or the sum of acquisition times for 4 succeeding insults is reduced by at least 5%, preferably at least 10%, at maximum up to 20% compared to a fluid-absorbent article wherein the total amount of water-absorbent polymer particles (G and H) in the fluid-absorbent core (C) are replaced by the same amount by weight of the second type (H) of water-absorbent polymer particles.

According to the invention the production process of the first type of water absorbent polymer particles (G) of the fluid-absorbent core (C) comprises the steps of polymerization of the monomer solution, forming and comminuting a polymer gel, drying and grinding of the polymer. The resulting water absorbent polymer particles are therefore irregularly shaped.

According to the invention the at least first type of water-absorbent polymer particles (G) and the at least second type of water-absorbent polymer particles (H) are present within the fluid-absorbent core (C) of the fluid-absorbent article in equal amounts by weight.

Liquid-Pervious Sheet or Liquid Pervious Layer (A)

The liquid-pervious sheet (A) is the layer which is in direct contact with the skin. Thus, the liquid-pervious sheet is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious sheet is the acquisition and transport of body fluids from the wearer towards the fluid-absorbent core. Typically liquid-pervious layers are formed from any materials known in the art such as nonwoven material, films or combinations thereof. Suitable liquid-pervious sheets (A) consist of customary synthetic or semisynthetic fibers or bicomponent fibers or films of polyester, polyolefins, rayon or natural fibers or any combinations thereof. In the case of nonwoven materials, the fibers should generally be bound by binders such as polyacrylates. Additionally the liquid-pervious sheet may contain elastic compositions thus showing elastic characteristics allowing to be stretched in one or two directions.

Suitable synthetic fibers are made from polyvinyl chloride, polyvinyl fluoride, polytetrafluoroethylene, polyvinylidene chloride, polyacrylics, polyvinyl acetate, polyethylvinyl acetate, non-soluble or soluble polyvinyl alcohol, polyolefins such as polyethylene, polypropylene, polyamides, polyesters, polyurethanes, polystyrenes and the like.

Examples for films are apertured formed thermoplastic films, apertured plastic films, hydro-formed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

The fibrous material may comprise only natural fibers or synthetic fibers or any combination thereof. Preferred materials are polyester, rayon and blends thereof, polyethylene, and polypropylene. The fibrous material as a component of the fluid-absorbent compositions may be hydrophilic, hydrophobic or can be a combination of both hydrophilic and hydrophobic fibers. The definition of hydrophilic is given in the section "definitions" in the chapter above. The selection of the ratio hydrophilic/hydrophobic and accordingly the amount of hydrophilic and hydrophobic fibers within fluid-absorbent composition will depend upon fluid handling properties and the amount of water-absorbent polymer particles of the resulting fluid-absorbent composition. Such, the use of hydrophobic fibers is preferred if the fluid-absorbent composition is adjacent to the wearer of the fluid-absorbent article, that is to be used to replace partially or completely the upper liquid-pervious layer, preferably formed from hydrophobic nonwoven materials. Hydrophobic fibers can also be member of the lower breathable, but fluid-impervious layer, acting there as a fluid-impervious barrier.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e. g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of raising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multicomponent fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermically treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed 30 jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the nonwoven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven.

In newest researches benefits are found in some structural features of the resulting liquid-pervious layers. For example, the thickness of the layer is very important and influences together with its x-y dimension the acquisition-distribution behaviour of the layer. If there is further some profiled structure integrated, the acquisition-distribution behaviour can be directed depending on the three-dimensional structure of the layer. Thus 3D-polyethylene in the function of liquid-pervious layer is preferred.

Thus, suitable liquid-pervious sheets (A) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Typically liquid-pervious sheets (A) extend partially or wholly across the fluid-absorbent structure and can extend into and/or form part of all the preferred sideflaps, side wrapping elements, wings and ears.

Liquid-Impervious Sheet or Liquid Impervious Layer (B)

The liquid-impervious sheet (B) prevents the exudates absorbed and retained by the fluid-absorbent core from wetting articles which are in contact with the fluid-absorbent article, as for example bedsheets, pants, pajamas and undergarments. The liquid-impervious sheet (B) may thus comprise a woven or a nonwoven material, polymeric films such as thermoplastic film of polyethylene or polypropylene, or composite materials such as film-coated nonwoven material.

Suitable liquid-impervious sheets include nonwoven, plastics and/or laminates of plastic and nonwoven. Both, the plastics and/or laminates of plastic and nonwoven may appropriately be breathable, that is, the liquid-impervious layer (B) can permit vapors to escape from the fluid-absorbent material. Thus the liquid-impervious sheet has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spunbonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious sheets are permeable for vapor. Preferably the liquid-impervious sheet is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious sheet (B) is made of nonwoven comprising hydrophobic materials, e.g. synthetic fibers or a liquid-impervious polymeric film comprising plastics e.g. polyethylene. The thickness of the liquid-impervious sheet is preferably 15 to 30 µm.

Further, the liquid-impervious sheet (B) is preferably made of a laminate of nonwoven and plastics comprising a nonwoven having a density of 12 to 15 gsm and a polyethylene layer having a thickness of about 10 to 20 µm.

The typically liquid-impervious sheet (B) extends partially or wholly across the fluid-absorbent structure and can extend into and/or form part of all the preferred sideflaps, side wrapping elements, wings and ears.

Fluid-Absorbent Core (C)

The fluid-absorbent core (C) is disposed between the upper liquid-pervious sheet (A) and the lower liquid-impervious sheet (B).

According to the present invention the fluid-absorbent core can include the following components:
1. an optional core cover
2. a fluid storage layer
3. an optional dusting layer 1. Optional Core Cover In order to increase the integrity of the fluid-absorbent core, the core is provided with a cover. This cover may be at the top and/or at the bottom of the fluid-absorbent core with bonding at lateral juncture and/or bonding at the distal juncture by hot-melt, ultrasonic bonding, thermal bonding or combination of bonding techniques know to persons skilled in the art. Further, this cover may include the whole fluid-absorbent core with a unitary sheet of material and thus function as a wrap. Wrapping is possible as a full wrap, a partial wrap or as a C-Wrap.

The material of the core cover may comprise any known type of substrate, including nonwovens, webs, garments, textiles, films, tissues and laminates of two or more substrates or webs. The core cover material may comprise natural fibers, such as cellulose, cotton, flax, linen, hemp, wool, silk, fur, hair and naturally occurring mineral fibers. The core cover material may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the core cover comprises synthetic fibers or tissue.

The fibers may be mono- or multicomponent. Multicomponent fibers may comprise a homopolymer, a copolymer or blends thereof.

2. Fluid-Storage Layer

According to the invention the fluid-absorbent core comprising from 60 to 20% by weight fibrous material and from 40 to 80% by weight of at least a first type of water-absorbent polymer particles (G) and at least a second type of water-absorbent polymer particles (H) based on the sum of water-absorbent polymer particles (G, H) and fibrous material;
wherein the first type of water absorbent polymer particles (G) of the fluid-absorbent core (C) have a SFC of at least $20 \times 10^{-7}$ cm$^3$·s/g and wherein the at least second type of water-absorbent polymer particles (H) of the fluid-absorbent core have a sphericity of at least 0.80

According to the invention the SFC of the second type of water-absorbent polymer particles is at maximum of $15 \times 10^{-7}$ cm$^3$·s/g, preferably of at maximum of $10 \times 10^{-7}$ cm$^3$·s/g, particularly preferred of at maximum of $5 \times 10^{-7}$ cm$^3$·s/g, more preferably of $3 \times 10^{-7}$ cm$^3$·s/g, most preferably of $0 \times 10^{-7}$ cm$^3$·s/g.

According to the invention the production process of the first type of water absorbent polymer particles (G) of the fluid-absorbent core (C) comprises the steps of polymerization of the monomer solution, forming and comminuting a polymer gel, drying and grinding of the polymer.

The water absorbent polymer particles (G, H) present are preferably surface-postcrosslinked. An embodiment of the fluid-absorbing core (C) according to the invention comprising at least two layers (K, L). as illustrated in FIG. 16 B. One of the layers (K) comprises from 60 to 20% by weight fibrous material and 40 to 80% by weight of the first type of water-absorbent polymer particles (G) based on the sum of water-absorbent polymer particles and fibrous material and the second layer (L) comprises from 60 to 20% by weight fibrous material and 40 to 80% by weight of the at least second type of water-absorbent polymer particles (H) based on the sum of water-absorbent polymer particles and fibrous material.

To ensure a low rewet and a fast liquid acquisition it is preferred in the fluid-absorbent core according to the invention to arrange the layer comprising the first type of water-absorbent polymer particles (G) in z-direction above the layer comprising the at least second type of water-absorbent polymer particles (H).

It is preferred that the amount of the at least first type of water-absorbent polymer particles (G) in one layer and the amount of the at least second type of water-absorbent polymer particles (H) in the second layer are equal by weight.

According to an embodiment of the inventive fluid-absorbent core, the at least first type of water-absorbent polymer particles (G) is present of at least 30% by weight, preferably of at least 33% by weight within the fluid-absorbent core (C) based on the sum of water-absorbent polymer particles (G, H).

According to an embodiment of the inventive fluid-absorbent core the at least first type of water-absorbent polymer particles (G) is present of at least 50% by weight within the fluid-absorbent core (C) based on the sum of water-absorbent polymer particles (G, H).

According to another embodiment of the inventive fluid-absorbent core the at least first type of water-absorbent polymer particles (G) is present of at maximum 66% by weight, preferably of at maximum 70% by weight within the fluid-absorbent core (C) based on the sum of water-absorbent polymer particles (G, H).

It is furthermore preferred that the at least first type of water-absorbent polymer particles (G) is present of at least 30% by weight, preferably of at least 33% by weight and the second type of water-absorbent polymer particles (H) are present of at maximum 66% by weight, preferably of at maximum 70% by weight within the fluid-absorbent core (C) based on the sum of water-absorbent polymer particles (G, H).

According to another embodiment of the invention the at least first type of water-absorbent polymer particles (G) is present in an amount of at least 50% by weight and the second type of water-absorbent polymer particles (H) are present of at maximum 50% by weight within the fluid-absorbent core (C) based on the sum of water-absorbent polymer particles (G, H).

It is also preferred that the at least first type of water-absorbent polymer particles (G) is present of at maximum 66% by weight, preferably of at maximum 70% by weight and the second type of water-absorbent polymer particles (H) are present of at least 30% by weight, preferably of at least 33% by weight within the fluid-absorbent core (C) based on the sum of water-absorbent polymer particles (G, H).

For the embodiment of the invention in the fluid-absorbent core (C) the layer comprising the first type of water-absorbent polymer particles (G) is arranged in z-direction above the layer comprising the at least second type of water-absorbent polymer particles (H). For this embodiment it could be preferred that its rewet under load (RUL) for the 4th insult is reduced by at least 20%, preferably at least 50% compared to a fluid-absorbent article wherein the total amount of water-absorbent polymer particles (G and H) in the fluid-absorbent core (C) are replaced by the same amount by weight of the first type (G) of water-absorbent polymer particles.

Furthermore it is preferred that the acquisition time for the 4th insult and/or the sum of acquisition times for 4 succeeding insults for the inventive absorbent core is reduced by at least 5%, preferably at least 10%, at maximum up to 20% compared to a fluid-absorbent core wherein the total amount of water-absorbent polymer particles (G and H) in the fluid-absorbent core (C) are replaced by the same amount by weight of the second type (H) of water-absorbent polymer particles.

For an embodiment providing equal amounts of the respective water-absorbent polymer particles (G, H) in each layer (K, L) of the fluid-absorbent core (C) and wherein in the fluid-absorbent core (C) the layer comprising the first type of water-absorbent polymer particles (G) is arranged in z-direction above the layer comprising the at least second type of water-absorbent polymer particles (H), it could be preferred that its rewet under load (RUL) for the 4th insult and/or the sum of rewet under load for 4 succeeding insults is reduced by at least 20%, preferably at least 50%, at maximum up to 80% compared to a fluid-absorbent article and/or fluid absorbent core wherein the total amount of water-absorbent polymer particles (G and H) in the fluid-absorbent core (C) are replaced by the same amount by weight of the first type (G) of water-absorbent polymer particles. For this embodiment it is preferred that equal amounts of the respective water-absorbent polymer particles (G, H) in each layer (K, L) of the fluid-absorbent core are provided.

For an embodiment providing equal amounts of the respective water-absorbent polymer particles (G, H) in each layer (K, L) of the fluid-absorbent core (C) and wherein the layer comprising the first type of water-absorbent polymer particles (G) is arranged in z-direction above the layer comprising the at least second type of water-absorbent polymer particles (H), it could be preferred that the acquisition time for the 4th insult and/or the sum of acquisition times for 4 succeeding insults is reduced by at least 5%, preferably at least 10%, at maximum up to 20% compared to a fluid-absorbent article and/or fluid absorbent core wherein the total amount of water-absorbent polymer particles (G and H) in the fluid-absorbent core (C) are replaced by the same amount by weight of the second type (H) of water-absorbent polymer particles.

Especially the layered core comprising both water-absorbent polymer particles in equal amount by weight, surprisingly shows a synergistic effect in the fluid-absorbent article.

But the direct mixture of the first type (G) and the second type (H) of fluid-absorbent polymer particles is preferred.

According to another embodiment of the invention the fluid-absorbent core comprising from 60 to 20% by weight fibrous material and from 40 to 80% by weight of a mixture of at least a first type of water-absorbent polymer particles (G) and at least a second type of water-absorbent polymer particles (H) based on the sum of water-absorbent polymer particles (G, H) and fibrous material;

wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

According to an embodiment of the inventive fluid-absorbent core, the at least first type of water-absorbent polymer particles (G) is present of at least 30% by weight, preferably of at least 33% by weight within the fluid-absorbent core (C) based on the sum of water-absorbent polymer particles (G, H).

According to an embodiment of the inventive fluid-absorbent core the at least first type of water-absorbent polymer particles (G) is present of at least 50% by weight within the fluid-absorbent core (C) based on the sum of water-absorbent polymer particles (G, H).

According to another embodiment of the inventive fluid-absorbent core the at least first type of water-absorbent polymer particles (G) is present of at maximum 66% by weight, preferably of at maximum 70% by weight within the fluid-absorbent core (C) based on the sum of water-absorbent polymer particles (G, H).

According to the invention the mixture of at least a first type of water-absorbent polymer particles (G) and at least a second type of water-absorbent polymer particles (H) within the absorbent core comprises at least 30% by weight, preferably least 33% by weight of the first type of water-absorbent polymer particles (G) and at maximum 66% by weight, preferably at maximum 70% by weight of the second type of water-absorbent polymer particles (H) based on the sum of water-absorbent polymer particles (G, H).

According to the invention the mixture of at least a first type of water-absorbent polymer particles (G) and at least a second type of water-absorbent polymer particles (H) within the absorbent core comprises at least 50% by weight of the first type of water-absorbent polymer particles (G) and at maximum 50% by weight of the second type of water-absorbent polymer particles (H) based on the sum of water-absorbent polymer particles (G, H).

According to the invention the mixture of at least a first type of water-absorbent polymer particles (G) and at least a second type of water-absorbent polymer particles (H) within the absorbent core comprises at maximum 66% by weight, preferably at maximum 70% by weight of the first type of water-absorbent polymer particles (G) and at least 30% by weight, preferably at least 33% by weight of the second type of water-absorbent polymer particles (H) based on the sum of water-absorbent polymer particles (G, H).

According to the invention the absorbent core the first type of fluid-absorbent polymer particles (G) have a SFC of at least $20 \times 10^{-7}$ cm$^3 \cdot$s/g, preferably of at least $25 \times 10^{-7}$ cm$^3 \cdot$s/g, particularly preferred of at least $30 \times 10^{-7}$ cm$^3 \cdot$s/g, preferentially of at least $40 \times 10^{-7}$ cm$^3 \cdot$s/g, more preferably of at least $60 \times 10^{-7}$ cm$^3 \cdot$s/g, most preferably of at least $80 \times 10^{-7}$ cm$^3 \cdot$s/g, further most preferably of at least $100 \times 10^{-7}$ cm$^3 \cdot$s/g, but not above $200 \times 10^{-7}$ cm$^3 \cdot$s/g.

According to a further embodiment of the inventive absorbent core the second type of water-absorbent polymer particles (H) have an SFC of at maximum of $15 \times 10^{-7}$ cm$^3 \cdot$s/g, preferably of at maximum of $10 \times 10^{-7}$ cm$^3 \cdot$s/g, particularly preferred of at maximum of $5 \times 10^{-7}$ cm$^3 \cdot$s/g, more preferably of $3 \times 10^{-7}$ cm$^3 \cdot$s/g, most preferably of $0 \times 10^{-7}$ cm$^3 \cdot$s/g.

According to another embodiment the second type of water-absorbent polymer particles (H) of the inventive absorbent core have a sphericity of at least 0.80, preferably of at least 0.85, particularly preferred of at least 0.90.

According to the invention the absorbent core the second type of water-absorbent polymer particles (H) have a sphericity of at least 0.80 and a SFC of at maximum $5 \times 10^{-7}$ cm$^3 \cdot$s/g.

According to the inventive absorbent core the production process of the first type of water absorbent polymer particles (G) of the fluid-absorbent core (C) comprises the steps of polymerization of the monomer solution, forming and comminuting a polymer gel, drying and grinding of the polymer.

According to the invention the second type of water absorbent polymer particles (H) of the fluid-absorbent core (C) are produced by polymerizing droplets of a monomer solution in a surrounding heated gas phase.

The water absorbent polymer particles (G, H) of the fluid-absorbent article or absorbent core respectively according to one embodiment of the invention are surface-postcrosslinked.

For an embodiment according to the invention it is preferred that its rewet under load (RUL) for the 4th insult is reduced by at least 20%, preferably at least 50% compared to a fluid-absorbent article wherein the total amount of water-absorbent polymer particles (G and H) in the fluid-absorbent core (C) are replaced by the same amount by weight of the first type (G) of water-absorbent polymer particles.

Furthermore according to the invention the acquisition time for the 4th insult and/or the sum of acquisition times for 4 succeeding insults for the inventive absorbent core is reduced by at least 5%, preferably at least 10%, at maximum up to 20% compared to a fluid-absorbent core wherein the total amount of water-absorbent polymer particles (G and H) in the fluid-absorbent core (C) are replaced by the same amount by weight of the second type (H) of water-absorbent polymer particles.

For an embodiment providing a mixture of equal amounts by weight of the first type of water-absorbent polymer particles (G) and at least a second type of water-absorbent polymer particles (H) in the fluid-absorbent core (C) it is preferred that for the fluid-absorbent core (C) rewet under load (RUL) for the $4^{th}$ insult and/or the sum of rewet under load for 4 succeeding insults is reduced by at least 20%, preferably at least 50%, at maximum up to 80% compared to a fluid-absorbent article and/or fluid absorbent core wherein the total amount of water-absorbent polymer particles (G and H) in the fluid-absorbent core (C) are replaced by the same amount by weight of the first type (G) of water-absorbent polymer particles.

For an absorbent core according to the invention comprising a mixture of equal amounts by weight of the first type of water-absorbent polymer particles (G) and at least a second type of water-absorbent polymer particles (H) in the fluid-absorbent core (C), it is preferred that for the fluid-absorbent core (C) the acquisition time for the 4th insult and/or the sum of acquisition times for 4 succeeding insults is reduced by at least 5%, preferably at least 10%, at maximum up to 20% compared to a fluid-absorbent article and/or fluid absorbent core wherein the total amount of water-absorbent polymer particles (G and H) in the fluid-absorbent core (C) are replaced by the same amount by weight of the second type (H) of water-absorbent polymer particles.

The direct mixture of the first type and the second type of fluid-absorbent polymer particles, preferred a homogeneous mixture, preferably in equal amounts by weight in the absorbent core results in a reduction of rewet under load and liquid acquisition time measurements compared to cores containing the same amount of only one of the respective fluid-absorbent polymer particles. Surprisingly the mixture ensures better values in respect to rewet under load and liquid acquisition time. The mixture is synergistic in respect to rewet under load and liquid acquisition time.

Fibers useful in the absorbent core according to the present invention include natural fibers and synthetic fibers. Examples of suitable modified or unmodified natural fibers are given in the chapter "Liquid-pervious Layer (A)" above. From those, wood pulp fibers are preferred.

Examples of suitable synthetic fibers are given in the chapter "Liquid-pervious Layer (A)" above. The fibrous material may comprise only natural fibers or synthetic fibers or any combination thereof.

The fibrous material as a component of the fluid-absorbent compositions may be hydrophilic, hydrophobic or can be a combination of both hydrophilic and hydrophobic fibers.

Generally for the use in a fluid-absorbent core, which is the embedded between the upper layer (A) and the lower layer (B), hydrophilic fibers are preferred. This is especially the case for fluid-absorbent compositions that are desired to quickly acquire, transfer and distribute discharged body fluids to other regions of the fluid-absorbent composition or fluid-absorbent core. The use of hydrophilic fibers is especially preferred for fluid-absorbent compositions comprising water-absorbent polymer particles.

Examples for hydrophilic fibers are given in the chapter "Liquid-pervious Layer (A)" above. Preferably, the fluid-absorbent core is made from viscose acetate, polyester and/or polypropylene.

The fibrous material of the fluid-absorbent core may be uniformly mixed to generate a homogenous or in-homogenous fluid-absorbent core. Alternatively the fibrous material may be concentrated or laid in separate layers optionally comprising water-absorbent polymer material. Suitable storage layers of the fluid-absorbent core comprising homogenous mixtures of fibrous materials comprising water-absorbent polymer material. Suitable storage layers of the fluid-absorbent core including a layered core-system comprise homogenous mixtures of fibrous materials and comprise water-absorbent polymer material, whereby each of the layers may be built from any fibrous material by means known in the art. The sequence of the layers may be directed such that a desired fluid acquisition, distribution and transfer results, depending on the amount and distribution of the inserted fluid-absorbent material, e.g. water-absorbent polymer particles. Preferably there are discrete zones of highest absorption rate or retention within the storage layer of the fluid-absorbent core, formed of layers or in-homogenous mixtures of the fibrous material, acting as a matrix for the incorporation of water-absorbent polymer particles. The zones may extend over the full area or may form only parts of the fluid-absorbent core.

Suitable fluid-absorbent cores comprise fibrous material and fluid-absorbent material. Suitable is any fluid-absorbent material that is capable of absorbing and retaining body fluids or body exudates such as cellulose wadding, modified and unmodified cellulose, crosslinked cellulose, laminates, composites, fluid-absorbent foams, materials described as in the chapter "Liquid-pervious Layer (A)" above, water-absorbent polymer particles and combinations thereof.

Techniques of application of the water-absorbent polymer materials into the absorbent core are known to persons skilled in the art and may be volumetric, loss-in-weight or gravimetric. Known techniques include the application by vibrating systems, single and multiple auger systems, dosing roll, weigh belt, fluid bed volumetric systems and gravitational sprinkle and/or spray systems. Further techniques of insertion are falling dosage systems consensus and contradictory pneumatic application or vacuum printing method of applying the fluid absorbent polymer materials.

As suitable fluid-absorbent cores may also include layers, which are formed by the process of manufacturing the fluid-absorbent article. The layered structure may be formed by subsequently generating the different layers in z-direction.

Alternatively a core-structure can be formed from two or more preformed layers to get a layered fluid-absorbent core.

Alternatively layers of other materials can be added, e.g. layers of opened or closed celled foams or perforated films. Included are also laminates of at least two layers comprising said water-absorbent polymer material.

According to the invention it is preferred that the fluid-absorbent core (C) comprises not more than 20% by weight of an adhesive. The quantity of water-absorbent polymer particles within the fluid-absorbent core is from 3 to 20 g, preferably from 4 to 18, more preferably from 6 to 16 g, and from 8 to 13 g in the case of maxi-diapers, and in the case of incontinence products up to about 50 g.

The fluid-absorbent core (C) typically has a uniform size or profile. Suitable fluid-absorbent cores can also have profiled structures, concerning the shape of the core and/or the content of water-absorbent polymer particles and/or the distribution of the water-absorbent polymer particles and/or the dimensions of the different layers if a layered fluid-absorbent core is present.

The shape of the core in view from above (x-y dimension) can be rectangular, anatomical shaped with a narrower crotch area or any other shapes.

The top view area of the fluid-absorbent core (C) is preferably at least 200 $cm^2$, more preferably at least 250 $cm^2$, most preferably at least 300 $cm^2$. The top view area is the part of the core that is face-to-face to the upper liquid-pervious layer (A).

The fluid-absorbent core may comprise additional additives typically present in fluid-absorbent articles known in the art. Exemplary additives are fibers for reinforcing and stabilizing the fluid-absorbent core. Preferably polyethylene is used for reinforcing the fluid-absorbent core.

Further suitable stabilizer for reinforcing the fluid-absorbent core are materials acting as binder.

In varying the kind of binder material or the amount of binder used in different regions of the fluid-absorbent core it is possible to get a profiled stabilization. For example, different binder materials exhibiting different melting temperatures may be used in regions of the fluid-absorbent core, e.g. the lower melting one in the central region of the core, and the higher melting in the distal regions. Suitable binder materials may be adhesive or non-adhesive fibers, continuously or discontinuously extruded fibers, bi-component staple fibers, non-elastomeric fibers and sprayed liquid binder or any combination of these binder materials.

Further, thermoplastic compositions usually are added to increase the integrity of the core layer. Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefin or styrene block copolymer and mixture of waxes.

Suitable thermoplastic polymers are styrenic block copolymers including A-B-A triblock segments, A-B diblock segments and $(A-B)_n$ radial block copolymer segments. The letter A designs non-elastomeric polymer segments, e.g. polystyrene, and B stands for unsaturated conjugated diene or their (partly) hydrogenated form. Preferably B comprises isoprene, butadiene, ethylene/butylene (hydrogenated butadiene), ethylene/propylene (hydrogenated isoprene) and mixtures thereof.

Other suitable thermoplastic polymers are amorphous polyolefins, amorphous polyalphaolefins and metallocene polyolefins.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid. Suitable odor control additives are further antimicrobial agents such as quaternary ammonium, phenolic, amide and nitro compounds and mixtures thereof; bactericides such as silver salts, zinc salts, cetylpyridinium chloride and/or triclosan as well as surfactants having an HLB value of less than 12.

Suitable odor control additives are further compounds with anhydride groups such as maleic-, itaconic-, polymaleic- or polyitaconic anhydride, copolymers of maleic acid with $C_2$-$C_8$ olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of $C_3$-$C_5$ mono-unsaturated carboxylic acids.

Suitable odor control additives are further perfumes such as allyl caproate, allyl cyclohexaneacetate, allyl cyclohexanepropionate, allyl heptanoate, amyl acetate, amyl propionate, anethol, anixic aldehyde, anisole, benzaldehyde, benzyl acetete, benzyl acetone, benzyl alcohole, benzyl butyrate, benzyl formate, camphene, camphor gum, laevocarveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol etc.

Optional Dusting Layer

An optional component for inclusion into the absorbent core is a dusting layer adjacent to. The dusting layer is a fibrous layer and may be placed on the top and/or the bottom of the absorbent core. Typically, the dusting layer is underlying the storage layer. This underlying layer is referred to as a dusting layer, since it serves as carrier for deposited water-absorbent polymer particles during the manufacturing process of the fluid-absorbent core. If the water-absorbent polymer material is in the form of macrostructures, films or flakes, the insertion of a dusting layer is not necessary. In the case of water-absorbent polymer particles derived from dropletization polymerization, the particles have a smooth surface with no edges. Also in this case, the addition of a dusting layer to the fluid-absorbent core is not necessary. On the other side, as a great advantage the dusting layer provides some additional fluid-handling properties such as wicking performance and may offer reduced incidence of pin-holing and or pock marking of the liquid impervious layer (B).

Preferably, the dusting layer is a fibrous layer comprising fluff (cellulose fibers).

Acquisition-Distribution Layer (D)

An optional acquisition-distribution layer (D) is located between the upper layer (A) and the fluid-absorbent core (C) and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the fluid-absorbent core.

The acquisition-distribution layer (D) comprises fibrous material.

Preferred acquisition-distribution layers may be hydrophilic, hydrophobic or can be a combination of both hydrophilic and hydrophobic fibers. It may be derived from natural fibers, synthetic fibers or a combination of both.

Suitable acquisition-distribution layers are formed from cellulosic fibers and/or modified cellulosic fibers and/or synthetics or combinations thereof. Thus, suitable acquisition-distribution layers may contain cellulosic fibers, in particular wood pulp fluff. Examples of further suitable hydrophilic, hydrophobic fibers, as well as modified or unmodified natural fibers are given in the chapter "Liquid-pervious sheet or liquid pervious layer (A)" above.

Especially for providing both fluid acquisition and distribution properties, the use of modified cellulosic fibers is preferred. Examples for modified cellulosic fibers are chemically treated cellulosic fibers, especially chemically stiffened cellulosic fibers. The term "chemically stiffened cellulosic fibers" means cellulosic fibers that have been stiffened by chemical means to increase the stiffness of the fibers. Such means include the addition of chemical stiffening agent in the form of surface coatings, surface cross-linking and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins.

Stiffening may also include altering the chemical structure, e.g. by crosslinking polymer chains. Thus crosslinking agents can be applied to the fibers that are caused to chemically form intrafiber crosslink bonds. Further cellulosic fibers may be stiffened by crosslink bonds in individualized form. Suitable chemical stiffening agents are typically monomeric crosslinking agents including $C_2$-$C_8$ dialdehyde, $C_2$-$C_8$ monoaldehyde having an acid functionality, and especially $C_2$-$C_9$ polycarboxylic acids.

Preferably the modified cellulosic fibers are chemically treated cellulosic fibers. Especially preferred are curly fibers which can be obtained by treating cellulosic fibers with citric acid. Preferably the basis weight of cellulosic fibers and modified cellulosic fibers is from 50 to 200 gsm.

Suitable acquisition-distribution layers further include synthetic fibers. Known examples of synthetic fibers are found in the Chapter "Liquid-pervious sheet or liquid pervious layer (A) above. Another possibility available is 3D-polyethylene film with dual function as a liquid-pervious layer (A) and acquisition-distribution layer.

Further, as in the case of cellulosic fibers, hydrophilic synthetic fibers are preferred. Hydrophilic synthetic fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious sheet or liquid pervious layer(A)" above.

Thus, suitable acquisition-distribution layers comprising from 80 to 100% by weight a fibrous material and from 0 to 20% by weight water-absorbent polymer particles;

Preferred acquisition-distribution layers show basis weights in the range from 20 to 200 gsm, most preferred in the range from 40 to 60 gsm.

Alternatively a liquid-impervious layer (D) comprising a synthetic resin film between (A) and (C) acting as an distribution layer and quickly transporting the supplied urine along the surface to the upper lateral portion of the fluid-absorbent core (C). Preferably, the upper liquid-impervious layer (D) is smaller than the under-laying fluid-absorbent core (C) (80). There is no limit in particular to the material of the liquid-impervious layer (D). Such a film made of a resin such as polyethylene, polypropylene, polyethylene therephthalate, polyurethane, or crosslinked polyvinyl alcohol and an air-permeable, but liquid-impervious, so-called: "breathable" film made of above described resin, may be used.

Preferably, the upper liquid-impervious layer (D) comprises a porous polyethylene film for both quick acquisition and distribution of fluid.

Alternatively a bundle of synthetic fibers acting as acquisition-distribution layer loosely distributed on top of the fluid-absorbent core may be used. Suitable synthetic fibers are of copolyester, polyamide, copolyamide, polylactic acid, polypropylene or polyethylene, viscose or blends thereof. Further bicomponent fibers can be used. The synthetic fiber component may be composed of either a single fiber type with a circular cross-section or a blend of two fibre types with different cross-sectional shapes. Synthetic fibers arranged in that way ensuring a very fast liquid transport and canalisation. Preferably bundles of polyethylene fibers are used.

An optional tissue layer is disposed immediately above and/or below (C).

The material of the tissue layer may comprise any known type of substrate, including webs, garments, textiles and films. The tissue layer may comprise natural fibers, such as cellulose, cotton, flax, linen, hemp, wool, silk, fur, hair and naturally occurring mineral fibers. The tissue layer may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose fibers.

Other Optional Components (F)

1. Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands.

Preferred are leg cuffs from synthetic fibers showing the layer combinations sms, smms or smsms. Preferred are nonwovens with the density of 13 to 17 gsm. Preferably leg cuffs are provided with two elastic strands.

2. Elastics

The elastics are used for securely holding and flexibly closing the fluid-absorbent article around the wearers' body, e.g. the waist and the legs to improve containment and fit. Leg elastics are placed between the outer and inner layers or the fluid-absorbent article, or between the outer garment facing cover and the user facing bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elastisized or shrunk, e.g. by the application of heat.

3. Closing System

The closing system can include tape tabs, landing zone, elastomerics, pull ups and the belt system or combinations thereof At least a part of the first waist region is attached to a part of the second waist region by the closing system to hold the fluid-absorbent article in place and to form leg openings and the waist of the fluid-absorbent article. Preferably the fluid-absorbent article is provided with a reclosable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations thereof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, polycarbonate, polyester, ethylene vinyl acetate, ethylene vinyl alcohol, ethylene vinyl acetate acrylate or ethylene acrylic acid copolymers.

Suitable closing systems comprise further a hook portion of a hook and loop fastener and the target devices comprise the loop portion of a hook and loop fastener.

Suitable mechanical closing systems including a landing zone. Mechanical closing systems may fasten directly into the outer cover. The landing zone may act as an area of the fluid-absorbent article into which it is desirable to engage the tape tabs. The landing zone may include a base material and a plurality of tape tabs. The tape tabs may be embedded in the base material of the landing zone. The base material may include a loop material. The loop material may include a backing material and a layer of a nonwoven spunbond web attached to the backing material.

Thus suitable landing zones can be made by spunbonding. Spunbonded nonwoven are made from melt-spun fibers formed by extruding molten thermoplastic material. Preferred is bi-oriented polypropylene (BOPP), or brushed/closed loop in the case of mechanical closing systems.

Further, suitable mechanical closing systems including elasticomeric units serving as a flexible abdominal and/or dorsal discrete waist band, flexible abdomen and/or dorsal zones located at distal edge for fluid-absorbents articles, such as pants or pull-ups. The elasticomeric units enable the fluid-absorbent article to be pulled down by the wearer as e.g. a training pant.

Suitable pants-shaped fluid-absorbent article has front abdominal section, rear dorsal section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer and offers improved mobility and discretion.

Suitable pull-ups comprising thermoplastic films, sheets and laminates having a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprising two elastic belts, a left elastic belt, and a right elastic belt. The left elastic belt is associated with each of the left angular edges. The right elastic belt associated with each of the right angular edges. The left and right side belts are elastically extended when the absorbent garment is laid flat. Each belt is connected to and extends between the front and rear of the fluid-absorbent article to form a waist hole and leg holes.

Preferably the belt system is made of elastomerics, thus providing a conformable fit of the fluid-absorbent article and maintaining adequate performance against leakage.

Preferred closing systems are so-called "elastic ears" attached with one side of the ear to the longitudinal side edges located at the rear dorsal longitudinal edge of the chassis of the fluid-absorbent article. Commercially available fluid-absorbent articles include stretchable ears or side panels which are made from a stretchable laminate e.g. nonwoven webs made of mono- or bi-component fibers. Especially preferred closing systems are stretchable laminates comprising a core of several layers each of different fibrous materials, e.g. meltblown fibers, spunbond fibers, containing multicomponent fibers having a core comprising a first polymer having a first melt temperature and a sheath comprising a second polymer having a second melt temperature; and a web of an elastomeric material as top and bottom surfaces to form said laminate.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

In order to immobilize the water-absorbent polymer particles, the adjacent layers are fixed by the means of thermoplastic materials, thereby building connections throughout the whole surface or alternatively in discrete areas of junction. For the latter case, cavities or pockets are built carrying the water-absorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between about 0.5 mm and 2 mm. Fluid-absorbent articles comprising areas of junction show a better wet strength.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by Bostik, Henkel or Fuller.

In order to ensure wicking of applied body fluids, preferred fluid-absorbent article show channels for better transport. Channels are formed by compressional forces of e.g. the top sheet against the fluid-absorbent core. Compressive forces may be applied e.g. by heat-treatment between two heated calendar rollers. As an effect of compression both on top sheet and fluid-absorbent core deform such that a channel is created. Body fluids are flowing along this channel to places where they are absorbed and leakage is prevented. Otherwise, compression leads to higher density; this is the second effect of the channel to canalize insulted fluids. Additionally, compressive forces on diaper construction improve the structural integrity of the fluid-absorbent article.

Typically fluid-absorbent articles according to the invention comprising,
(A) an upper liquid-pervious sheet,
(B) a lower liquid-impervious sheet,
(C) a fluid-absorbent core comprising from 60 to 20% by weight fibrous material and from 40 to 80% by weight of at least a first type of water-absorbent polymer particles (G) and at least a second type of water-absorbent polymer particles (H) based on the sum of water-absorbent polymer particles and fibrous material;
(D) an optional acquisition-distribution layer (D) between (A) and (C),
(F) other optional components,
wherein the first type of water absorbent polymer particles (G) of the fluid-absorbent core (C) have a SFC of at least $20 \times 10^{-7}$ cm$^3 \cdot$s/g and wherein the at least second type of water-absorbent polymer particles (H) of the fluid-absorbent core have a sphericity of at least 0.80.

According to the invention the second type of water-absorbent polymer particles has a SFC at maximum of $15 \times 10^{-7}$ cm$^3 \cdot$s/g.

The fluid-absorbing core (C) according to the invention may comprise at least two layers (K, L), wherein one of the layers (K) comprises from 60 to 20% by weight fibrous material and 40 to 80% by weight of the first type of water-absorbent polymer particles (G) based on the sum of water-absorbent polymer particles and fibrous material and the second layer (L) comprises from 60 to 20% by weight fibrous material and 40 to 80% by weight of the at least second type of water-absorbent polymer particles (H) based on the sum of water-absorbent polymer particles and fibrous material.

According to a preferred embodiment, in the fluid-absorbent core (C) the layer comprising the first type of water-absorbent polymer particles (G) is arranged in z-direction above the layer comprising the at least second type of water-absorbent polymer particles (H).

According to another embodiment the fluid-absorbent articles according to the invention comprising,
(A) an upper liquid-pervious sheet,
(B) a lower liquid-impervious sheet,
(C) a fluid-absorbent core comprising from 60 to 20% by weight fibrous material and from 40 to 80% by weight of a mixture of at least a first type of water-absorbent polymer particles (G) and at least a second type of water-absorbent polymer particles (H) based on the sum of water-absorbent polymer particles and fibrous material;
(D) an optional acquisition-distribution layer (D) between (A) and (C),
(F) other optional components,
wherein the first type of water absorbent polymer particles (G) of the fluid-absorbent core (C) have a SFC of at least 20×10-7 cm$^3 \cdot$s/g and wherein the at least second type of water-absorbent polymer particles (H) of the fluid-absorbent core have a mean sphericity of at least 0.80.

According to the invention the second type of water-absorbent polymer particles has a SFC at maximum of $15 \times 10^{-7}$ cm$^3 \cdot$s/g.

The inventive fluid-absorbent article shows improved rewet and fluid acquisition properties. According to the invention the production process of the first type of water absorbent polymer particles (G) of the fluid-absorbent core (C) comprises the steps of polymerization of the monomer solution, forming and comminuting a polymer gel, drying and grinding of the polymer. The resulting water absorbent polymer particles are therefore irregularly shaped.

According to a preferred embodiment of the invention the at least first type of water-absorbent polymer particles (G) and the at least second type of water-absorbent polymer particles (H) are present within the fluid-absorbent core (C) in equal amounts by weight.

Methods:

The measurements should, unless stated otherwise, be carried out at an ambient temperature of 23±2° C. and a relative atmospheric humidity of 50±10%. The water-absorbent polymers are mixed thoroughly before the measurement.

The "WSP" standard test methods are described in: "Standard Test Methods for the Nonwovens Industry", jointly issued by the "Worldwide Strategic Partners" EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is available both from EDANA and INDA.

Accelerated Aging Test

Measurement 1 (Initial color): A plastic dish with an inner diameter of 9 cm is overfilled with superabsorbent polymer particles. The surface is flattened at the height of the petri dish lip by means of a knife and the CIE color values and the HC 60 value are determined.

Measurement 2 (after aging): A plastic dish with an inner diameter of 9 cm is overfilled with superabsorbent polymer particles. The surface is flattened at the height of the petri dish lip by means of a knife. The plastic dish (without a cover) is then placed in a humidity chamber at 60° C. and a relative humidity of 86%. The plastic dish is removed from the humidity chamber after 7, and 14 days, cooled down to room temperature and the CIE color values are determined.

Absorbency Under No Load (AUNL)

The absorbency under no load of the water-absorbent polymer particles is determined analogously to the EDANA recommended test method No. WSP 242.3 (11) "Gravimetric Determination of Absorption Under Pressure", except using a weight of 0.0 $g/cm^2$ instead of a weight of 21.0 $g/cm^2$.

Absorbency Under Load (AUL)

The absorbency under load of the water-absorbent polymer particles is determined by the EDANA recommended test method No. WSP 242.3 (11) "Gravimetric Determination of Absorption Under Pressure"

Absorbency Under High Load (AUHL)

The absorbency under high load of the water-absorbent polymer particles is determined analogously to the EDANA recommended test method No. WSP 242.3 (11) "Gravimetric Determination of Absorption Under Pressure", except using a weight of 49.2 $g/cm^2$ instead of a weight of 21.0 $g/cm^2$.

Bulk Density

The bulk density of the water-absorbent polymer particles is determined by the EDANA recommended test method No. WSP 250.3 (11) "Gravimetric Determination of Density".

Centrifuge Retention Capacity (CRC)

The centrifuge retention capacity of the water-absorbent polymer particles is determined by the EDANA recommended test method No. WSP 241.3 (11) "Fluid Retention Capacity in Saline, After Centrifugation", wherein for higher values of the centrifuge retention capacity larger tea bags have to be used.

Color Value (CIE Color Numbers [L, a, b])

Measurement of the color value is done by means of a colorimeter model "LabScan XE S/N LX17309" (HunterLab; Reston; U.S.A.) according to the CIELAB procedure (Hunterlab, Volume 8, 1996, Issue 7, pages 1 to 4). Colors are described by the coordinates L, a, and b of a three-dimensional system. L characterizes the brightness, whereby L=0 is black and L=100 is white. The values for a and b describe the position of the color on the color axis red/green resp. yellow/blue, whereby positive a values stand for red colors, negative a values for green colors, positive b values for yellow colors, and negative b values for blue colors.

The measurement of the color value is in agreement with the tristimulus method according to DIN 5033-6.

Extractables

The level of extractable constituents in the water-absorbent polymer particles is determined by the EDANA recommended test method No. WSP 270.3 (11) "Extractables".

Free Swell Capacity (FSC)

The free swell capacity of the water-absorbent polymer particles is determined by the EDANA recommended test method No. WSP 240.3 (11) "Free Swell Capacity in Saline, Gravimetric Determination", wherein for higher values of the free swell capacity larger tea bags have to be used.

Free Swell Rate (FSR) 1.00 g (=W1) of the dry water-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR\ [g/gs] = W2/(W1 \times t)$$

When the moisture content of the hydrogel-forming polymer is more than 3% by weight, however, the weight W1 must be corrected for this moisture content.

Gel Bed Permeability

The gel bed permeability (GBP) of a swollen gel layer under a pressure of 0.3 psi (2070 Pa) is, as described in US 2005/0256757 (paragraphs [0061] and [0075]), determined as the gel bed permeability of a swollen gel layer of water-absorbing polymer particles.

Sphericity or Roundness

The roundness is determined with the PartAn® 3001 L Particle Analysator (Microtrac Europe GmbH; Meerbusch; Germany)

or with the Camsizer® image analysis system (Retsch Technolgy GmbH; Haan; Germany): For the measurement, the product is introduced through a funnel and conveyed to the falling shaft with a metering channel. While the particles fall past a light wall, they are recorded selectively by a camera. The images recorded are evaluated by the software in accordance with the parameters selected.

The parameters reported are the mean volume-weighted sphericities.

Moisture Content

The moisture content of the water-absorbent polymer particles is determined by the EDANA recommended test method No. WSP 430.2-05 "Moisture Content".

Particle Size Distribution

The particle size distribution of the water-absorbent polymer particles is determined by the EDANA recommended test method No. WSP 220.3 (11) "Particle Size Distribution".

The average particle diameter ($d_{50}$) here is the value of the mesh size which gives rise to a cumulative 50% by weight.

The degree of polydispersity α of the particle size particle is calculated by $$\beta(=(d_{84.13} - d_{15.87})/(2 \times d_{50})$$

wherein $d_{15.87}$ and $d_{84.13}$ is the value of the mesh size which gives rise to a cumulative 15.87% respective 84.13% by weight.

Rewet Under Load (RUL) and Acquisition Time

The test determines the amount of fluid a fluid-absorbent article will release after being maintained at a pressure of 0.7 psi (49.2 g/cm²) for 5 min following multiple separate insults. The rewet under load is measured by the amount of fluid the fluid-absorbent article releases under pressure. The rewet under load is measured after each insult.

The fluid-absorbent article is clamped nonwoven side upward onto the inspection table. The insult point (pee point) is marked accordingly with regard to the type and gender of the diaper to be tested (i.e. in the centre of the core for girl, 2.5 cm towards the front for unisex and 5 cm towards the front for boy). A 3.64 kg circular weight (10 cm diameter) having a central opening (2.3 cm diameter) with perspex tube is placed with on the previously marked insult point.

To measure the RUL for absorbent pads with an ADL on top, the pad is clamped ADL side upward onto the inspection table. The insult point (pee point) is marked accordingly with regard to the type and gender of the diaper to be tested (i.e. in the center of the core for girl, 2.5 cm towards the front for unisex and 5 cm towards the front for boy) For the primary insult 75 g of aqueous saline solution (0.9% by weight) is poured into the perspex tube in one shot. Amount of time needed for the fluid to be fully absorbed into the fluid-absorbent article is recorded—it is an acquisition time, reported in seconds. After 5 minutes have elapsed, the load is removed and the stack of 10 filter papers (Whatman®) having 9 cm diameter and known dry weight (W1) is placed over the insult point on the fluid-absorbent article or the absorbent pad with ADL respectively. On top of the filter paper, the 2.5 kg weight with 8 cm diameter is added. After 2 minutes have elapsed the weight is removed and filter paper reweighed giving the wet weight value (W2).

The rewet under load is calculated as follows:

RUL [g]=$W2-W1$

For the rewet under load of the secondary and following insults the procedure for the primary insult is repeated. For each following insults 2", 3" and 4" 75 g of aqueous saline solution (0.9% by weight) and 20, 30, 40 filter papers respectively are used.

Residual Monomers

The level of residual monomers in the water-absorbent polymer particles is determined by the EDANA recommended test method No. WSP 210.3-(11) "Residual Monomers".

Saline Flow Conductivity (SFC)

The saline flow conductivity (SFC) of a swollen gel layer under a pressure of 0.3 psi (2070 Pa) is, as described in EP 0 640 330 A1, determined as the gel layer permeability of a swollen gel layer of water-absorbing polymer particles, the apparatus described on page 19 and in FIG. 8 in the cited patent application having been modified such that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

SFC [cm³·s/g]=$(Fg(t=0) \times L0)/(d \times A \times WP)$ where $Fg(t=0)$ is the flow of NaCl solution in g/s, which is obtained using linear regression analysis of the $Fg(t)$ data of the flow determinations by extrapolation to $t=0$, L0 is the thickness of the gel layer in cm, d is the density of the NaCl solution in g/cm³, A is the area of the gel layer in cm², and WP is the hydrostatic pressure over the gel layer in dyn/cm².

Vortex 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of water-absorbent polymer particles are added to the beaker as quickly as possible, starting a stop watch as addition begins. The stopwatch is stopped when the surface of the mixture becomes "still" that means the surface has no turbulence, and while the mixture may still turn, the entire surface of particles turns as a unit. The displayed time of the stopwatch is recorded as Vortex time.

The EDANA test methods are obtainable, for example, from the EDANA, Avenue Eugene Plasky 157, B-1030 Brussels, Belgium.

EXAMPLES

Preparation of the Fluid-Absorbent Polymer Particles
The following polymer particles are used:
Water-absorbent polymer particles prepared as described in Example 4
Water-absorbent polymer particles prepared as described in Example 5
Water-absorbent polymer particles prepared as described in Example 6
Water-absorbent polymer particles as described in Example 7
HySorb® B7085 available from BASF Antwerpen N.V., Belgium
Hysorb® B7160S available from BASF Antwerpen N.V., Belgium Features and absorption profiles of all polymer particles are summarized in Table 9.

Example 1—Basepolymer

The process was performed in a concurrent spray drying plant with an integrated fluidized bed (27) as shown in FIG. 1. The reaction zone (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

The temperature of the gas leaving the reaction zone (5) was measured at three points around the circumference at the end of the cylindrical part of the spray dryer as shown in FIG. 3. Three single measurements (43) were used to calculate the average temperature (spray dryer outlet temperature). The drying gas loop was heated up and the dosage of monomer solution is started up. From this time the spray dryer outlet temperature was controlled to 122° C. by adjusting the gas inlet temperature via the heat exchanger (20). The gas inlet temperature was 167° C. and the steam content of the drying gas is shown in Tab. 1.

The product accumulated in the internal fluidized bed (27) until the weir height was reached. Conditioned internal fluidized bed gas having a temperature of 112° was fed to the internal fluidized bed (27) via line (25). The gas velocity of the internal fluidized bed gas in the internal fluidized bed

(27) was 0.65 m/s. The residence time of the product was 150 min. The temperature of the water-absorbent polymer particles in the internal fluidized bed (27) was 80° C.

The spray dryer offgas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in Tab. 1. The water inside the condenser column (12) was set to an alkaline pH by dosing sodium hydroxide solution to wash out acrylic acid vapors.

The gas leaving the condenser column (12) was split to the drying gas inlet pipe (37) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm. The weight amounts of overs/lumps are summarized in Tab. 3.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 1. Sodium peroxodisulfate solution having a temperature of 20° C. was added via line (33) and [2,2'-azobis[2-(2-imidazolin-2-yl)propane]dihydrochloride solution together with Brüggolite® FF7 and Blancolen® HP having a temperature of 10° C. was added via line (34). Each initiator was pumped in a loop and dosed via control valves to each dropletizer unit. A second filter unit having a mesh size of 140 μm was used after the static mixer (32). For dosing the monomer solution into the top of the spray dryer three dropletizer units were used as shown in FIG. 4.

A dropletizer unit consisted of an outer pipe (47) having an opening for the dropletizer cassette (49) as shown in FIG. 7. The dropletizer cassette (49) was connected with an inner pipe (48). The inner pipe (48) having a PTFE block (50) at the end as sealing can be pushed in and out of the outer pipe (47) during operation of the process for maintenance purposes.

The temperature of the dropletizer cassette (49) was controlled to 8° C. by water in flow channels (55) as shown in FIG. 8. The dropletizer cassette (49) had 256 bores having a diameter of 170 μm and a bore spacing of 15 mm. The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°. The droplet plate (53) was made of stainless steel and had a length of 630 mm, a width of 128 mm and a thickness of 1 mm.

The feed to the spray dryer consisted of 9.56% by weight of acrylic acid, 33.73% by weight of sodium acrylate, 0.011% by weight of 3-tuply ethoxylated glycerol Triacrylate (purity approx. 85% by weight), 0.071% by weight of [2,2'-azobis[2-(2-imidazolin-2-yl)propane]dihydrochloride, 0.0028% by weight of Brüggolite® FF7 (Brüggolite Chemicals; Heilbronn; Germany), 0.071% by weight of Blancolene® HP (Brüggolite Chemicals; Heilbronn; Germany) 0.054% by weight of sodiumperoxodisulfate and water. The degree of neutralization was 73%. The feed per bore was 1.4 kg/h.

The resulting water-absorbent polymer particles were analyzed. The conditions and results are summarized in Tab. 1 to 3.

Example 2 Basepolymer

The process was performed in a concurrent spray drying plant with an integrated fluidized bed (27) as shown in FIG. 1. The reaction zone (5) had a height of 22 m and a diameter of 3.4 m. The internal fluidized bed (IFB) had a diameter of 3 m and a weir height of 0.25 m.

The drying gas was feed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

The temperature of the gas leaving the reaction zone (5) was measured at three points around the circumference at the end of the cylindrical part of the spray dryer as shown in FIG. 3. Three single measurements (43) were used to calculate the average temperature (spray dryer outlet temperature). The drying gas loop was heated up and the dosage of monomer solution is started up. From this time the spray dryer outlet temperature was controlled to 112° C. by adjusting the gas inlet temperature via the heat exchanger (20). The gas inlet temperature was 167° C. and the steam content of the drying gas is shown in Tab. 1.

The product accumulated in the internal fluidized bed (27) until the weir height was reached. Conditioned internal fluidized bed gas having a temperature of 107° was fed to the internal fluidized bed (27) via line (25). The gas velocity of the internal fluidized bed gas in the internal fluidized bed (27) was 0.65 m/s. The residence time of the product was 150 min. The temperature of the water-absorbent polymer particles in the internal fluidized bed (27) was 77° C.

The spray dryer offgas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in Tab. 1. The water inside the condenser column (12) was set to an alkaline pH by dosing sodium hydroxide solution to wash out acrylic acid vapors.

The gas leaving the condenser column (12) was split to the gas drying unit (37) and the conditioned internal fluidized bed gas (25). The gas drying unit (37) comprises a gas cooler and a demister. In the gas drying unit (37) the gas was cooled down to 40° C. and heated up prior to the drying gas inlet pipe (1). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm. The weight amounts of overs/lumps are summarized in Tab. 3.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 1. Sodium peroxodisulfate solution having a temperature of 20° C. was added via line (33) and [2,2'-azobis[2-(2-imidazolin-2-yl)propane]dihydrochloride solution together with Brüggolite® FF7 having a temperature of 5° C. was added via line (34). Each initiator was pumped in a loop and dosed via control valves to each dropletizer unit. A second filter unit having a mesh size of 140 μm was used after the static mixer (32). For dosing the monomer solution into the top of the spray dryer three dropletizer units were used as shown in FIG. 4.

A dropletizer unit consisted of an outer pipe (47) having an opening for the dropletizer cassette (49) as shown in FIG. 7. The dropletizer cassette (49) was connected with an inner pipe (48). The inner pipe (48) having a PTFE block (50) at the end sealing can be pushed in and out of the outer pipe (47) during operation of the process for maintenance purposes.

The temperature of the dropletizer cassette (49) not cooled by water flow channels (55) as shown in FIG. 8. The dropletizer cassette (49) had 256 bores having a diameter of 170 μm and a bore spacing of 15 mm. The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°. The droplet plate (53) was made of stainless steel and had a length of 630 mm, a width of 128 mm and a thickness of 1 mm.

The feed to the spray dryer consisted of 9.3% by weight of acrylic acid, 33.4% by weight of sodium acrylate, 0.013% by weight of 3-tuply ethoxylated glycerol triacrylate, 0.054% by weight of [2,2'-azobis[2-(2-imidazolin-2-yl)propane]dihydrochloride, 0.0018% by weight of Brüggolite FF7, 0.072% by weight of sodiumperoxodisulfate, 0.072% by weight 1-hydroxyethanediphosphonic acid sodium salt and water. The degree of neutralization was 73%. The feed per bore was 1.4 kg/h.

The resulting water-absorbent polymer particles were analyzed. The trial conditions and results are summarized in Tab. 1 to 3.

Examples 3 Basepolymer

The example was performed analogous to example 2, except that 0.108% by weight of 1-hydroxyethanediphosphonic acid sodium salt was used instead of 0.072% by weight of 1-hydroxyethanediphosphonic acid sodium salt. The resulting water-absorbent polymer particles were analyzed. The trial conditions and results are summarized in Tab. 1 to 3.

TABLE 1

Process conditions of the polymerization for examples 1-3

| Example | Steam Content CC kg/kg | Steam Content GD kg/kg | T gas inlet °C. | T gas outlet °C. | T gas IFB °C. | T IFB °C. | T CC °C. | T GDU °C. |
|---|---|---|---|---|---|---|---|---|
| 1 | 0.1100 | 0.0651 | 167 | 122 | 112 | 80 | 54 | 45 |
| 2 | 0.1100 | 0.0651 | 167 | 112 | 107 | 77 | 54 | 45 |
| 3 | 0.1100 | 0.0651 | 167 | 112 | 107 | 77 | 54 | 45 |

Steam Content CC: steam content of the gas leaving the condenser column (12)
Steam Content GD: steam content of the gas prior to the gas distributor (3)
T gas inlet: temperature of the gas prior to the gas distributor (3)
T gas outlet: temperature of the gas leaving the reaction zone (5)
T gas IFB: temperature of the gas entering the internal fluidized bed (27) via line (25)
T IFB: temperature of the water-absorbent polymer particles in the fluidized bed (27)
T CC: temperature of the gas leaving the condenser column (12)
T GDU: temperature of the gas leaving the gas drying unit (37)

TABLE 2

Properties of the water-absorbent polymer particles (base polymers) prepared in examples 1-3.

| Example Unit | Bulk Density g/cm³ | CRC g/g | AUL g/g | Residual Monomers Ppm | Extractables wt. % | Moisture wt. % |
|---|---|---|---|---|---|---|
| 1 | 62.5 | 69.8 | 7.5 | 6300 | 11.8 | 8.2 |
| 2 | 70.0 | 49.7 | 9.4 | 6400 | 5.6 | 9.2 |
| 3 | 70.1 | 49.6 | 9.3 | 8100 | 5.3 | 9.0 |

TABLE 3

Particles Size Distribution (PSD) of the water-absorbent polymer particles (base polymers) prepared in examples 1-3, measured by sieve fraction analysis

| Example unit | 0-100 μm wt % | 100-200 μm wt % | 200-250 μm wt % | 250-300 μm wt % | 300-400 μm wt % | 400-500 μm wt % | 500-600 μm wt % | 600-850 μm wt % | 850-1000 μm wt % | >1000 μm wt % |
|---|---|---|---|---|---|---|---|---|---|---|
| 1 | 0.0 | 0.5 | 3.3 | 6.7 | 26.3 | 31.9 | 17.1 | 13.3 | 0.8 | 0.1 |
| 2 | 0.0 | 0.6 | 3.1 | 6.1 | 34.2 | 38.8 | 11.6 | 5.1 | 0.4 | 0.1 |
| 3 | 0.1 | 0.7 | 2.6 | 6.0 | 33.4 | 37.7 | 12.5 | 6.5 | 0.4 | 0.1 |

Example 4

General Description of Surface Crosslinking

In a Schugi Flexomix® (model Flexomix 160, manufactured by Hosokawa Micron B.V., Doetinchem, the Netherlands) with a speed of 2000 rpm, the water absorbent base polymer was coated with a surface-postcrosslinker solution by using 3 round spray nozzle systems (model Gravity-Fed Spray Set-ups, External Mix Typ SU4, Fluid Cap 60100 and Air Cap SS-120, manufactured by Spraying Systems Co, Wheaton, Illinois, USA) and then filled via base polymer feed (70) and dried in a thermal dryer (65) (model NPD 5W-18, manufactured by GMF Gouda, Waddinxveen, the Netherlands) with a speed of the shaft (76) of 6 rpm. The thermal dryer (65) has two paddles with a shaft offset of 90° (80) and a fixed discharge zone (71) with two flexible weir plates (73). Each weir has a weir opening with a minimal weir height at 50% (75) and a maximal weir opening at 100% (74) as shown in FIG. 15.

The inclination angle α (78) between the floor plate and the thermal dryer was approx. 3°. The weir height of the thermal dryer was between 50 to 100%, corresponding to a residence time of approx. 40 to 150 min, by a product density of approx. 700 to 750 kg/m³. The product temperature in the thermal dryer was in a range of 120 to 165° C. After drying, the surface-postcrosslinked polymer was transported over discharge cone (77) in a cooler (model NPD 5W-18, manufactured by GMF Gouda, Waddinxveen, the Netherlands), to cool down the surface postcrosslinked polymer to approx. 60° C. with a speed of 11 rpm and a weir height of 145 mm.

Surface Crosslinking of Base Polymer Prepared in Example 1

Ethylene carbonate, water, Span® 20 (Croda, Nettetal, Germany)), aqueous aluminum lactate (22% by weight) were premixed and used as surface-postcrosslinker solution as summarized in Tab. 5. As aluminum lactate, Lothragon® AI 220 (manufactured by Dr. Paul Lohmann GmbH, Emmerthal, Germany) was used.

4.3 wt % of a 0.05% aqueous solution of Plantacare® 818 UP solution (dry, manufactured by BASF SE) and 4.3 wt % of a 0.025% aqueous solution of Plantacare® 818 UP were additionally added into the cooler using two nozzles in the first third of the cooler. Both solution having a temperature of approx. 25° C. The nozzles were placed below the product bed.

After cooling, the material was sieved with a minimum cut size of 150 μm and a maximum cut size of 850 μm.

The resulting water-absorbent polymer particles were analyzed. The trial conditions and results are summarized in Tab. 4 to 8.

Example 5 and 6

Surface Crosslinking of Base Polymer Prepared in Example 2 and 3

Ethylene carbonate, water and an aqueous aluminum sulfate solution (26.8% by weight) were premixed and spray coated as summarized in Tab. 5b. 2.324 wt % of a 0.0538% aqueous solution of Span®20 solution and 2.325 wt % of water was additionally added into the cooler using two nozzles in the first third of the cooler. Both solution having a temperature of approx. 25° C. The nozzles were placed below the product bed.

The metered amounts and conditions of the coating into the Schugi Flexomix®, the conditions, the formulation and values of the drying and cooling step are summarized in Table 4.

After cooling, the material was sieved with a minimum cut size of 150 μm and a maximum cut size of 710 μm.

All physical properties of the resulting polymers are summarized in Table 6 to 8:

TABLE 4

Process conditions of the thermal dryer for the surface postcrosslinking (SXL)

| Example Unit | Product Temp. Set Value ° C. | Steam Pressure Wave Bar | Steam Pressure Jacket Bar | Heater T1 ° C. | Heater T2 ° C. | Heater T3 ° C. | Heater T4 ° C. | Heater T5 ° C. | Heater T6 ° C. | Throughput kg/h | Heater Weir % | No. of Nozzles | Pos. of Nozzles |
|---|---|---|---|---|---|---|---|---|---|---|---|---|---|
| 4 | 140 | 3.7 | 3.6 | 76 | 104 | 119 | 129 | 130 | 140 | 470 | 80 | 3 | 90/180/270° |
| 5 | 170 | 9.0 | 9.0 | 95 | 100 | 121 | 144 | 160 | 170 | 470 | 80 | 3 | 90/180/270° |
| 6 | 158 | 6.7 | 6.7 | 90 | 94 | 119 | 136 | 149 | 158 | 470 | 80 | 3 | 90/180/270° |

TABLE 5 a)

Surface-postcrosslinker formulation of the thermal treatment in the heater and remoistening in the cooler

| | | SXL | | | | Cooler | |
| | | | | | | 0.05 wt % | 0.025 wt % |
| Example | Base polymer | EC bop % | Water bop % | Al-lactate (dry) bop % | Plantacare ® UP 818 (dry) bop ppm | aq. solution of Plantacare ® UP 818 (dry) bop % | aq. solution of Plantacare ® UP 818 (dry) bop % |
|---|---|---|---|---|---|---|---|
| 4 | Example 1 | 2.0 | 5.0 | 0.2 | 25 | 4.3 | 4.3 |

EC: Ethylene carbonate;
bop: based on polymer

TABLE 5 b)

Surface-postcrosslinker formulation of the thermal treatment in the heater

| Example | Base polymer | EC (SXL) wt. % bop | Water (SXL) wt. % bop | Al-Sulfate (dry) (SXL) ppm bop | aq. Span ®20 solution (0.05377% wt %) (Cooler) wt. % bop | Water (Cooler) wt. % bop |
|---|---|---|---|---|---|---|
| 5 | 2 | 2.0 | 5.0 | 0.2 | 2.325 | 2.325 |
| 6 | 3 | 2.0 | 5.0 | 0.2 | 2.325 | 2.325 |

TABLE 6

Physical properties of the polymer particles after surface-postcrosslinking

| Example | CRC g/g | AUL g/g | AUHL g/g | SFC $10^{-7}$ cm$^3$·s/g | Residual Monomers ppm | Extractables % | Bulk Density g/100 ml |
|---|---|---|---|---|---|---|---|
| 4 | 54.1 | 32.7 | 11.7 | 0 | 739 | 6.5 | 76 |
| 5 | 32.7 | 30.6 | 25.2 | 32 | 388 | 3.1 | 78.6 |
| 6 | 40.7 | 33.8 | 24.5 | 5 | 375 | 2.2 | 78.1 |

TABLE 7

Particle size distribution of the polymer particles after surface-postcrosslinking - Sieve fractions

| Example | <150 µm % | >150 µm % | >200 µm % | >250 µm % | >300 µm % | >400 µm % | >500 µm % | >600 µm % | >710 µm % |
|---|---|---|---|---|---|---|---|---|---|
| 4 | 0.1 | 0.4 | 2.3 | 5.9 | 32.5 | 35.3 | 16.9 | 5.7 | 0.9 |
| 5 | 0.1 | 1.0 | 2.9 | 7.8 | 36.7 | 38.1 | 10.2 | 3.0 | 0.2 |
| 6 | 0.2 | 1.0 | 2.7 | 7.8 | 36.7 | 37.5 | 9.6 | 3.7 | 0.9 |

TABLE 8

Color stability of the polymer particles after surface-postcrosslinking (Accelerated Aging Test)

| | 0 d | | | 7 d | | | 14 d | | | 21 d | | |
|---|---|---|---|---|---|---|---|---|---|---|---|---|
| Example | L | A | B | L | a | b | L | a | b | L | a | b |
| 4 | 94.1 | −1.7 | 7.8 | 86.7 | −1.3 | 7.7 | 85.2 | −1.3 | 8.5 | 83.0 | −1.2 | 9.0 |
| 5 | 91.7 | −0.4 | 8.9 | 72.7 | 4.4 | 12.6 | 64.5 | 6.6 | 15.0 | — | — | — |
| 6 | 92.3 | −0.4 | 8.5 | 79.9 | 1.8 | 11.2 | 76.5 | 2.9 | 12.6 | — | — | — |

Example 7

Water-absorbent polymer particles that are prepared in accordance to Example 25 of WO 2013/007819 A1.

TABLE 9

Physical properties of the polymer particles used for absorbent core preparation.

| SAP | FSC (g/g) | CRC (g/g) | AUNL 0.0 psi (g/g) | AUL 0.3 psi (g/g) | AUHL 0.7 psi (g/g) | SFC ($10^{-7}$ cm$^3$s/g) |
|---|---|---|---|---|---|---|
| HySorb ® B7085 | 46.3 | 29.0 | 42.2 | 28.9 | 22.5 | 26 |
| HySorb ® B7160S | 50.6 | 30.6 | 43.4 | 29.1 | 22.9 | 31 |
| example 4 | 67.6 | 54.0 | 64.6 | 32.7 | 11.7 | 0 |
| example 5 | 51.1 | 32.7 | 48.3 | 30.6 | 25.2 | 32 |
| example 6 | 62.9 | 40.7 | 56.0 | 33.8 | 24.5 | 5 |
| example 7 | 47.2 | 26.2 | 40.4 | 28.3 | 24.4 | 120 |

The fluid-absorbent particles of examples 4, 5, and 6 have a roundness or sphericity of at least 0.8.

Preparation of the Fluid-Absorbent Pad

Example 8 Fluid-Absorbent Pad—Dual Core

The fluid-absorbent pad comprises single core system with two SAP layers. The core has a rectangular size of 41 cm×10 cm. The fluid-absorbent pad comprises a multi-layered system of spunbond layer coverstock as top sheet (A), layered, high loft acquisition distribution layer (D) and fluid absorbent core (C) made of fluff/SAP mixtures.

The fluid absorbent core has layered structure comprising 2 different SAP types uniformly distributed within fluff fibers. Bottom layer of absorbent core holds 6.5 g uniformly distributed fluid-absorbent polymer particles from example 6, whereas top layer holds commercially available Hysorb®7085.

The total weight of fluff pulp (cellulose fibers) in the core is 7 g. The density of the fluid-absorbent core is in average 0.25-0.30 g/cm$^3$. The basis weight of the core is 488 g/m$^2$. The fluid-absorbent core holds 65% by weight fluid-absorbent polymer particles distributed within 2 layers, total quantity of the fluid-absorbent polymer particles within the fluid-absorbent core is 13 g.

As an acquisition-distribution layer, Multifunctional Acquitex (Texsus, Italy) having basis weight of 60 g/m$^2$ was used. The acquisition-distribution layer (D) is rectangular shaped of a size of 16 cm×9 cm and placed on the absorbent core that way, that the middle point of the ADL covers the pee point. The pee point is marked 2.5 cm towards the front from the center of the absorbent core.

Example 9

A fluid-absorbent pad of Example 8 was repeated, except that a fluid absorbent polymer particles in the bottom layer of the fluid absorbent core were replaced by the fluid absorbent polymer particles described in example 4.

Example 10—Fluid-Absorbent Pad—Core with Mixed SAP

Prior preparation of the fluid absorbent core, two types of fluid absorbent polymer were mixed in given proportions in Turbula® Mixer, type T2F (Willy A. Bachofen AG Maschinenfabrik Switzerland) for 5 min at speed 49 rotations per minute. Physical properties of such prepared fluid absorbent polymer mixtures were measured and are summarized in Table 10. The fluid absorbent polymer mixtures were used directly after mixing for fluid-absorbent pad preparation.

TABLE 10

Physical properties of the fluid absorbent polymer mixtures used for absorbent core preparation.

| SAP mixtures | ratio | FSC (g/g) | CRC (g/g) | AUNL 0.0 psi (g/g) | AUL 0.3 psi (g/g) | AUHL 0.7 psi (g/g) | SFC ($10^{-7}$ cm$^3$s/g) |
|---|---|---|---|---|---|---|---|
| Hysorb ® B7085 & example 6 | 1:1 | 55.8 | 35.1 | 49 | 31.1 | 22.2 | 20 |
| example 7 & example 6 | 1:1 | 55.1 | 31.7 | 47.7 | 30.6 | 24.7 | 20 |
| Hysorb ® B7160S & example 6 | 1:2 | 60.1 | 36.4 | 51.2 | 32.2 | 22.5 | 10 |
| Hysorb ® B7160S & example 6 | 1:1 | 56.1 | 34.9 | 49.2 | 31.2 | 23.4 | 12 |
| Hysorb ® B7160S & example 6 | 2:1 | 54.2 | 34.1 | 47.5 | 30.7 | 22.8 | 16 |
| example 4 & example 5 | 1:2 | 56.5 | 37.9 | 53.3 | 32.8 | 24.1 | — |
| example 4 & example 5 | 1:1 | 60 | 40.6 | 56.4 | 33.7 | 23.5 | 0 |
| example 4 & example 5 | 2:1 | 61.8 | 45.8 | 58 | 34.9 | 21.9 | — |

The fluid-absorbent pad comprises single core system having a rectangular size of 41 cm×10 cm. The fluid-absorbent pad comprises a multi-layered system of spunbond layer coverstock as top sheet (A), layered, high loft acquisition distribution layer (D) and fluid absorbent core (C) made of fluff/SAP mixtures.

The total weight of fluff pulp (cellulose fibers) is 7 g. The density of the fluid-absorbent core is in average 0.25-0.30 g/cm$^3$. The basis weight of the core is 488 g/m$^2$. The fluid-absorbent core holds 65% by weight uniformly distributed fluid-absorbent polymer mixture comprising particles from example 6 and particles of HySorb® B7085 (mixed in proportion 1:1). The total quantity of the fluid-absorbent polymer particles within the fluid-absorbent core is 13 g.

As an acquisition-distribution layer, Multifunctional Acquitex (Texsus, Italy) having basis weight of 60 g/m$^2$ was used. The acquisition-distribution layer is rectangular shaped of a size of 16 cm×9 cm and placed on the absorbent core that way, that the middle point of the ADL covers the pee point. The pee point is marked 2.5 cm towards the front from the center of the absorbent core.

Example 11

A fluid-absorbent pad of Example 10 was repeated, except that a fluid absorbent polymer mixture used for fluid-absorbent core preparation, contains particles prepared as described in example 7 and in example 6 (mixed in proportion 1:1).

Example 12

A fluid-absorbent pad of Example 10 was repeated, except that a fluid absorbent polymer mixture used for fluid-absorbent core preparation, contains particles prepared as described in example 6 and particles of Hysorb® B7160S.

The fluid absorbent polymers from example 6 and Hysorb® B7160S were mixed in following proportions:

Example 12 a) Hysorb® B7160S: example 6, mixed 1:2
Example 12 b) Hysorb® B7160S: example 6, mixed 1:1
Example 12 c) Hysorb® B7160S: example 6, mixed 2:1

Example 13

A fluid-absorbent pad of Example 10 was repeated, except that a fluid absorbent polymer mixture used for fluid-absorbent core preparation, contains particles prepared as described in example 4 and in example 5

The fluid absorbent polymers from example 4 and example 5 were mixed in following proportions:

Example 13 a) example 4: example 5, mixed 1:2
Example 13 b) example 4: example 5, mixed 1:1
Example 13 c) example 4: example 5, mixed 2:1

Example 14

A fluid-absorbent pad of Example 10 was repeated, except that a fluid absorbent polymer mixture used for fluid-absorbent core preparation, contains particles of HySorb® B7085 and particles prepared as described in example 4 (mixed in proportion 1:1).

Example 15—Comparative—Fluid-Absorbent Pad—Core with Single SAP

The fluid-absorbent pad comprises single core system having a rectangular size of 41 cm×10 cm. The fluid-absorbent pad comprises a multi-layered system of spun-bond layer coverstock as top sheet (A), layered, high loft acquisition distribution layer (D) and fluid absorbent core (C) made of fluff/SAP mixtures.

The total weight of fluff pulp (cellulose fibers) is 7 g. The density of the fluid-absorbent core is in average 0.25-0.30 g/cm$^3$. The basis weight of the core is 488 g/m$^2$. The fluid-absorbent core holds 65% by weight uniformly distributed fluid-absorbent polymer particles of HySorb® B7085; the quantity of the fluid-absorbent polymer particles within the fluid-absorbent core is 13 g.

As an acquisition-distribution layer, Multifunctional Acquitex (Texsus, Italy) having basis weight of 60 g/m$^2$ was used. The acquisition-distribution layer is rectangular shaped of a size of 16 cm×9 cm and placed on the absorbent core that way, that the middle point of the ADL covers the pee point. The pee point is marked 2.5 cm towards the front from the center of the absorbent core.

Example 16—Comparative, Core with Single SAP

A fluid-absorbent pad of Example 15 was repeated, except that a fluid absorbent polymer particles of HySorb® B7085 were replaced by the fluid absorbent polymer particles described in example 6.

Example 17—Comparative, Core with Single SAP

A fluid-absorbent pad of Example 15 was repeated, except that a fluid absorbent polymer particles of HySorb® B7085 were replaced by the fluid absorbent polymer particles described in example 4.

Example 18—Comparative, Core with Single SAP

A fluid-absorbent pad of Example 15 was repeated, except that a fluid absorbent polymer particles of HySorb® B7085 were replaced by the fluid absorbent polymer particles described in example 7.

Example 19—Comparative, Core with Single SAP

A fluid-absorbent pad of Example 15 was repeated, except that a fluid absorbent polymer particles of HySorb® B7085 were replaced by the fluid absorbent polymer particles of HySorb® B7160S.

Example 20—Comparative, Core with Single SAP

A fluid-absorbent pad of Example 15 was repeated, except that a fluid absorbent polymer particles of HySorb® B7085 were replaced by the fluid absorbent polymer particles of example 5.

Acquisition time under load and rewet value of the fluid absorbent pads from examples 8-20 were determined and results are summarized in Table 11, 12 and 13.

TABLE 11

| Rewet under load, acquisition times for each liquid insult into the pads with dual core | | | | | | | | | | |
|---|---|---|---|---|---|---|---|---|---|---|
| | | REWET UNDER LOAD [g] | | | | | Liquid Acquisition Time | | | |
| Example | SAP type | RUL 1 | RUL 2 | RUL 3 | RUL 4 | ΣRUL 1-4 [g] | A1 [s] | A2 | A3 | A4 | ΣA1-A4 [s] |
| ex. 8 | Hysorb ®7085/ example 6 | 0.06 | 0.10 | 0.58 | 6.77 | 7.51 | 62 | 92 | 105 | 110 | 369 |
| ex. 9 | Hysorb ®7085/ example 4 | 0.05 | 0.08 | 0.42 | 5.07 | 5.62 | 68 | 103 | 115 | 124 | 410 |

TABLE 12

Rewet under load, acquisition times for each liquid insult into the pads with core consisting mix SAPs

| Example | SAP mix | ratio | REWET UNDER LOAD [g] | | | | | Liquid Acquisition Time [s] | | | | |
|---|---|---|---|---|---|---|---|---|---|---|---|---|
| | | | RUL 1 | RUL 2 | RUL 3 | RUL 4 | ΣRUL 1-4 [g] | A1 | A2 | A3 | A4 | ΣA1-A4 [s] |
| ex. 10 | Hysorb ®7085/ example 6 | 1:1 | 0.05 | 0.19 | 1.85 | 8.77 | 10.86 | 62 | 90 | 102 | 107 | 361 |
| ex. 11 | example 6/ example 7 | 1:1 | 0.1 | 0.7 | 5.1 | 19.1 | 25 | 57 | 86 | 100 | 105 | 348 |
| ex. 12a | Hysorb ® B7160S/ example 6 | 1:2 | 0.06 | 2.02 | 6.61 | 14.98 | 23.67 | 63 | 98 | 112 | 112 | 385 |
| ex. 12b | Hysorb ® B7160S/ example 6 | 1:1 | 0.07 | 1.38 | 7.10 | 14.33 | 22.88 | 63 | 94 | 104 | 109 | 370 |
| ex. 12c | Hysorb ® B7160S/ example 6 | 2:1 | 0.05 | 2.19 | 7.38 | 19.28 | 28.9 | 64 | 99 | 108 | 114 | 385 |
| ex. 13a | example 4/ example 5 | 1:2 | 0.06 | 0.18 | 0.55 | 9.20 | 9.99 | 63 | 101 | 108 | 118 | 390 |
| ex. 13b | example 4/ example 5 | 1:1 | 0.07 | 0.22 | 0.47 | 5.85 | 6.61 | 64 | 111 | 118 | 128 | 421 |
| ex. 13c | example 4/ example 5 | 2:1 | 0.12 | 0.12 | 0.39 | 3.38 | 4.01 | 68 | 112 | 123 | 133 | 436 |
| ex. 14 | Hysorb ®7085/ example 4 | 1:1 | 0.22 | 2.02 | 6.14 | 13.98 | 22.36 | 66 | 103 | 113 | 121 | 403 |

TABLE 13

Rewet under load, acquisition times for each liquid insult into the pads with cores consisting single SAP type

| Example | SAP type | REWET UNDER LOAD [g] | | | | | Liquid Acquisition Time [s] | | | | ΣA1-A4 [s] |
|---|---|---|---|---|---|---|---|---|---|---|---|
| | | RUL 1 | RUL 2 | RUL 3 | RUL 4 | ΣRUL1-4 [g] | A1 | A2 | A3 | A4 | |
| ex. 15 | HySorb ® B7085 | 0.08 | 1.56 | 9.7 | 23.7 | 34.04 | 63 | 89 | 104 | 110 | 366 |
| ex. 16 | example 6 | 0.07 | 0.32 | 5.6 | 15.3 | 21.29 | 66 | 102 | 111 | 113 | 392 |
| ex. 17 | example 4 | 0.07 | 0.14 | 0.5 | 3.5 | 4.21 | 80 | 138 | 138 | 154 | 510 |
| ex. 18 | example 7 | 0.05 | 2.02 | 9.2 | 23.9 | 35.17 | 63 | 106 | 119 | 129 | 417 |
| ex. 19 | HySorb ® B7160S | 0.07 | 5.41 | 13.1 | 19.1 | 37.68 | 66 | 97 | 114 | 118 | 395 |
| ex. 20 | example 5 | 0.05 | 0.33 | 3.7 | 17.2 | 21.28 | 67 | 117 | 117 | 123 | 424 |

The above examples clearly show that dual cores with permeable fluid-absorbent particles on top layer and high capacity SAP in bottom layer, as well as cores with mixed fluid-absorbent polymer particles exhibit positive synergies in pads' performance and so in performance of the fluid-absorbent article. They show a fast acquisition time under load and better dryness comparing to the single SAP loaded pads with corresponding fluid-absorbent polymer particles. In addition, the examples show that despite the choice of the SAP their mixing ratio contributes to better performance of the pads comparing to the single SAP loaded pads with corresponding fluid-absorbent polymer particles.

The invention claimed is:

1. A fluid absorbent article, comprising
   (A) an upper liquid-pervious sheet;
   (B) a lower liquid-impervious sheet;
   (C) a fluid-absorbent core comprising from 60 to 20% by weight fibrous material and from 40 to 80% by weight of water-absorbent polymer particles comprising at least a first type of water-absorbent polymer particles (G) and at least a second type of water-absorbent polymer particles (H) based on the sum of water-absorbent polymer particles and fibrous material; and
   (D) an optional acquisition-distribution layer (D) between (A) and (C),
   wherein the first type of water absorbent polymer particles (G) of the fluid-absorbent core (C) have a SFC of at least $20 \times 10^{-7}$ $cm^3 \cdot s/g$, and wherein the at least second type of water-absorbent polymer particles (H) of the fluid-absorbent core have a sphericity of at least 0.80,
   wherein the first type of water-absorbent polymer particles (G) is present of at least 30% by weight within the fluid-absorbent core (C) and is present of at maximum 70% by weight within the fluid-absorbent core (C) based on the sum of water-absorbent polymer particles (G, H), and
   wherein the second type of water-absorbent polymer particles (H) is present of at least 30% by weight within the fluid-absorbent core (C) and is present of at maximum 70% by weight within the fluid-absorbent core (C) based on the sum of water-absorbent polymer particles (G, H).

2. A fluid-absorbent article according to claim 1, wherein the fluid-absorbing core (C) comprises at least two layers (K, L), wherein one of the layers (K) comprises from 60 to 20% by weight fibrous material and 40 to 80% by weight of the first type of water-absorbent polymer particles (G) based on the sum of water-absorbent polymer particles and fibrous material, and the second layer (L) comprises from 60 to 20% by weight fibrous material and 40 to 80% by weight of the second type of water-absorbent polymer particles (H) based on the sum of water-absorbent polymer particles and fibrous material.

3. A fluid-absorbent article according to claim 2, wherein in the fluid-absorbent core (C), the layer (K) comprising the first type of water-absorbent polymer particles (G) is arranged in z-direction above the layer (L) comprising the second type of water-absorbent polymer particles (H).

4. A fluid absorbent article according to claim 1, wherein the fluid-absorbent core (C) comprises from 60 to 20% by weight fibrous material and from 40 to 80% by weight of a mixture of the first type of water-absorbent polymer particles (G) and the second type of water-absorbent polymer particles (H) based on the sum of water-absorbent polymer particles and fibrous material.

5. A fluid-absorbent article according to claim 1, wherein the second type of water-absorbent polymer particles (H) of the fluid-absorbent core (C) have a SFC at maximum of $15 \times 10^{-7}$ cm$^3$·s/g.

6. A fluid-absorbent article according to claim 1, wherein the second type of water-absorbent polymer particles (H) of the fluid-absorbent core (C) have a SFC at maximum of $5 \times 10^{-7}$ cm$^3$·s/g.

7. A fluid absorbent article according to claim 1, wherein a production process of the first type of water absorbent polymer particles (G) of the fluid-absorbent core (C) comprises the steps of polymerization of the monomer solution, forming and comminuting a polymer gel, drying and grinding of the polymer.

8. A fluid-absorbent article according to claim 1, wherein the water absorbent polymer particles (G, H) are surface-postcrosslinked.

9. A fluid-absorbent article according to claim 1, wherein the first type of water-absorbent polymer particles (G) is present of at least 50% by weight within the fluid-absorbent core (C) based on the sum of water-absorbent polymer particles (G, H).

10. A fluid-absorbent article according to claim 1, wherein the first type of water-absorbent polymer particles (G) and the second type of water-absorbent polymer particles (H) are present within the fluid-absorbent core (C) in equal amounts by weight.

11. A fluid-absorbent article, according to claim 1, wherein for the fluid absorbent core (C), a rewet under load (RUL) for a 4th insult is reduced by at least 20% compared to a second fluid absorbent core of a second fluid-absorbent article, wherein the total amount of water-absorbent polymer particles (G and H) in the fluid-absorbent core (C) are replaced by the same amount by weight of the first type of water-absorbent polymer particles (G).

12. A fluid-absorbent article according to claim 1, wherein for the fluid absorbent core (C), a liquid acquisition time for a 4th insult is reduced by at least 5% compared to a third fluid absorbent core of a third fluid-absorbent absorbent article, wherein the total amount of water-absorbent polymer particles (G and H) are replaced by the same amount by weight of the second type of water-absorbent polymer particles (H).

13. A fluid absorbent article according to claim 1, wherein the second type of water-absorbent polymer particles (H) have an AUHL of at least 15 g/g.

14. A fluid-absorbent core (C), comprising from 60 to 20% by weight fibrous material and from 40 to 80% by weight of water-absorbent polymer particles comprising at least a first type of water-absorbent polymer particles (G) and at least a second type of water-absorbent polymer particles (H) based on the sum of water-absorbent polymer particles and fibrous material, wherein the first type of water absorbent polymer particles (G) of the fluid-absorbent core (C) have a SFC of at least $20 \times 10^{-7}$ cm$^3$·s/g and wherein the second type of water-absorbent polymer particles (H) of the fluid-absorbent core (C) have a sphericity of at least 0.80, and wherein the first type of water-absorbent polymer particles (G) is present of at least 30% by weight within the fluid-absorbent core (C) and is present of at maximum 70% by weight within the fluid-absorbent core (C) based on the sum of water-absorbent polymer particles (G, H), and wherein the second type of water-absorbent polymer particles (H) is present of at least 30% by weight within the fluid-absorbent core (C) and is present of at maximum 70% by weight within the fluid-absorbent core (C) based on the sum of water-absorbent polymer particles (G, H).

15. A fluid-absorbent core (C) according to claim 14, wherein the second type of water-absorbent polymer particles (H) of the fluid-absorbent core (C) has a SFC at maximum of $15 \times 10^{-7}$ cm$^3$·s/g.

16. A fluid absorbent core according to claim 14, wherein a production process of the first type of water absorbent polymer particles (G) of the fluid-absorbent core (C) comprises the steps of polymerization of the monomer solution, forming and comminuting a polymer gel, drying and grinding of the polymer.

17. A fluid-absorbent mixture comprising a first type of water-absorbent polymer particles (G) with a SFC of at least $20 \times 10^{-7}$ cm$^3$·s/g, and a second type of water-absorbent polymer particles (H) with a sphericity of at least 0.80, wherein the second type of water-absorbent polymer particles (H) has a SFC at maximum of $15 \times 10^{-7}$ cm$^3$·s/g;
  wherein the first type of water-absorbent polymer particles (G) is present of at least 30% by weight within the fluid-absorbent mixture and is present of at maximum 70% by weight within the fluid-absorbent mixture based on the sum of water-absorbent polymer particles (G, H); and
  wherein the second type of water-absorbent polymer particles (H) is present of at least 30% by weight within the fluid-absorbent mixture and is present of at maximum 70% by weight within the fluid-absorbent mixture based on the sum of water-absorbent polymer particles (G, H).

18. A fluid-absorbent mixture according to claim 17, wherein a production process of the first type of water absorbent polymer particles (G) comprises the steps of polymerization of the monomer solution, forming and comminuting a polymer gel, drying and grinding of the polymer.

* * * * *